US008921106B2

(12) United States Patent
Gurney et al.

(10) Patent No.: US 8,921,106 B2
(45) Date of Patent: Dec. 30, 2014

(54) ANTIBODIES THAT BIND THE GLUTAMATE LIGAND BINDING REGION OF NOTCH3

(71) Applicant: OncoMed Pharmaceuticals, Inc., Redwood City, CA (US)

(72) Inventors: Austin L. Gurney, San Francisco, CA (US); Aaron Ken Sato, Burlingame, CA (US); Maureen Fitch-Bruhns, San Mateo, CA (US)

(73) Assignee: OncoMed Pharmaceuticals, Inc., Redwood City, CA (US)

( * ) Notice: Subject to any disclaimer, the term of this patent is extended or adjusted under 35 U.S.C. 154(b) by 0 days.

(21) Appl. No.: 13/890,805

(22) Filed: May 9, 2013

(65) Prior Publication Data

US 2013/0323257 A1   Dec. 5, 2013

Related U.S. Application Data

(62) Division of application No. 13/308,224, filed on Nov. 30, 2011, now Pat. No. 8,460,661, which is a division of application No. 12/010,421, filed on Jan. 24, 2008, now Pat. No. 8,088,617.

(60) Provisional application No. 60/886,414, filed on Jan. 24, 2007.

(51) Int. Cl.
| | |
|---|---|
| *C07K 16/28* | (2006.01) |
| *C12N 5/12* | (2006.01) |
| *A61K 31/337* | (2006.01) |
| *C07K 14/705* | (2006.01) |
| *C07K 7/06* | (2006.01) |
| *A61K 39/395* | (2006.01) |
| *A61K 39/00* | (2006.01) |

(52) U.S. Cl.
CPC ............ *C07K 16/28* (2013.01); *C07K 2317/565* (2013.01); *C07K 2317/734* (2013.01); *C07K 2317/56* (2013.01); *A61K 39/39558* (2013.01); *C07K 2317/55* (2013.01); *C07K 2317/732* (2013.01); *C07K 2317/34* (2013.01); *C07K 2317/92* (2013.01); *A61K 31/337* (2013.01); *C12N 5/12* (2013.01); *A61K 2039/505* (2013.01); *C07K 2317/76* (2013.01); *Y10S 530/809* (2013.01)
USPC ........ 435/326; 435/331; 435/334; 530/388.1; 530/388.22; 530/387.9; 530/809; 530/326; 530/350

(58) Field of Classification Search
CPC ........ C07K 16/00; C07K 16/18; C07K 16/28; C07K 16/30; C07K 2316/96; C07K 2317/56; C07K 2317/565; C07K 2317/73; C07K 2317/76; C07K 2317/92; C07K 2317/734; C07K 2317/24; C07K 14/705; C07K 14/71; C07K 7/06; C07K 7/08; A61K 39/39533
See application file for complete search history.

(56) References Cited

U.S. PATENT DOCUMENTS

| | | | |
|---|---|---|---|
| 5,648,464 | A | 7/1997 | Artavanis-Tsakonas et al. |
| 5,786,158 | A | 7/1998 | Artavanis-Tsakonas et al. |
| 5,789,195 | A | 8/1998 | Artavanis-Tsakonas et al. |
| 5,854,027 | A | 12/1998 | Steipe et al. |
| 6,004,528 | A | 12/1999 | Bergstein |
| 6,080,588 | A | 6/2000 | Glick |
| 6,083,904 | A | 7/2000 | Artavanis-Tsakonas |
| 6,090,922 | A | 7/2000 | Artavanis-Tsakonas et al. |
| 6,180,370 | B1 | 1/2001 | Queen et al. |
| 6,379,925 | B1 | 4/2002 | Kitajewski et al. |
| 6,537,775 | B1 | 3/2003 | Tournier-Lasserve et al. |
| 6,689,744 | B2 | 2/2004 | Gao et al. |
| 6,692,919 | B1 | 2/2004 | Artavanis-Tsakonas et al. |
| 6,984,522 | B2 | 1/2006 | Clarke et al. |
| 7,091,323 | B2 | 8/2006 | Pan et al. |
| 7,115,360 | B2 | 10/2006 | Clarke et al. |
| 7,282,203 | B2 | 10/2007 | Coignet |
| 7,432,364 | B2 | 10/2008 | Pan et al. |
| 7,632,926 | B2 | 12/2009 | Kim et al. |
| 7,713,710 | B2 | 5/2010 | Clarke et al. |
| 7,754,206 | B2 | 7/2010 | Clarke et al. |
| 7,850,961 | B2 | 12/2010 | Clarke et al. |
| 7,919,092 | B2 | 4/2011 | Lewicki et al. |
| 8,088,617 | B2 | 1/2012 | Gurney et al. |
| 8,206,713 | B2 | 6/2012 | Lewicki et al. |
| 8,226,943 | B2 | 7/2012 | Gurney et al. |
| 8,404,237 | B2 | 3/2013 | Lewicki et al. |
| 8,425,903 | B2 | 4/2013 | Gurney et al. |
| 8,435,513 | B2 | 5/2013 | Gurney et al. |
| 8,460,661 | B2 | 6/2013 | Gurney et al. |

(Continued)

FOREIGN PATENT DOCUMENTS

| | | |
|---|---|---|
| DE | 44 25 115 A1 | 1/1996 |
| EP | 0662827 B2 | 7/1995 |

(Continued)

OTHER PUBLICATIONS

Bellavia et al. Notch3: from subtle structural differences to functional diversity. Oncogene 27: 5092-5098, 2008.*
Cui et al. Notch3 functions as a tumor suppressor by controlling cellular senescence. Cancer Res 73(11): 3451-2459, 2013.*
Monet-Lepretre et al. Distinct phenotypic and functional features of CADASIL mutations in the Notch3 ligand binding domain. Brain 132: 1601-1612, 2009.*

(Continued)

*Primary Examiner* — Bridget E Bunner
(74) *Attorney, Agent, or Firm* — Sterne, Kessler, Goldstein & Fox P.L.L.C.

(57) ABSTRACT

Isolated antibodies that specifically binds to an extracellular conserved ligand binding region of a human Notch receptor and inhibits growth of a tumor are described. Also described are methods of treating cancer, the method comprising administering an anti-Notch antibody in an amount effective to inhibit tumor growth.

15 Claims, 10 Drawing Sheets

(56) References Cited

U.S. PATENT DOCUMENTS

Figure 1A:
Figure 3A:
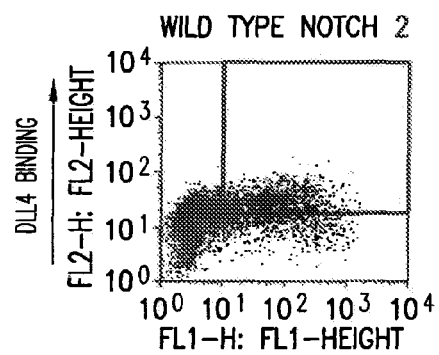
Figure 3B:
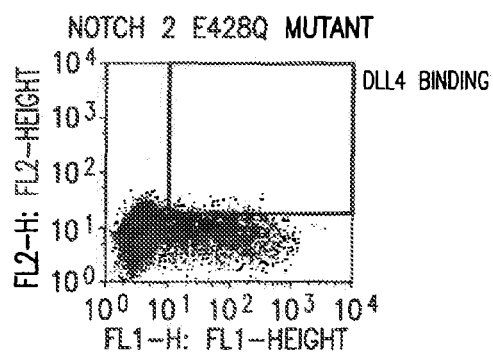
Figure 3C:
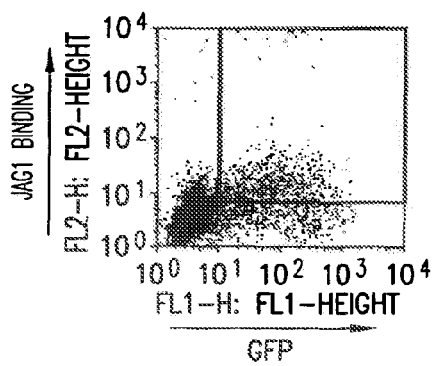
Figure 3D:
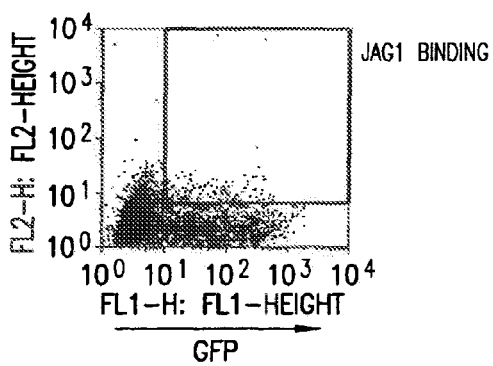

| | | |
|---|---|---|
| 2002/0086014 A1 | 7/2002 | Korman et al. |
| 2002/0119565 A1 | 8/2002 | Clarke et al. |
| 2002/0122802 A1 | 9/2002 | Wands et al. |
| 2003/0082651 A1 | 5/2003 | Gao et al. |
| 2003/0083465 A1 | 5/2003 | Zimrin et al. |
| 2003/0186290 A1 | 10/2003 | Tournier-Lasserve et al. |
| 2004/0229301 A1 | 11/2004 | Wang |
| 2005/0026831 A1 | 2/2005 | Bodmer et al. |
| 2005/0089518 A1 | 4/2005 | Clarke et al. |
| 2005/0112121 A1 | 5/2005 | Artavanis-Tsakonas et al. |
| 2005/0142635 A1 | 6/2005 | Tsuchiya et al. |
| 2005/0187179 A1 | 8/2005 | Miele et al. |
| 2005/0232927 A1 | 10/2005 | Clarke et al. |
| 2006/0030694 A1 | 2/2006 | Kitajewski et al. |
| 2006/0051325 A1 | 3/2006 | Clarke et al. |
| 2006/0073125 A1 | 4/2006 | Clarke et al. |
| 2006/0083682 A1 | 4/2006 | Bergstein |
| 2006/0263774 A1 | 11/2006 | Clark et al. |
| 2007/0036800 A1 | 2/2007 | Bergstein |
| 2007/0036801 A1 | 2/2007 | Bergstein |
| 2007/0036804 A1 | 2/2007 | Bergstein |
| 2007/0041984 A1 | 2/2007 | Bergstein |
| 2007/0196047 A9 | 8/2007 | Levner et al. |
| 2007/0212737 A1 | 9/2007 | Clarke et al. |
| 2007/0265246 A1 | 11/2007 | Clevers et al. |
| 2008/0076670 A1 | 3/2008 | Sivan et al. |
| 2008/0112940 A1 | 5/2008 | Liaw |
| 2008/0118520 A1 | 5/2008 | Li et al. |
| 2008/0131434 A1 | 6/2008 | Lewicki et al. |
| 2008/0131908 A1 | 6/2008 | Li et al. |
| 2008/0132423 A1 | 6/2008 | Kondo |
| 2008/0178305 A1 | 7/2008 | Clarke et al. |
| 2008/0187532 A1 | 8/2008 | Gurney et al. |
| 2008/0188405 A1 | 8/2008 | Di Fiore et al. |
| 2008/0194022 A1 | 8/2008 | Clarke et al. |
| 2008/0226621 A1 | 9/2008 | Fung et al. |
| 2008/0260734 A1 | 10/2008 | Clarke et al. |
| 2009/0004205 A1 | 1/2009 | Clarke et al. |
| 2009/0028856 A1 | 1/2009 | Chen et al. |
| 2009/0047285 A1 | 2/2009 | Gurney et al. |
| 2009/0081238 A1 | 3/2009 | Siebel et al. |
| 2009/0208491 A1 | 8/2009 | Gurney et al. |
| 2010/0111958 A1 | 5/2010 | Gurney et al. |
| 2011/0033481 A1 | 2/2011 | Clarke et al. |
| 2011/0092378 A1 | 4/2011 | Clarke et al. |
| 2011/0195065 A1 | 8/2011 | Lewicki et al. |
| 2011/0311552 A1 | 12/2011 | Gurney et al. |
| 2012/0213786 A1 | 8/2012 | van der Horst |
| 2013/0243774 A1 | 9/2013 | van der Horst et al. |
| 2013/0251705 A1 | 9/2013 | Lewicki et al. |
| 2013/0260455 A1 | 10/2013 | Gurney et al. |
| 2013/0280277 A1 | 10/2013 | Gurney et al. |
| 2013/0296536 A1 | 11/2013 | Gurney et al. |
| 2013/0323266 A1 | 12/2013 | Hoey et al. |
| 2014/0011271 A1 | 1/2014 | Gurney et al. |

FOREIGN PATENT DOCUMENTS

| | | |
|---|---|---|
| JP | 2002-526109 A | 8/2002 |
| WO | WO 94/07474 A1 | 4/1994 |
| WO | WO 97/37004 A1 | 10/1997 |
| WO | WO 97/45143 A1 | 12/1997 |
| WO | WO 98/57621 A1 | 12/1998 |
| WO | WO 00/20576 A2 | 4/2000 |
| WO | WO 00/52143 A2 | 9/2000 |
| WO | WO 02/00576 A1 | 1/2002 |
| WO | WO 02/12447 A2 | 2/2002 |
| WO | WO 02/18544 A | 3/2002 |
| WO | WO 03/042246 A2 | 5/2003 |
| WO | WO 03/050502 A | 6/2003 |
| WO | WO 03/062273 A2 | 7/2003 |
| WO | WO 2004/001004 A2 | 12/2003 |
| WO | WO 2004/052389 | 6/2004 |
| WO | WO 2004/091383 A2 | 10/2004 |
| WO | WO 2004/094475 A2 | 11/2004 |
| WO | WO 2005/026334 A2 | 3/2005 |
| WO | WO 2005/054434 A2 | 6/2005 |
| WO | WO 2005/074633 A2 | 8/2005 |
| WO | WO 2006/110581 A2 | 10/2006 |
| WO | WO 2007/145840 A2 | 12/2007 |
| WO | WO 2008/051797 A3 | 5/2008 |
| WO | WO 2008/057144 A2 | 5/2008 |
| WO | WO 2008/076960 A2 | 6/2008 |
| WO | WO 2008/091641 A2 | 7/2008 |
| WO | WO 2008/108910 A2 | 9/2008 |
| WO | WO 2008/136848 A2 | 11/2008 |
| WO | WO 2008/150525 A1 | 12/2008 |
| WO | WO 2009/025867 A2 | 2/2009 |
| WO | WO 2009/035522 A1 | 3/2009 |
| WO | WO 2010/005567 A2 | 1/2010 |
| WO | WO 2010/039832 | 4/2010 |
| WO | WO 2011/088215 | 7/2011 |
| WO | WO 2012/003472 | 1/2012 |

OTHER PUBLICATIONS

Rusanescu et al. Notch signaling in cardiovascular disease and calcification. Curr Cardiol Rev 4: 148-156, 2008.*

Song et al. Cancer stem cells—an old idea that's new again: implications for the diagnosis and treatment of breast cancer. Expert Opin Biol Ther 7(4): 431-438, 2007.*

Tannock and Hill. The Basic Science of Oncology. 1998. New York: McGraw-Hill;; pp. 357-358.*

Al-Hajj et al., "Prospective identification of tumorigenic breast cancer cells," *Cell Biology* 100:3983-3988, Proceedings of the National Academy of Science, United States (2003).

Arias, A.M., et al. "CSL-independent Notch signalling: a checkpoint in cell fate decisions during development?," *Curr. Opin. Genet. Dev.* 12:524-533, Elsevier Science Ltd., England (2002).

Artavanis-Tsakonas, S., et al., "Notch Signalling: Cell Fate Control and Signal Integration in Development," *Science* 284:770-776, American Association for the Advancement of Science, United States (1999).

Brennan, K. and Brown, A., "Is there a role for Notch signalling in human breast cancer?," *Breast Cancer Res.* 5:69-75, BioMed Central Ltd., England (2003).

Brennan, K., et al., "Repression by Notch is required before Wingless signalling during muscle progenitor cell development in *Drosophila*," *Curr. Biol.* 9:707-710, Elsevier Science Ltd., England (1999).

Cole, S.P.C., et al., "The Ebv-Hybridoma Technique and Its Application to Human Lung Cancer," *Monoclonal Antibodies and Cancer Therapy* 77-96, Alan R. Liss, United States (1985).

Del Amo, F.F., et al. "Cloning, Analysis, and Chromosomal Localization of *Notch*-1, a Mouse Homolog of *Drosophila* Notch," *Genomics* 15:259-264, Academic Press, Inc., United States (1993).

Domenga, V., et al., "*Notch*3 is required for arterial identity and maturation of vascular smooth muscle cells," *Genes Dev.* 18:2730-2735, Cold Spring Harbor Laboratory Press, United Sates (2004).

Duncan, A.W., et al., "Integration of Notch and Wnt signaling in hematopoietic stem cell maintenance," *Nature Immunol.* 6:314-322, Nature Publishing Group, United States (2005).

Ellisen, L.W., et al., "*TAN-l*, the Human Homolog of the *Drosophila Notch* Gene, is Broken by Chromosomal Translocations in T Lymphoblastic Neoplasms," *Cell* 66:649-661, Cell Press, United States (1991).

Gale, N. W., et al., "Haploinsufficiency of delta-like 4 ligand results in embryonic lethality due to major defects in arterial and vascular development," *Proc. Natl. Acad. Sci. USA* 101:15949-15954, The National Academy of Sciences of the USA, United States (2004).

Gallahan, D., et al., "Expression of a Truncated *Int*3 Gene in Developing Secretory Mammary Epithelium Specifically Retards Lobular Differentiation Resulting in Tumorigenesis," *Can. Res.* 56:1775-1785, American Association for Cancer Research, Inc, United States (1996).

Gridley, T., "Notch signaling and inherited disease syndromes," *Hum. Mol. Genet.* 12:R9-R13, Oxford University Press, England (2003).

(56) References Cited

OTHER PUBLICATIONS

Gridley, T., "Notch signaling during vascular development," *Proc. Natl. Acad. Sci.* 98:5377-5378, National Academy of Sciences, United States (2001).
Gridley, T., "Vessel guidance," *Nature* 445:722-723, Nature Publishing Group, United States (2007).
Gridley, T., "Notch Signaling in Vertebrate Development and Disease," *Mol. Cell. Neurosci.* 9:103-108, Academic Press, United States (1997).
Hadland, B.K., et al., "A requirement for Notch1 distinguishes 2 phases of definitive hematopoiesis during development," *Blood* 104:3097-3105, The American Society of Hematology, United States (2004).
Hainaud, P., et al., "The Role of the Vascular Endothelial Growth Factor-Delta-like 4 Ligand/Notch4-Ephrin B2 Cascade in Tumor Vessel Remodeling and Endothelial Cell Functions," *Cancer Res.* 66:8501-8510, American Association for Cancer Research, United States (2006).
Hallahan, A.R., et al., "The SmoA1 Mouse Model Reveals That Notch Signaling is Critical for the Growth and Survival of Sonic Hedgehog-Induced Medulloblastomas," *Cancer Res.* 64:7794-7800, American Association for Cancer Research, United States (2004).
Hitoshi, S., et al., "Notch pathway molecules are essential for the maintenance, but not the generation, of mammalian neural stem cells," *Genes Dev.* 16:846-858, Cold Spring Harbor Laboratory Press, United States (2002).
Iso, T., et al., "Notch Signaling in Vascular Development," *Arterioscler. Thromb. Vasc. Biol.* 23:543-553, American Heart Association, Inc., United States (2003).
Jhappan, C., et al., "Expression of an activated *Notch*-related *int*-3 transgene interferes with cell differentiation and induces neoplastic transformation in mammary and salivary glands," *Genes Dev.* 6:345-355, Cold Spring Harbor Laboratory Press, United States (1992).
Joutel, A. and Tournier-Lasserve, E., "Notch signalling pathway and human diseases," *Semin. Cell Dev. Biol.* 9:619-625, Academic Press, United States (1998).
Joutel, A., et al., "*Notch*3 Mutations in CADASIL, a Hereditary adult-onset condition causing stroke and dementia," *Nature* 383:707-710, Nature Publishing Group, England (1996).
Karanu, F.N., et al., "The Notch Ligand Jagged-1 Represents a Novel Growth Factor of Human Hematopoietic Stem Cells," *J. Exp. Med.* 192: 1365-1372, Rockefeller University Press, United States (2000).
Kidd, S., et al., "Sequence of the Notch Locus of *Drosophila melanogaster*: Relationship of the Encoded Protein to Mammalian Clotting and Growth Factors," *Mol. Cell Biol.* 6:3094-3108, American Society for Microbiology, United States (1986).
Kopper, L. and Hajdú, M., "Tumor Stem Cells," *Pathol. Oncol. Res.* 10:69-73, Aráanyi Lajos Foundation, Hungary (2004).
Krebs, L.T., et al., "Notch signaling is essential for vascular morphogenesis in mice," *Genes Dev.* 14:1343-1352, Cold Spring Harbor Laboratory Press, United States (2000).
Kuukasjärvi, T., et al., "Genetic Heterogeneity and Clonal Evolution Underlying Development of Asynchronous Metastasis in Human Breast Cancer," *Cancer Res.* 57:1597-1604, American Association for Cancer Research, Inc., United States (1997).
Lapidot, T., et al., "A cell initiating human acute myeloid leukaemia after transplantation into SCID mice," *Nature* 367:645-648 Nature Publishing Group, England (1994).
Lawrence, N., et al., "Notch signaling targets the Wingless responsiveness of a *Ubx* visceral mesoderm enhancer in *Drosophila*," *Curr. Biol.* 11:375-385, Elsevier Science Ltd., England (2001).
Leethanakul, C., et al., "Distinct pattern of expression of differentiation and growth-related genes in squamous cell carcinomas of the head and neck revealed by the use of laser capture microdissection and cDNA arrays," *Oncogene* 19:3220-3224, Nature Publishing Group, England (2000).
Leong, K.G., and Karsan, A., "Recent insights into the role of Notch signaling in Tumorigenesis," *Blood* 107:2223-2233, American Society of Hematology, United States (2006).
Leong, K.G., et al., "Activated Notch4 Inhibits Angiogenesis: Role of β1-Integrin Activation," *Mol. Cell. Biol.* 22:2830-2841, American Society for Microbiology, United States (2002).
McCright, B., et al., "Defects in development of the kidney, heart and eye vasculature in mice homozygous for a hypomorphic *Notch2* mutation," *Development* 128:491-502, The Company of Biologists Limited, England (2001).
Mohr, O., "Character Changes Caused by Mutation of an Entire Region of a Chromosome in *Drosophila*," *Genetics* 4:275-282, The Genetics Society of America, United States (1919).
Parr, C., et al., "The possible correlation of Notch-1 and Notch-2 with clinical outcome and tumour clinicopathological parameters in human breast cancer," *Int. J. Mol. Med.* 14:779-786, Springer Verlag, Germany (2004).
Pear, W.S. and Aster, J.C., "T cell acute lymphoblastic leukemia/lymphoma: a human cancer commonly associated with aberrant NOTCH1 signaling," *Curr. Opin. Hematol.* 11:426-433, Lippincott Williams & Wilkins, United States (2004).
Politi, K., et al., "Notch in mammary gland development and breast cancer," *Semin. Cancer Biol.* 14:341-347, Elsevier Science Ltd., England (2004).
Purow, B.W., et al., "Expression of Notch-1 and Its Ligands, Delta-Like-1 and Jagged-1, Is Critical for Glioma Cell Survival and Proliferation," *Clin. Res.* 65:2353-2363, American Association for Cancer Research, United States (2005).
Rae, F.K., et al., "Novel Association of a Diverse Range of Genes With Renal Cell Carcinoma as Identified by Differential Display," *Int. J. Cancer* 88:726-732, Wiley-Liss, Inc., United States (2000).
Rebay, I., et al., "Specific EGF Repeats of Notch Mediate Interactions with Delta and Serrate: Implications for Notch as a Multifunctional Receptor," *Cell* 67:687-699, Cell Press, United States (1991).
Reya, T., et al., "Stem cells, cancer, and cancer stem cells," *Nature* 414:105-111, Nature Publishing Group, United States (2001).
Robey, E., et al., "An Activated Form of Notch Influences the Choice between CD4 and CD8 T Cell Lineages," *Cell* 87:483-492, Cell Press, United States (1996).
Smith, G.H., et al., "Constitutive Expression of a Truncated *INT*3 Gene in Mouse Mammary Epithelium Impairs Differentiation and Functional Development," *Cell Growth Differ.* 6:563-577, American Association for Cancer Research, United States (1995).
Soriano, J.V., et al., "Expression of an Activated Notch4(int-3) Oncoprotein Disrupts Morphogenesis and Induces an Invasive Phenotype in Mammary Epithelial Cells in Vitro," *Int. J. Cancer* 86:652-659, Wiley-Liss, Inc., United States (2000).
Suzuki, T., et al., "Imbalanced expression of *TAN*-1 and human *Notch4* in endometrial cancers," *Int. J. Oncol.* 17:1131-1139, Spandidos publications, Greece (2000).
Swiatek, P.J., et al., "*Notch*1 is essential for postimplantation development in mice," *Genes Dev.* 8:707-719, Cold Spring Harbor Laboratory Press, United States (1994).
Takeshita, K., et al., "Critical Role of Endothelial Notch1 Signaling in Postnatal Angiogenesis," *Circ. Res.* 100:70-78, American Heart Association, Inc., United States (2007).
Tavares, M.J., et al., "Inhibition of Vascular Endothelium by the Notch-Ligand Delta-4 Unveils a Novel Therapeutic Target," *Vascular Wall Biology*, Poster Board No. Session: 115-II, Abstract No. 1944, pp. 531a, American Society of Hematology, United States (2003).
Uyttendaele, H., et al., "Notch4 and Wnt-1 Proteins Function to Regulate Branching Morphogenesis of Mammary Epithelial Cells in an Opposing Fashion," *Dev. Bio.* 196:204-217, Academic Press, United States (1998).
Van Es, J.H. and Clevers, H., "Notch and Wnt inhibitors as potential new drugs for intestinal neoplastic disease," *Trends Mol. Med.* 11:496-502, Elsevier Science Ltd., England (2005).
Van Limpt, V., et al., "SAGE Analysis of Neuroblastoma Reveals a High Expression of the Human Homologue of the *Drosophila Delta* Gene," *Medical Pediatr. Oncol.* 35:554-558, Wiley-Liss, Inc., United States (2000).
Varnum-Finney, B., et al., "Pluripotent, cytokine-dependent, hematopoietic stem cells are immortalized by constitutive Notch 1 signalling," *Nature Med.* 6:1278-1281, Nature Publishing Group, United States (2000).

(56) References Cited

OTHER PUBLICATIONS

Weijzen, S., et al., "Activation of Notch-1 signaling maintains the neoplastic phenotype in human Ras-transformed cells," *Nature Med.* 8:979-986, Nature Publishing Group, United States (2002).
Wharton, K.A., et al., "Nucleotide Sequence from the Neurogenic Locus Notch Implies a Gene Product That Shares Homology with Proteins Containing EGF-like Repeats," *Cell* 43:567-581, Cell Press, United States (1985).
Xu, A., et al., "Regions of *Drosophila* Notch That Contribute to Ligand Binding and the Modulatory Influence of Fringe," *J. Biol. Chem.* 280:30158-30165, The American Society for Biochemistry and Molecular Biology, Inc., United States (2005).
Xue, Y., et al., "Embryonic lethality and vascular defects in mice lacking the Notch ligand Jagged1" *Hum. Mol. Genet.* 8:723-730, Oxford University Press, England (1999).
Zagouras, P., et al., "Alterations in Notch signaling in neoplastic lesions of the human cervix," *Proc. Natl. Acad. Sci. USA* 92:6414-6418, National Academy of Sciences, United States (1995).
The Extended European Search Report issued in European Application No. EP 07 777 332.3, on Aug. 11, 2009 (10 pages).
Sakamoto, K., et al., "Distinct roles of EGF repeats for the Notch signaling system," *Exp. Cell Res.* 302:281-291, Elsevier Inc., United States (2005).
Shao, Li, et al., "Fringe Modifies O-Fucose on Mouse Notch1 at Epidermal Growth Factor-like Repeats within the Ligand-binding Site and the Abruptex Region," *The J. Biol. Chem*, 278:7775-7782, The American Society for Biochemistry and Molecular Biology, Inc., United States (2003).
Peters, N., et al., "CADASIL-associated Notch3 mutations have differential effects both on ligand binding and ligand-induced Notch3 receptor signaling through RBP-Jk," *Exp. Cell Res.* 299:454-464, Elsevier Inc., United States (2004).
Summons to attend oral proceedings pursuant to Rule 115(1) EPC for European Patent Application 05722705.0-2402/1718767, European Patent Office, Germany, mailed on Feb. 9, 2011.
Thelu, J., et al., "Notch signalling is linked to epidermal cell differentiation level in basal cell carcinoma, psoriasis and wound healing," *BMC Dermatol.* 2:7-18, BioMed Central Ltd., England (2002).
Jang, M.-S., et al., "Notch signaling as a target in multimodality cancer therapy," *Curr. Opin. Mol. Ther.* 2:55-65, Thomson Reuters (Scientific.) Ltd., England (2000).
Pelegrin, A., et al., "[Immunotargeting of tumors: state of the art and prospects in 2000]," *Bull. Cancer* 87(11):777-91, John Libbey Eurotext, France (2000) in the French language.
Pelegrin, A., et al., "[Immunotargeting of tumors: state of the art and prospects in 2000]," *Bull. Cancer* 87(11):777-91, John Libbey Eurotext, France (2000) in the English language.
Weng, A.P. and Aster, J.C., "Multiple niches for Notch in cancer: context is everything," *Curr. Opin. Genet. Dev.* 14:48-54, Elsevier, England (2004).
Liu, Z., et al., "*Notch*1 loss of heterozygosity causes vascular tumors and lethal hemorrhage in mice," *J. Clin. Invest.* 121(2):800-808, American Society for Clinical Investigation, United States (Feb. 2011; Epub Jan. 25, 2011).
Allenspach, E.J., et al., "Notch Signaling in Cancer," *Cancer Biol. Ther.* 1:466-476, Landes Bioscience, United States (2002).
Armstrong, F., et al., "NOTCH is a key regulator of human T-cell acute leukemia initiating cell activity," *Blood* 113:1730-1740, The American Society of Hematology, United States (2009).
Bellavia, D., et al., "Constitutive activation of NF-κB and T-cell leukemia/lymphoma in Notch3 transgenic mice," *EMBO J.* 19:3337-3348, European Molecular Biology Organization, England (2000).
Bheeshmachar, G., et al., "Evidence for a Role for Notch Signaling in the Cytokine-Dependent Survival of Activated T cells," *J. Immunol.* 177:5041-5050, The American Association of Immunologists Inc., United States (2006).
Callahan, R. and Raafat, A., "Notch Signaling in Mammary Gland Tumorigenesis," *J. Mammary Gland Biol. and Neoplasia* 6:23-36, Plenum Publishing Corporation, United States (2001).

Campbell, A.M., "Monoclonal antibody technology," vol. 13, pp. v-23, Elsevier Science Publishers B.V, Netherlands, 1984.
Cox, C.V., et al., "Characterization of acute lymphoblastic leukemia progenitor cells," *Blood* 104:2919-2925, The American Society of Hematology, United States (2004).
Deftos, M.L., et al., "Correlating Notch Signaling with Thymocyte Maturation," *Immunity* 9:777-786, Cell Press, United States (1998).
Dikic, I. and Schmidt, M.H.H., "Notch: Implications of endogenous inhibitors for therapy," *Bioessays* 32:481-487, Wiley Periodicals, Inc., United States (2010).
English language Abstract of WIPO Patent Publication No. WO 02/00576 A1, accessed Jun. 7, 2010.
Extended European Search Report of European Appl. No. 08 724 737.5, European Patent Office, Munich, Germany, dated Sep. 24, 2010.
Fleming, R.J., et al., "The NOTCH receptor and its ligands," *Trends in Cell Biol.* 7:437-441, Elsevier Science Ltd., England (1997).
Fre, S., et al., "Notch signals control the fate of immature progenitor cells in the intestine," *Nature* 435:964-968, Nature Publishing Group, England (2005).
Gallahan, D. and Callahan, R., "The mouse mammary tumor associated gene *INT*3 is a unique member of the *NOTCH* gene family (*NOTCH*4)," *Oncogene* 14:1883-1890, Stockton Press, United States (1997).
Grabher, C., et al., "Notch 1 activation in the molecular pathogenesis of T-cell acute lymphoblastic leukaemia," *Nat. Rev. Cancer* 6:347-359, Nature Publishing Group, England (2006).
Hambleton, S., et al., "Structural and Functional Properties of Human Notch-1 Ligand Binding Region," *Structure* 12:2173-83, Elsevier Ltd., United States (2004).
Imatani, A. and Callahan, R., "Identification of a novel *NOTCH*-4/*INT*-3 RNA species encoding an activated gene product in certain human tumor cell lines," *Oncogene* 19:223-231, Macmillan Publishers Ltd., England (2000).
International Search Report for International Application No. PCT/US08/00884, United States Patent and Trademark Office, U.S.A., mailed on Oct. 1, 2008.
International Search Report for International Application No. PCT/US09/03994, ISA/US, Alexandria, Virginia, USA, mailed on Jul. 23, 2010.
International Search Report for International Application No. PCT/US09/03995, United States Patent and Trademark Office, U.S.A., mailed on Mar. 2, 2010.
International Search Report for International Application No. PCT/US2008/001948, United States Patent and Trademark Office, U.S.A., mailed on Oct. 15, 2008.
Jarriault, S., et al., "Signalling downstream of activated mammalian Notch," *Nature* 377:355-358, Nature Publishing Group, England (1995).
Jehn, B.M., et al., "Cutting Edge: Protective Effects of Notch-1 on TCR-Induced Apoptosis," *J. Immunol.* 162:635-638, The American Association of Immunologists, Inc., United States (1999).
Jundt, F., et al., "Activated Notch1 signaling promotes tumor cell proliferation and survival in Hodgkin and anaplastic large cell lymphoma," *Blood* 99:3398-3403, The American Society of Hematology, United States (2002).
Lee, J-S., et al., "Intracisternal Type A Partical-Mediated Activation of the *Notch4/int3* Gene in a Mouse Mammary Tumor: Generation of Truncated *Notch4/int3* mRNAs by Retroviral Splicing Events." *J. Virol.* 73:5166-5171, American Society for Microbiology, United States (1999).
Lee, S-H., et al., "Mutational analysis of *NOTCH*1, 2, 3 and 4 genes in common solid cancers and acute leukemias," *APMIS* 115:1357-1363, The Authors Journal Compilation, Denmark (2007).
Li, K., et al., "Modulation of Notch Signaling by Antibodies Specific for the Extracellular Negative Regulatory Region of NOTCH3," *J. Biol. Chem.* 283:8046-8054, The American Society for Biochemistry and Molecular Biology, Inc., United States (2008).
Li, L., et al., "The Human Homolog of Rat *Jagged*1 Expressed by Marrow Stroma Inhibits Differentiation of 32D Cells through Interaction with Notch1," *Immunity* 8:43-55, Cell Press, United States (1998).

(56) References Cited

OTHER PUBLICATIONS

Li, L., et al., "Cloning, Characterization, and the Complete 56.8-Kilobase DNA Sequence of the Human NOTCH4 Gene," *Genomics* 51:45-48, Academic Press, United States (1998).

Lin, L., et al., "Targeting Specific Regions of the Notch3 Ligand-Binding Domain Induces Apoptosis and Inhibits Tumor Growth in Lung Cancer," *Cancer Res.* 70:632-8, American Association for Cancer Research, United States (Jan. 15, 2010; Epub Jan. 12, 2010).

Lindsell, C.E., et al., "Jagged: A Mammalian Ligand That Activates Notch1," *Cell* 80:909-917, Cell Press, United States (1995).

Luo, B., et al., "Isolation and Functional Analysis of a cDNA for Human *Jagged2*, a Gene Encoding a Ligand for the Notch1 Receptor," *Mol. Cell. Biol.* 17:6057-6067, American Society for Microbiology, United States (1997).

Miele, L., "Gamma-secretase and notch signaling: Novel therapeutic targets in breast cancer," DTIC Online May 17, 2006, available at: http://www.dtic.mil/srch/doc?collection=t3&id=ADA446389 (retrieved Jan. 12, 2010).

Miele, L. & Osborne, B., "Arbiter of Differentiation and Death: Notch Signaling Meets Apoptosis," *J. Cell Physiol.* 181:393-409, Wiley-Liss, Inc., United States (1999).

Nam, Y., et al., "Notch signaling as a therapeutic target," *Curr. Opin. Chem. Biol.* 6:501-509, Elsevier Science Ltd., England (2002).

Novus, "Biologicals Product: Mouse Monoclonal antibody to Notch 1 (A6) antibody datasheet," accessed at http://www.novusbio.com/data_sheet/pdf_data_sheet/5985 2006.

Pei, Z. and Baker, N. E., "Competition between Delta and the Abruptex domain of Notch," *BMC Dev. Biol.* 8:4, BioMed Central Ltd., England (2008).

Sambandam, A., et al., "Notch signaling controls the generation and differentiation of early T lineage progenitors," *Nature Immunol.* 6:663-670, Nature Publishing Group, United States (2005).

Shimizu, K., et al., "Physical Interaction of Delta1, Jagged1, and Jagged2 with Notch1 and Notch3 Receptors," *Biochem. Biophys. Res. Commun.* 276:385-389, Academic Press, United States (2000).

Soriano, J.V., et al., "Expression of an Activated Notch(int-3) Oncoprotein Disrupts Morphogenesis and Induces an Invasive Phenotype in Mammary Epithelial Cells in Vitro," *Int. J. Cancer* 86: 652-659, Wiley-Liss, Inc., United States (2000).

Sugaya, K., et al., "Gene organization of human NOTCH4 and (CTG)$n$ polymorphism in this human counterpart gene of mouse proto-oncogene *Int3*," *Gene* 189:235-244, Elsevier Science B.V., Netherlands (1997).

Van Es, J.H., et al., "Notch/γ-secretase inhibition turns proliferative cells in intestinal crypts and adenomas into goblet cells," *Nature* 435:959-963, Nature Publishing Group, England (2005).

Weng, A.P., et al., "Activating Mutations of *NOTCH*1 in Human T Cell Acute Lymphoblastic Leukemia," *Science* 306:269-271, American Association for the Advancement of Science, United States (2004).

Weng, A.P., et al., "Growth Suppression of Pre-T Acute Lymphoblastic Leukemia Cells by Inhibition of Notch Signaling," *Mol. Cell Biol.* 23:655-664, American Society for Microbiology, United States (2003).

Axelson, H., "Notch signaling and cancer: emerging complexity,"*Semin. Cancer Biol.* 14:317-319, Elsevier Ltd., England (2004).

Curry, C.L., et al., "Gamma secretase inhibitor blocks Notch activation and induces apoptosis in Kaposi's sarcoma tumor cells," *Oncogene* 24:6333-6344, Nature Publishing Group, England (2005).

Dontu, G., et al., "Role of Notch signaling in cell-fate determination of human mammary stem/progenitor cells," *Breast Cancer Res.* 6:R605-R615, BioMed Central Ltd., England (2004).

Duan, Z., et al., "A Novel Notch Protein, N2N, Targeted by Neutrophil Elastase and Implicated in Hereditary Neutropenia," *Mol. Cell. Biol.* 24:58-70, American Society for Microbiology, United States (2004).

Harper, J.A., et al., "Notch signaling in development and disease," *Clin. Genet.* 64:461-472, Blackwell Munksgaard, Denmark (2003).

Hopfer, O., et al., "The Notch pathway in ovarian carcinomas and adenomas," *Br. J. Cancer* 93:709-718, Cancer Research UK, England (2005).

Huang, E.Y., et al., "Surface Expression of Notch1 on Thymocytes: Correlation with the Double-Negative to Double-Positive Transition," *J. Immunol.* 171:2296-2304, The American Association of Immunologists, Inc., United States (2003).

International Search Report for International Application No. PCT/US11/21135, ISA/US, Alexandria, Virginia, USA, mailed on Jul. 20, 2011.

Maillard, I., et al., "Mastermind critically regulates Notch-mediated lymphoid cell fate decisions," *Blood* 104:1696-1702, The American Society of Hematology, United States (2004).

Qin, J.-Z., et al., "p53-independent NOXA induction overcomes resistance of malignant melanomas," *Mol. Cancer Ther.* 3:895-902, American Association for Cancer Research, United States (2004).

"Notch 2 (25-255): sc-5545 datasheet," Santa Cruz Biotechnology, Inc., downloaded on Dec. 2, 2009, 1 page.

NCBI Entrez, GenBank Report, Accession No. P01724, Burstein, Y. and Schechter, I., Entry Date Jul. 21, 1986, last updated Nov. 4, 2008.

NCBI Entrez, GenBank Report, Accession No. Q8VDC9, Sembi, P., Entry Date Mar. 1, 2002, last updated Oct. 31, 2006.

Written Opinion of the International Searching Authority for International Application No. PCT/US11/21135, ISA/US, Alexandria, Virginia, USA, mailed on Jul. 20, 2011.

Rand, M., et al., "Calcium binding to tandem repeats of EGF-like modules. Expression and characterization of the EGF-like modules of human Notch-1 implicated in receptor-ligand interactions," *Protein Science* 6:2059-2071, The Protein Society, United States (1997).

Liu, H., et al., "Notch3 is critical for proper angiogenesis and mural cell investment," *Circ. Res.* 107:860-70, American Heart Association, United States (2010).

Bolos, V., et al., "Notch Signaling in Development and Cancer," *Endocrine Reviews* 28(3):339-363, The Endocrine Society, United States (2007).

Miele, L., et al., "NOTCH Signaling as a Novel Cancer Therapeutic Target," *Curr. Cancer Drug Targets* 6(4):313-323, Bentham Science Publishers, Ltd., Netherlands (2006).

Tanaka, M., et al., "Asymmetric localization of Notch2 on the microvillous surface in choroid plexus epithelial cells," *Histochem. Cell Biol.* 127(4):449-56, Epub Jan. 12, 2007, Springer Verlag, Germany (2007).

Jurynczyk, M., et al., "Notch3 inhibition in myelin-reactive T cells down-regulates protein kinase C theta and attenuates experimental autoimmune encephalomyelitis," *J. Immunology*, 180(4):2634-40, The American Association of Immunologists Inc., United States (2008).

Bendig, M., "Humanization of rodent monoclonal antibodies by CDR grafting," in *METHODS: A companion to Methods in Enzymology*, vol. 8., pp. 83-93 (1995).

Colman, P. M., "Effects of amino acid sequence changes on antibody-antigen interactions," *Res Immunol.* 145(1):33-6, Elsevier, France (1994).

Greenspan, N. S. and Di Cera, E., "Defining epitopes: It's not as easy as it seems," *Nat. Biotechnol.* 17(10):936-7, Nature America Publishing (1999).

Panka, D.J., et al., "Variable region framework differences result in decreased or increased affinity of variant anti-digoxin antibodies," *Proc Natl Acad Sci U S A.* 85(9):3080-4, National Academy of Sciences, United States (1988).

Paul, W.E., "Chapter 8: Immunogenicity and Antigen Structure," in *Fundamental Immunology*, Third Edition, p. 242, Raven Press, United States (1993).

Ahmad, I. et al., "Involvement of Notch-1 in mammalian retinal neurogenesis: association of Notch-1 activity with both immature and terminally differentiated cells," *Mech. Dev.* 53(1):73-85, Elsevier Scientific Publishers, Ireland (1995).

Houde, C., et al., "Overexpression of the NOTCH ligand JAG2 in malignant plasma cells from multiple myeloma patients and cell lines," *Blood* 104(12):3697-704, American Society of Hematology, United States (2004).

(56) References Cited

OTHER PUBLICATIONS

Shawber, C., et al., "Notch signaling inhibits muscle cell differentiation through a CBF1-independent pathway," *Development* 122(12):3765-73, Company of Biologists Limited, England (1996).
"4G1" Notch1 monoclonal antibody; Abnova technical datasheet, accessed at www.abnova.com/products/products_details.asp?Catalog_id=1-100004851-M10, accessed on Nov. 9, 2012; 8 total pages.
Brorson, K., et al., "Mutational analysis of avidity and fine specificity of anti-levan antibodies," *J. Immunol.* 163(12):6694-701, American Association of Immunologists, United States (1999).
Brummell, D.A., et al., "Probing the combining site of an anti-carbohydrate antibody by saturation-mutagenesis: role of the heavy-chain CDR3 residues," *Biochemistry* 32(4):1180-7, American Chemical Society, United States (1993).
Kobayashi, H., et al., "Tryptophan H33 plays an important role in pyrimidine (6-4) pyrimidone photoproduct binding by a high-affinity antibody," *Protein Eng.* 12(10):879-84, Oxford University Press, England (1999).
Burks, E.A. et al., "In vitro scanning saturation mutagenesis of an antibody binding pocket," *Proc Natl Acad Sci U S A.* 94(2):412-7, National Academy of Sciences, United States (1997).
Jang, Y.J., et al., "The structural basis for DNA binding by an anti-DNA autoantibody," *Mol. Immunol.* 35(18):1207-17, Pergamon Press, England (1998).
McDaniell, R., et al., "*NOTCH2* Mutations Cause Alagille Syndrome, a Heterogeneous Disorder of the Notch Signaling Pathway," *Am. J. Hum. Genet.*79(1):169-73, University of Chicago Press, United States (2006).
Nickoloff, B.J., et al., "Notch signaling as a therapeutic target in cancer: a new approach to the development of cell fate modifying agents," *Oncogene* 22(42):6598-608, Nature Publishing Group, England (2003).
Varnum-Finney, B. et al., "The Notch ligand, Jagged-1, influences the development of primitive hematopoietic precursor cells." *Blood* 91(11):4084-91, The American Society of Hematology, United States (1998).
Jundt, F., et al., "Jagged1-induced Notch signaling drives proliferation of multiple myeloma cells," *Blood* 103:3511-3515, The American Society of Hematology, United States (May 2004).
Wu, Y., "Therapeutic antibody targeting of individual Notch receptors," *Nature* 464:1052-1057, Nature Publishing Group, England (2010).
Siebel, C.W., "PL07-04 Notch Antibody Antagonists for Cancer Therapy," Invited Abstracts (Plenary Session), Abstract nr PL07-04, American Association for Cancer Research, United States (Oct. 2007).
Gordon, W.R., et al., "Structural basis for autoinhibition of Notch," *Nat. Struct. Mol. Biol.* 14(4):295-300, Nature Pub. Group, United States (Apr. 2007).
Sanchez-Irizarry, C., "Notch Subunit Heterodimerization and Prevention of Ligand-Independent Proteolytic Activation Depend, Respectively, on a Novel Domain and the LNR Repeats," *Mol. Cell Biol.* 24(21):9265-9273, American Society for Microbiology, United States (2004).
Roy, M., et al., "The multifaced role of Notch in cancer," *Curr. Opin. Genet. Dev.* 17(1):52-59, Elsevier, England (2007, available online Dec. 2006).
Supplemental Data for Li, K., et al., "Modulation of Notch Signaling by Antibodies Specific for the Extracellular Negative Regulatory Region of NOTCH3," *J. Biol. Chem.* 283:8046-8054, The American Society for Biochemistry and Molecular Biology, Inc., United States (Mar. 2008).
NCBI Entrez, GenBank Report, Accession No. AAA39140, Pennell, C.A., et al., Entry Date Apr. 27, 1993, accessed on Jun. 3, 2013.
Aste-Amezaga, M., et al., "Characterization of Notch1 Antibodies That Inhibit Signaling of Both Normal and Mutated Notch1 Receptors," *PLoS ONE* 5(2):1-13, Public Library of Science, United States (2010).

Supplementary European Search Report for European Patent Application No. EP 11 73 3378, issued Apr. 17, 2013, The Hague.
Real, P.J. and Ferrando, A.A., "NOTCH inhibition and glucocoritcoid therapy in T-cell acute lymphoblastic leukemia," *Leukemia*23:1374-1377, Macmillan Publishers Limited, United States (2009).
Sriuranpong, V., et al., "Notch signalling induces cell cycle arrest in small cell lung cancer cells," *Cancer Res.* 61(7):3200-3205, American Association for Cancer Research, United States (2001).
Rudikoff, S., et al., "Single amino acid substitution altering antigen-binding specificity," *Proc. Natl. Acad. Sci. USA.* 79(6):1979-1983, National Academy of Sciences, United States (1982).
MacCallum, R.M., et al., "Antibody-antigen interactions: contact analysis and binding site topography," *J Mol. Biol.* 262(5):732-745, Academic Press, England (1996).
De Pascalis, R., et al., "Grafting of "abbreviated" complementarity-determining regions containing specificity-determining residues essential for ligand contact to engineer a less immunogenic humanized monoclonal antibody," J. *Immunol.* 169(6):3076-84, American Association of Immunologists, United States (2002).
Casset, F., et al., "A peptide mimetic of an anti-CD4 monoclonal antibody by rational design," *Biochem Biophys Res Commun.* 307(1):198-205, Elsevier Science USA, (2003).
Vajdos, F.F., et al., "Comprehensive functional maps of the antigen-binding site of an anti-ErbB2 antibody obtained with shotgun scanning mutagenesis," *J. Mol. Biol* 320(2):415-28, Academic Press, England (2002).
Holm, P., et al., "Functional mapping and single chain construction of the anti-cytokeratin 8 monoclonal antibody TS1," *Mol. Immunol.* 44(6):1075-84, Pergamon Press, England (2007) Epub Sep. 20, 2006.
Chen, Y., et al., "Selection and analysis of an optimized anti-VEGF antibody: crystal structure of an affinity-matured Fab in complex with antigen," *J. Mol. Biol.* 293(4):865-81, Academic Press, England (1999).
Wu, H., et al., "Humanization of a murine monoclonal antibody by simultaneous optimization of framework and CDR residues," *J. Mol. Biol.* 294(1):151-62, Academic Press, England (1999).
Talora, C., et al., "Specific down-modulation of Notch1 signaling in cervical cancer cells is required for sustained HPV-E6/E7 expression and late steps of malignant transformation," *Genes Dev.* 16(17):2252-63, Cold Spring Harbor Laboratory Press, United States (2002).
Riechmann, L. et al., "Reshaping human antibodies for therapy," *Nature* 332:323-327, Nature Publishing Group, United Kingdom (1988).
International Search Report for International Application No. PCT/US2013/041279, US Patent Office, mailed on Oct. 24, 2013.
Al-Lazikani, B., et al., "Standard Conformations for the Canonical Structures of Immunoglobulins," *J. Mol. Biol.* 273: 927-948, Academic Press Limited, United States (1997).
Brennan, M., et al., "Preparation of Bispecific Antibodies by Chemical Recombination of Monoclonal Immunoglobulin G1 Fragments," *Science* 229 (4708): 81-83, American Association for the Advancement of Science, United States (1985).
Clackson, T., et al., "Making antibody fragments using phage display libraries," *Letters to Nature* 352: 624-627, Macmillan Magazines, Ltd., United Kingdom (1991).
Gruber, M., et al., "Efficient Tumor Cell Lysis Mediated by a Bispecific Single Chain Antibody Expressed in *Escherichia coli,*" *Journal of Immunology* 152 (11): 5368-5374, The American Association of Immunologists, United States (1994).
Hoogenboom, H., et al., "By-passing Immunisation: Human Antibodies from Synthetic Repertoires of Germline $V_H$ Gene Segments Rearranged in Vitro," *J. Mol. Biol.* 227: 381-388, Academic Press Limited, United States (1992).
Hosse, R., et al., "A new generation of protein display scaffolds for molecular recognition," *Protein Science* 15: 14-27, Cold Spring Harbor Laboratory Press, United States (Jan. 2006).
Huse, W., et al., "Generation of a Large Combinatorial Library of the Immunoglobulin Repertoire in Phage Lambda," *Science* 246 (4935): 1275-1281, American Association for the Advancement of Science, United States (1989).
Jemal, A., et al., "Cancer Statistics, 2010" CA Cancer J. Clin., 60: 277-300, American Cancer Society, Inc., United States (2010).

(56) References Cited

OTHER PUBLICATIONS

Köhler, G., et al., "Continuous cultures of fused cells secreting antibody of predefined specificity," *Nature* 256: 495-497, Macmillan Journals Ltd., United Kingdom (1975).

Kostelny, S.A., et al.,"Formation of a Bispecific Antibody by the Use of Leucine Zippers," *The Journal of Immunology* 148: 1547-1553, The American Association of Immunologists, United States (1992).

Marks, J.D., et al., "By-passing Immunization: Human Antibodies from V-gene Libraries Displayed on Phage," *J. Mol. Biol.* 222: 581-597, Academic Press Limited, United States (1991).

Marks, J.D., et al., "By-passing Immunization: Building High Affinity Human Antibodies by Chain Shuffling," *Bio/Technology* 10: 779-783, Macmillan Journals Ltd., United States (1992).

McCafferty, J., et al., "Phage antibodies: filamentous phage displaying antibody variable domains," *Nature* 348 (6301): 552-554, Macmillan Magazines Ltd, London (1990).

Milstein, C., et al., "Hybrid hybridomas and their use in immunohistochemistry," *Nature* 305: 537-540, Macmillan Journals Ltd., London (1983).

Shalaby, M.R., et al., "Development of Humanized Bispecific Antibodies Reactive with Cytotoxic Lymphocytes and Tumor Cells Overexpressing the HER2 Protooncogene," *J. Exp. Med.* 175: 217-225, The Rockefeller University Press, United States (1992).

Sheets, M.D., et al., "Efficient construction of a large nonimmune phage antibody library: The production of high-affinity human single-chain antibodies to protein antigens," *Proc. Natl. Acad. Sci.* 95: 6157-6162, The National Academy of Sciences, United States (1998).

Suresh, M.R., et al., "Bispecific Monoclonal Antibodies from Hybrid Hybridomas," *Methods in Enzymology* 121: 210-228, Academic Press, Inc., United States (1986).

Tutt, A., et al.,"Trispecific F(ab')$_3$ Derivatives that use Cooperative Signaling Via the TCR/CD3 Complex and CD2 to Activate and Redirect Resting Cytotoxic T Cells," *The Journal of Immunology* 147: 60-69, The American Association of Immunologists, United States (1991).

Vaughan, T.J., et al., "Human Antibodies with Sub-nanomolar Affinities Isolated from a Large Non-immunized Phage Display Library," *Nature Biotechnology* 14: 309-314, Nature America, Inc., United States (1996).

Thermo Fisher Scientific: Notch1 Antibody (A6), Product Data Sheet, commercially available 2004, http://www.pierce-antibodies.com/products/printProductDetail/printProductDetails.cfm?js=1&format=extended&catnbr=MA1-91405.

\* cited by examiner

FIG. 1B

MUTAGENESIS OF NOTCH1 RECEPTOR GLUTAMATE 424 TO
GLUTAMINE SIGNIFICANTLY REDUCES LIGAND BINDING
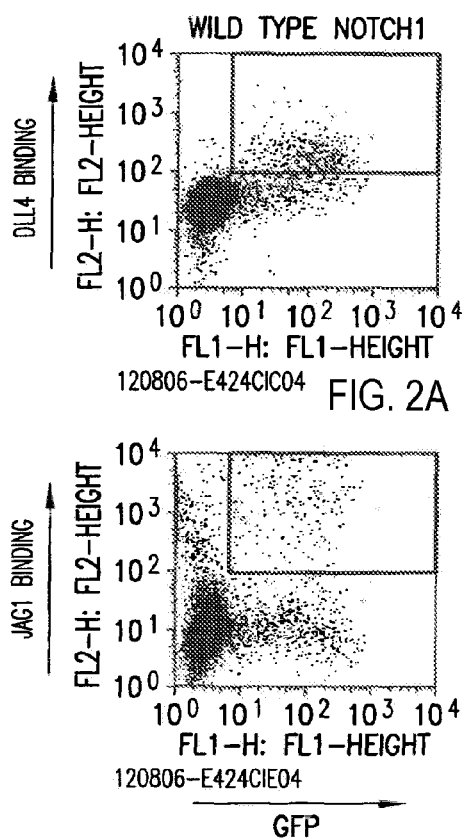
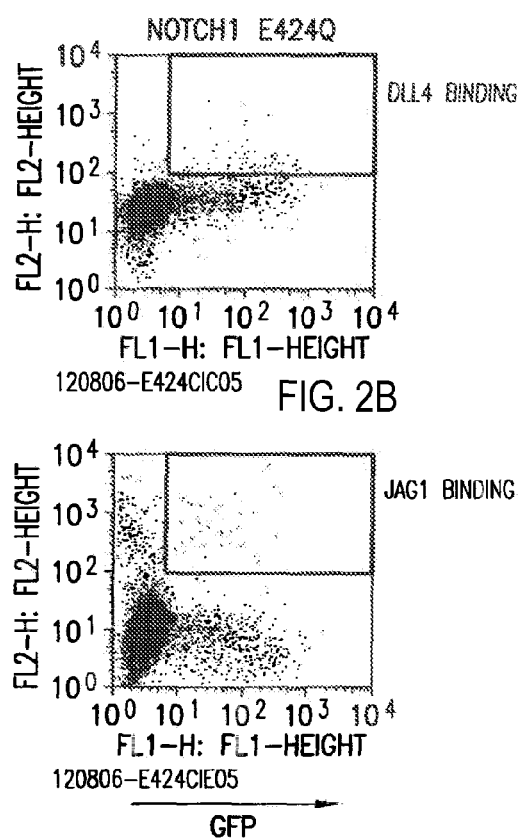
FIG. 2A
FIG. 2B
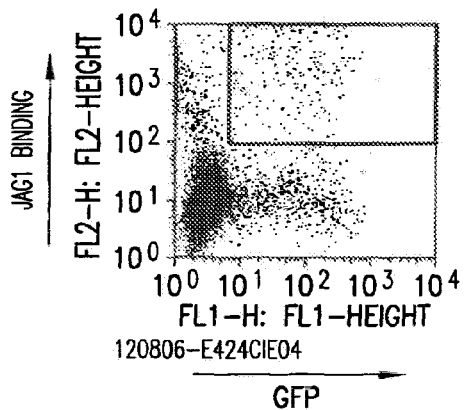
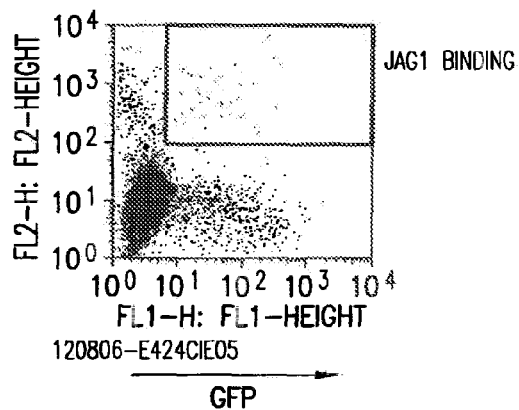
FIG. 2C
FIG. 2D MUTAGENESIS OF NOTCH2 RECEPTOR GLUTAMATE 428 TO
GLUTAMINE SIGNIFICANTLY REDUCES LIGAND BINDING

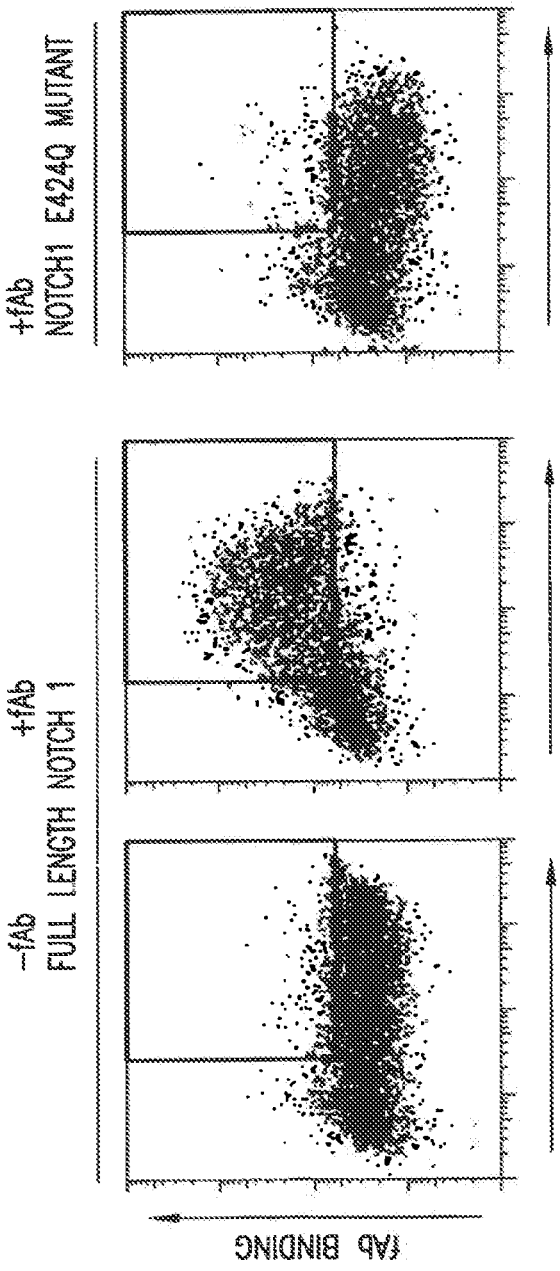

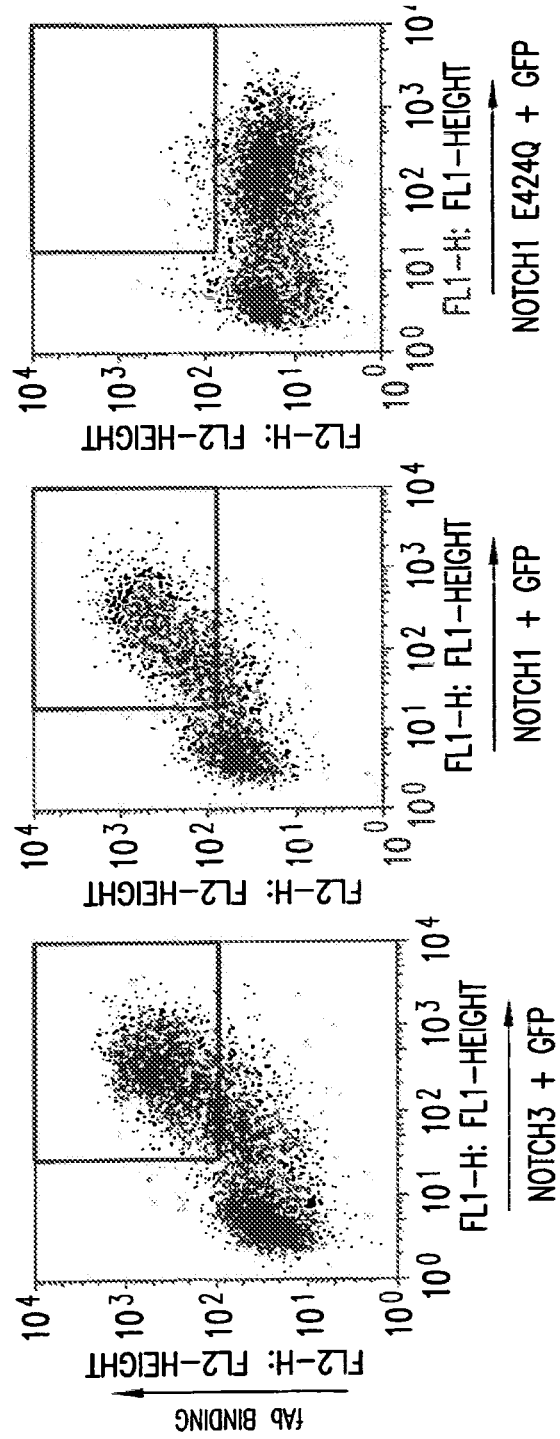

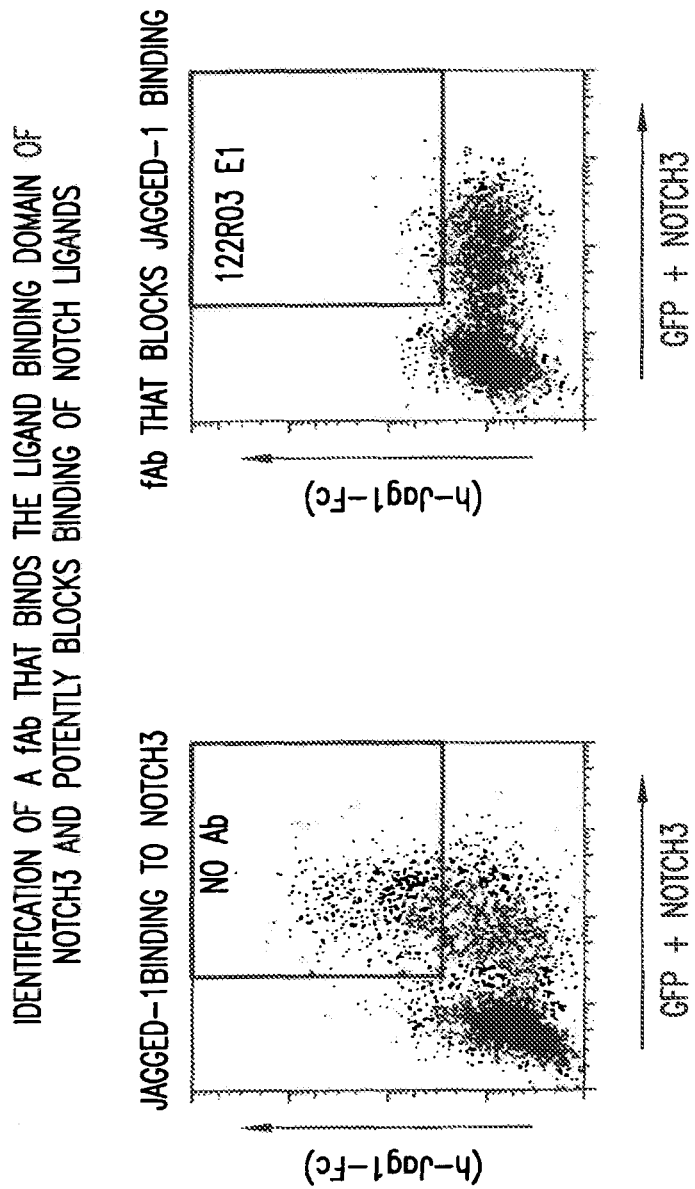

CONTROL Ab + PACLITAXEL vs. 90R21 + PACLITAXEL: P = 0.015

ANTIBODIES THAT BIND THE GLUTAMATE LIGAND BINDING REGION OF NOTCH3

CROSS REFERENCE TO RELATED APPLICATIONS

This application is a divisional of U.S. application Ser. No. 13/308,224, filed Nov. 30, 2011; which is a divisional of U.S. application Ser. No. 12/010,421, filed Jan. 24, 2008, now U.S. Pat. No. 8,088,617; which claims the benefit of U.S. Provisional Application No. 60/886,414, filed Jan. 24, 2007, all of which are herein incorporated by reference.

REFERENCE TO A SEQUENCE LISTING SUBMITTED ELECTRONICALLY VIA EFS-WEB

The content of the electronically submitted sequence listing (Name: sequencelisting_ascii.txt, Size: 37 kilobytes; and Date of Creation: Sep. 22, 2011) is herein incorporated by reference in its entirety.

BACKGROUND OF THE INVENTION

1. Field of the Invention

The present invention relates to the field of oncology and provides novel compositions and methods for diagnosing and treating cancer. The present invention provides antibodies against a cancer stem cell marker for the diagnosis and treatment of solid tumors.

2. Background Art

Cancer is one of the leading causes of death in the developed world, with over one million people diagnosed with cancer and 500,000 deaths per year in the United States alone. Overall it is estimated that more than 1 in 3 people will develop some form of cancer during their lifetime. There are more than 200 different types of cancer, four of which—breast, lung, colorectal, and prostate—account for over half of all new cases (Jemal et al., 2003, Cancer J. Clin. 53:5-26).

Breast cancer is the most common cancer in women, with an estimated 12% of women at risk of developing the disease during their lifetime. Although mortality rates have decreased due to earlier detection and improved treatments, breast cancer remains a leading cause of death in middle-aged women, and metastatic breast cancer is still an incurable disease. On presentation, most patients with metastatic breast cancer have only one or two organ systems affected, but as the disease progresses, multiple sites usually become involved. The most common sites of metastatic involvement are locoregional recurrences in the skin and soft tissues of the chest wall, as well as in axilla and supraclavicular areas. The most common site for distant metastasis is the bone (30-40% of distant metastasis), followed by the lungs and liver. And although only approximately 1-5% of women with newly diagnosed breast cancer have distant metastasis at the time of diagnosis, approximately 50% of patients with local disease eventually relapse with metastasis within five years. At present the median survival from the manifestation of distant metastases is about three years.

Current methods of diagnosing and staging breast cancer include the tumor-node-metastasis (TNM) system that relies on tumor size, tumor presence in lymph nodes, and the presence of distant metastases (American Joint Committee on Cancer: AJCC Cancer Staging Manual. Philadelphia, Pa.: Lippincott-Raven Publishers, 5th ed., 1997, pp 171-180; Harris, J R: "Staging of breast carcinoma" in Harris, J. R., Hellman, S., Henderson, I. C., Kinne D. W. (eds.): Breast Diseases. Philadelphia, Lippincott, 1991). These parameters are used to provide a prognosis and select an appropriate therapy. The morphologic appearance of the tumor can also be assessed but because tumors with similar histopathologic appearance can exhibit significant clinical variability, this approach has serious limitations. Finally assays for cell surface markers can be used to divide certain tumors types into subclasses. For example, one factor considered in the prognosis and treatment of breast cancer is the presence of the estrogen receptor (ER) as ER-positive breast cancers typically respond more readily to hormonal therapies such as tamoxifen or aromatase inhibitors than ER-negative tumors. Yet these analyses, though useful, are only partially predictive of the clinical behavior of breast tumors, and there is much phenotypic diversity present in breast cancers that current diagnostic tools fail to detect and current therapies fail to treat.

Prostate cancer is the most common cancer in men in the developed world, representing an estimated 33% of all new cancer cases in the U.S., and is the second most frequent cause of death (Jemal et al., 2003, CA Cancer J. Clin. 53:5-26). Since the introduction of the prostate specific antigen (PSA) blood test, early detection of prostate cancer has dramatically improved survival rates; the five year survival rate for patients with local and regional stage prostate cancers at the time of diagnosis is nearing 100%. Yet more than 50% of patients will eventually develop locally advanced or metastatic disease (Muthuramalingam et al., 2004, Clin. Oncol. 16:505-16).

Currently radical prostatectomy and radiation therapy provide curative treatment for the majority of localized prostate tumors. However, therapeutic options are very limited for advanced cases. For metastatic disease, androgen ablation with luteinising hormone-releasing hormone (LHRH) agonist alone or in combination with anti-androgens is the standard treatment. Yet despite maximal androgen blockage, the disease nearly always progresses with the majority developing androgen-independent disease. At present there is no uniformly accepted treatment for hormone refractory prostate cancer, and chemotherapeutic regimes are commonly used (Muthuramalingam et al., 2004, Clin. Oncol. 16:505-16; Trojan et al., 2005, Anticancer Res. 25:551-61).

Colorectal cancer is the third most common cancer and the fourth most frequent cause of cancer deaths worldwide (Weitz et al., 2005, Lancet 365:153-65). Approximately 5-10% of all colorectal cancers are hereditary with one of the main forms being familial adenomatous polyposis (FAP), an autosomal dominant disease in which about 80% of affected individuals contain a germline mutation in the adenomatous polyposis coli (APC) gene. Colorectal carcinomas invade locally by circumferential growth and elsewhere by lymphatic, hematogenous, transperitoneal, and perineural spread. The most common site of extralymphatic involvement is the liver, with the lungs the most frequently affected extra-abdominal organ. Other sites of hematogenous spread include the bones, kidneys, adrenal glands, and brain.

The current staging system for colorectal cancer is based on the degree of tumor penetration through the bowel wall and the presence or absence of nodal involvement. This staging system is defined by three major Duke's classifications: Duke's A disease is confined to submucosa layers of colon or rectum; Duke's B disease has tumors that invade through the muscularis propria and may penetrate the wall of the colon or rectum; and Duke's C disease includes any degree of bowel wall invasion with regional lymph node metastasis. While surgical resection is highly effective for early stage colorectal cancers, providing cure rates of 95% in Duke's A patients, the rate is reduced to 75% in Duke's B patients and the presence of positive lymph node in Duke's C disease predicts a 60% likelihood of recurrence within five years. Treatment of Duke's C patients with a post surgical course of chemotherapy reduces the recurrence rate to 40%-50% and is now the standard of care for these patients.

Lung cancer is the most common cancer worldwide, the third most commonly diagnosed cancer in the United States, and by far the most frequent cause of cancer deaths (Spiro et al., 2002, *Am. J. Respir. Crit. Care Med.* 166:1166-96; Jemal et al., 2003, *CA Cancer J. Clin.* 53:5-26). Cigarette smoking is believed responsible for an estimated 87% of all lung cancers making it the most deadly preventable disease. Lung cancer is divided into two major types that account for over 90% of all lung cancers: small cell lung cancer (SCLC) and non-small cell lung cancer (NSCLC). SCLC accounts for 15-20% of cases and is characterized by its origin in large central airways and histological composition of sheets of small cells with little cytoplasm. SCLC is more aggressive than NSCLC, growing rapidly and metastasizing early. NSCLC accounts for 80-85% of all cases and is further divided into three major subtypes based on histology: adenocarcinoma, squamous cell carcinoma (epidermoid carcinoma), and large cell undifferentiated carcinoma.

Lung cancer typically presents late in its course, and thus has a median survival of only 6-12 months after diagnosis and an overall 5 year survival rate of only 5-10%. Although surgery offers the best chance of a cure, only a small fraction of lung cancer patients are eligible with the majority relying on chemotherapy and radiotherapy. Despite attempts to manipulate the timing and dose intensity of these therapies, survival rates have increased little over the last 15 years (Spiro et al., 2002, *Am. J. Respir. Crit. Care Med.* 166:1166-96).

These four cancers, as well as many others, present as solid tumors that are composed of heterogeneous cell populations. For example, breast cancers are a mixture of cancer cells and normal cells, including mesenchymal (stromal) cells, inflammatory cells, and endothelial cells. Several models of cancer provide different explanations for the presence of this heterogeneity. One model, the classic model of cancer, holds that phenotypically distinct cancer cell populations all have the capacity to proliferate and give rise to a new tumor. In the classical model, tumor cell heterogeneity results from environmental factors as well as ongoing mutations within cancer cells resulting in a diverse population of tumorigenic cells. This model rests on the idea that all populations of tumor cells have some degree of tumorigenic potential. (Pandis et al., 1998, *Genes, Chromosomes & Cancer* 12:122-129; Kuukasjrvi et al., 1997, *Cancer Res.* 57:1597-1604; Bonsing et al., 1993, *Cancer* 71:382-391; Bonsing et al., 2000, *Genes Chromosomes & Cancer* 82: 173-183; Beerman H et al., 1991, *Cytometry* 12:147-54; Aubele M & Werner M, 1999, *Analyt. Cell. Path.* 19:53; Shen L et al., 2000, *Cancer Res.* 60:3884).

An alternative model for the observed solid tumor cell heterogeneity derives from the impact of stem cells on tumor development. According to this model, cancer arises from dysregulation of the mechanisms that control normal tissue development and maintenance. (Beachy et al., 2004, *Nature* 432:324). During normal animal development, cells of most or all tissues are derived from normal precursors, called stem cells (Morrison et al., 1997, *Cell* 88:287-98; Morrison et al., 1997, *Curr. Opin. Immunol.* 9:216-21; Morrison et al., 1995, *Annu. Rev. Cell. Dev. Biol.* 11:35-71). Stem cells are cells that: (1) have extensive proliferative capacity; 2) are capable of asymmetric cell division to generate one or more kinds of progeny with reduced proliferative and/or developmental potential; and (3) are capable of symmetric cell divisions for self-renewal or self-maintenance. The best-studied example of adult cell renewal by the differentiation of stem cells is the hematopoietic system where developmentally immature precursors (hematopoietic stem and progenitor cells) respond to molecular signals to form the varied blood and lymphoid cell types. Other cells, including cells of the gut, breast ductal system, and skin are constantly replenished from a small population of stem cells in each tissue, and recent studies suggest that most other adult tissues also harbor stem cells, including the brain. Tumors derived from a "solid tumor stem cell" (or "cancer stem cell" from a solid tumor) subsequently undergo chaotic development through both symmetric and asymmetric rounds of cell divisions. In this stem cell model, solid tumors contain a distinct and limited (possibly even rare) subset of cells that share the properties of normal "stem cells", in that they extensively proliferate and efficiently give rise both to additional solid tumor stem cells (self-renewal) and to the majority of tumor cells of a solid tumor that lack tumorigenic potential. Indeed, mutations within a long-lived stem cell population may initiate the formation of cancer stem cells that underlie the growth and maintenance of tumors and whose presence contributes to the failure of current therapeutic approaches.

The stem cell nature of cancer was first revealed in the blood cancer, acute myeloid leukemia (AML) (Lapidot et al., 1994, *Nature* 17:645-8). More recently, it has been demonstrated that malignant human breast tumors similarly harbor a small, distinct population of cancer stem cells enriched for the ability to form tumors in immunodeficient mice. An ESA+, CD44+, CD24−/low, Lin− cell population was found to be 50-fold enriched for tumorigenic cells compared to unfractionated tumor cells (Al-Hajj et al., 2003, *Proc. Nat'l Acad. Sci.* 100:3983-8). The ability to prospectively isolate the tumorigenic cancer cells has permitted investigation of critical biological pathways that underlie tumorigenicity in these cells, and thus promises the development of better diagnostic assays and therapeutics for cancer patients. It is toward this purpose that this invention is directed.

BRIEF SUMMARY OF THE INVENTION

The present invention for the first time identifies a conserved ligand binding region within the ligand binding domain of the Notch family of receptors. Specifically, the ligand binding region encompasses a conserved glutamate within EGF11 of Notch1, Notch2, and Notch4 and EGF10 of Notch3 that is necessary for ligand binding, and this invention provides molecules, as well as methods for generating molecules, that specifically interact with this ligand binding region. In certain embodiments, the present invention provides an antagonist that specifically binds to the ligand binding region of at least one Notch receptor. In certain embodiments, the antagonist is an antibody.

In certain embodiments, the present invention provides an isolated antibody that specifically binds to a glutamate ligand binding region of at least one human Notch receptor. In certain embodiments, the antibody is an antagonist of Notch signaling. In certain embodiments the antibody blocks ligand binding. In certain embodiments, the antibody is a monoclonal antibody. In certain embodiments, the antibody is a chimeric antibody. In certain embodiments, the antibody is a humanized antibody. In certain embodiments, the antibody is a human antibody. In certain embodiments, the antibody is an antibody fragment. In certain embodiments, the present invention provides a pharmaceutical composition comprising an antibody that specifically binds to a glutamate ligand binding region of at least one human Notch receptor.

In certain embodiments, the present invention provides an isolated antibody that specifically binds to a glutamate ligand binding region of human Notch1 receptor. In certain embodiments, the antibody binds to an epitope within amino acids 422-432 (amino acids PCEHAGKCINT; SEQ ID NO: 21) of the human Notch1 receptor. In certain embodiments, the antibody specifically binds to amino acids 424-425 (amino acids EH; residues 3 and 4 of SEQ ID NO: 21) of the human Notch1 receptor. In certain embodiments, the antibody specifically binds to amino acid 424 (amino acid E; residue 3 of SEQ ID NO: 21) of the human Notch1 receptor. In certain embodiments, the antibody comprises a heavy chain variable region comprising CDR amino acid sequences CDR1 (SEQ ID NO: 2); CDR2 (SEQ ID NO: 3); and CDR3 (SEQ ID NO: 4). In certain embodiments, the antibody further comprises a light chain variable region comprising CDR amino acid sequences CDR1 (SEQ ID NO: 6); CDR2 (SEQ ID NO: 7); and CDR3 (SEQ ID NO: 8). In certain embodiments, the antibody is 90R21 (deposited on Feb. 1, 2008 with American Type Culture Collection, Manassas, Va. 20108; ATCC deposit No. PTA-8909). In certain embodiments, the antibody competes for specific binding to a Notch glutamate ligand binding region with antibody 90R21 (ATCC deposit No. PTA-8909).

In certain embodiments, the present invention provides an isolated antibody that specifically binds to a glutamate ligand binding region of human Notch2 receptor. In certain embodiments, the antibody specifically binds to an epitope within amino acids 426-436 (amino acids PCEHAGKCVNT; SEQ ID NO: 22) of the human Notch2 receptor. In certain embodiments, the antibody specifically binds to amino acids 428-429 (amino acids EH; residues 3 and 4 of SEQ ID NO: 22) of the human Notch2 receptor. In certain embodiments, the antibody specifically binds to amino acid 428 (amino acid E; residue 3 of SEQ ID NO: 22) of the human Notch2 receptor.

In certain embodiments, the present invention provides an isolated antibody that specifically binds to a glutamate ligand binding region of human Notch3 receptor. In certain embodiments, the antibody specifically binds to an epitope within amino acids 401-411 (amino acids PCEHLGRCVNT; SEQ ID NO: 23) of the human Notch3 receptor. In certain embodiments, the antibody specifically binds to amino acids 403-404 (amino acids EH; residues 3 and 4 of SEQ ID NO: 23) of the human Notch3 receptor. In certain embodiments, the antibody specifically binds to amino acid 403 (amino acid E; residue 3 of SEQ ID NO: 23) of the human Notch3 receptor. In certain embodiments, the antibody comprises a heavy chain variable region comprising CDR amino acid sequences CDR1 (SEQ ID NO: 10); CDR2 (SEQ ID NO: 11); and CDR3 (SEQ ID NO: 12). In certain embodiments, the antibody further comprises a light chain variable region comprising CDR amino acid sequences CDR1 (SEQ ID NO: 14); CDR2 (SEQ ID NO: 15); and CDR3 (SEQ ID NO: 16). In certain embodiments, the antibody is 122R5 comprising the heavy chain variable region of SEQ ID NO: 9 and the light chain variable region of SEQ ID NO: 13. In certain embodiments, the antibody competes for specific binding to a Notch glutamate ligand binding region with antibody 122R5 (deposited on Feb. 1, 2008 with American Type Culture Collection, Manassas, Va. 20108; ATCC deposit No. PTA-8908).

In certain embodiments, the present invention provides an isolated antibody that specifically binds to a glutamate ligand binding region of human Notch4 receptor. In certain embodiments, the antibody specifically binds to an epitope within amino acids 445-455 (amino acids PCEHGGSCLNT; SEQ ID NO: 24) of the human Notch4 receptor. In certain embodiments, the antibody specifically binds to amino acids 447-448 (amino acids EH; residues 3 and 4 of SEQ ID NO: 24) of the human Notch4 receptor. In certain embodiments, the antibody specifically binds to amino acid 447 (amino acid E; residue 3 of SEQ ID NO: 24) of the human Notch4 receptor.

In certain embodiments, the present invention provides an isolated antibody that specifically binds to a glutamate ligand binding region of two or more human Notch receptors. In certain embodiments, the antibody is an antagonist of Notch signaling. In certain embodiments the antibody blocks ligand binding. In certain embodiments, the antibody is a monoclonal antibody. In certain embodiments, the antibody is a chimeric antibody. In certain embodiments, the antibody is a humanized antibody. In certain embodiments, the antibody is a human antibody. In certain embodiments, the antibody is an antibody fragment. In certain embodiments, the present invention provides a pharmaceutical composition comprising an antibody that specifically binds to a glutamate ligand binding region of two or more human Notch receptors.

The present invention also provides pharmaceutical compositions and articles of manufacture. In certain embodiments, the pharmaceutical composition comprises an antagonist of the present disclosure and a pharmaceutically acceptable vehicle. In certain embodiments, an article of manufacture comprises a container and a composition contained therein, wherein the composition comprises an antagonist or a pharmaceutical composition of the present disclosure. In certain embodiments, the article of manufacture further comprises a package inset indicating that the composition can be used to treat cancer. In certain embodiments, the package inset indicates that the composition can be used to treat cancer comprising cancer stem cells.

Further provided are methods of treating cancer in a subject. In certain embodiments, the method of treating cancer comprises administering a therapeutically effective amount of an antagonist of the present disclosure. Examples of solid tumors that can be treated using a therapeutic composition of the instant invention include, but are not limited to, sarcomas and carcinomas. In certain methods of the present invention, the cancer comprises breast cancer, colorectal cancer, lung cancer, pancreatic cancer, prostate cancer, liver cancer, ovarian cancer, head and neck cancer, skin cancer, brain cancer, or a blood cancer. In certain embodiments, the cancer comprises tumor stem cells.

In certain embodiments, the present invention provides a method of treating cancer comprising administering to a patient a therapeutically effective amount of an antibody that specifically binds to a glutamate ligand binding region of at least one human Notch receptor. In certain embodiments, the antibody is an antagonist of Notch signaling. In certain embodiments the antibody blocks ligand binding. In certain embodiments, the antibody is a monoclonal antibody. In certain embodiments, the antibody is a chimeric antibody. In certain embodiments, the antibody is a humanized antibody. In certain embodiments, the antibody is a human antibody. In certain embodiments, the antibody is an antibody fragment. In certain embodiments, the present invention provides a pharmaceutical composition comprising an antibody that specifically binds to a glutamate ligand binding region of at least one human Notch receptor. In certain embodiments, the antibody is conjugated to a cytotoxic moiety. In certain embodiments, the method further comprises administering at least one additional therapeutic agent appropriate for effecting combination therapy. In certain embodiments, the additional therapeutic agent is Paclitaxel. In certain embodiments, the cancer is breast cancer, colorectal cancer, lung cancer, pancreatic cancer, prostate cancer, or head and neck cancer.

Further provided are methods of generating antibodies against a glutamate ligand binding region of at least one human Notch receptor. In certain embodiments, the method of generating an antibody that specifically binds to a glutamate ligand binding region of at least one human Notch receptor comprises: a) immunizing a subject with a polypeptide that comprises a glutamate ligand binding region of a human Notch receptor and b) recovering an antibody from the subject which binds said polypeptide. In certain embodiments, the glutamate ligand binding region of the polypeptide comprises PCEHXGZCXNX (SEQ ID NO: 25) in which X is a non-polar, aliphatic amino acid residue and Z is a positively charged amino acid residue. In certain embodiments, the glutamate ligand binding region of the polypeptide comprises PCEHAGRCANT (SEQ ID NO: 26). In certain embodiments, the glutamate ligand binding region of the polypeptide comprises amino acids 422-432 (amino acids PCEHAGKCINT; SEQ ID NO: 21) of human Notch1. In certain embodiments, the glutamate ligand binding region of the polypeptide comprises amino acids 426-436 (amino acids PCEHAGKCVNT; SEQ ID NO: 22) of human Notch2. In certain embodiments the glutamate ligand binding region of the polypeptide comprises amino acids 401-411 (amino acids PCEHLGRCVNT; SEQ ID NO: 23) of human Notch3. In certain embodiments the glutamate ligand binding region of the polypeptide comprises amino acids 445-455 (amino acids PCEHGGSCLNT; SEQ ID NO: 24) of human Notch4. In certain embodiments, the subject is a rodent. In certain embodiments, the rodent is a mouse. In certain embodiments, the antibody generated is a monoclonal antibody. In certain embodiments, the antibody generated is a human antibody.

In certain embodiments, the method of generating an antibody that specifically binds to a glutamate ligand binding region of at least one human Notch receptor comprises: a) panning a phage library against a polypeptide comprising a glutamate ligand binding region of a human Notch receptor and b) isolating phage which bind said polypeptide. In certain embodiments the glutamate ligand binding region of the polypeptide comprises PCEHXGZCXNX (SEQ ID NO: 25) in which X is a non-polar, aliphatic amino acid residue and Z is a positively charged amino acid residue. In certain embodiments the glutamate ligand binding region of the polypeptide comprises PCEHAGRCANT (SEQ ID NO: 26). In certain embodiments the glutamate ligand binding region of the polypeptide comprises amino acids 422-432 (amino acids PCEHAGKCVNT; SEQ ID NO: 21) of human Notch1. In certain embodiments, the glutamate ligand binding region of the polypeptide comprises amino acids 426-436 (amino acids PCEHAGKCVNT; SEQ ID NO: 22) of human Notch2. In certain embodiments, the glutamate ligand binding region of the polypeptide comprises amino acids 401-411 (amino acids PCEHLGRCVNT; SEQ ID NO: 23) of human Notch3. In certain embodiments the glutamate ligand binding region of the polypeptide comprises amino acids 445-455 (amino acids PCEHGGSCLNT; SEQ ID NO: 24) of human Notch4. In certain embodiments, the antibody is a monoclonal antibody. In certain embodiments, the antibody is a chimeric antibody. In certain embodiments, the antibody is a humanized antibody. In certain embodiments, the antibody is a human antibody. In certain embodiments, the antibody is an antibody fragment.

In certain embodiments, the present invention provides isolated polynucleotides encoding the antibodies of the present invention. In certain embodiments, the polynucleotides encode a heavy chain variable region of an antibody that specifically binds to a glutamate ligand binding region of at least one human Notch receptor. In certain embodiments, the polynucleotides encode a light chain variable region of an antibody that specifically binds to a glutamate ligand binding region of at least one human Notch receptor.

BRIEF DESCRIPTION OF THE DRAWINGS/FIGURES

Figure 1B:
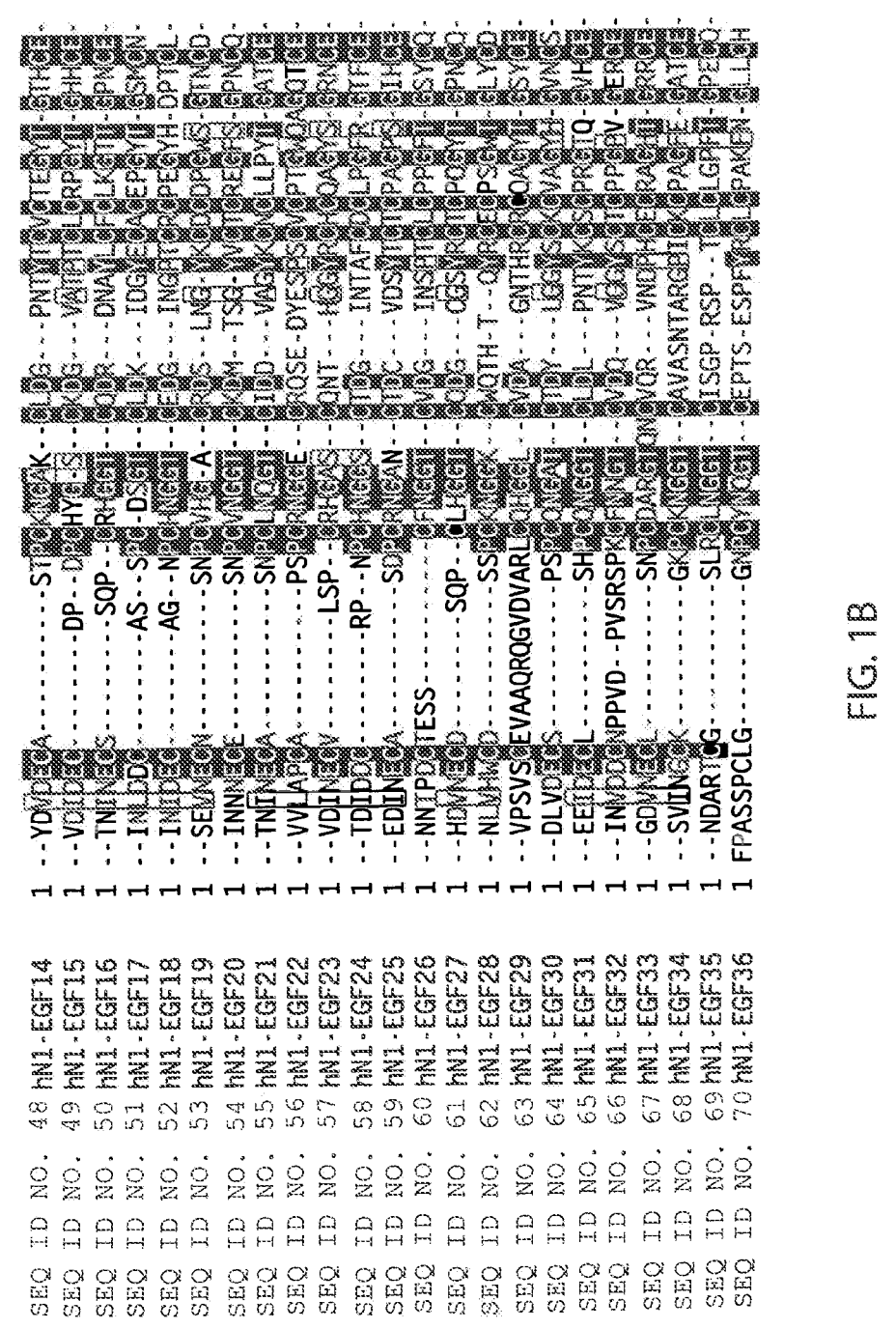

FIG. 1: (A) and (B) Alignment of Human Notch1 EGF Repeats and Selected EGF Repeats from Other Notch Proteins. All thirty-six EGF repeats from human Notch1 (hN1; SEQ ID NOs 29-39 and 46-70) are aligned along with EGF11 of human Notch2 (hN2; SEQ ID NO: 40), human Notch4 (hN4; SEQ ID NO: 42), Drosophila Notch (d-N1; SEQ ID NO: 44), and Xenopus Notch (xeN1; SEQ ID NO: 43); EGF10 of human Notch3 (the functional equivalent of Notch1 EGF11; SEQ ID NO: 41); and EGF9 of C. elegans Lin12 (ce_lin12; SEQ ID NO: 45). Conserved amino acid residues are highlighted in black. A glutamate residue (E) conserved across ligand binding regions is found only in EGF11 of human Notch1. An arrow (top) indicates the E position and brackets indicate the conserved ligand binding regions.

FIG. 2: (A), (B), (C) and (D) Mutagenesis of Notch1 Receptor Glutamate 424 to Glutamine Significantly Reduces Ligand Binding. FACS analysis of HEK 293 cells co-transfected with GFP and either wild type Notch1 or Notch1 E424Q binding to Jagged1 or DLL4 proteins. GFP expression marked cells expressing Notch1 protein α-axis) and binding to either DLL4 or Jagged1 protein is indicated along the y-axis. Cells expressing wild type Notch1 bound both DLL4 (A) and Jagged1 (C). In contrast, significantly fewer cells expressing Notch1 E424Q showed any binding to either DLL4 (B) or Jagged1 (D).

FIG. 3: (A), (B), (C) and (D) Mutagenesis of Notch2 Receptor Glutamate 428 to Glutamine Significantly Reduced Ligand Binding. FACS analysis of HEK 293 cells co-transfected with GFP and either wild type Notch2 or Notch2 E428Q binding to Jagged1 or DLL4 proteins. GFP expression marked cells expressing Notch2 protein α-axis) and binding to either DLL4 or Jagged1 protein is indicated along the y-axis. Cells expressing wild type Notch2 bound both DLL4 (A) and Jagged1 (C). In contrast, significantly fewer cells expressing Notch2 E428Q showed any binding to either DLL4 (B) or Jagged1 (D).

FIG. 4: (A), (B) and (C) Identification of a fAb that Binds a Critical Ligand Binding Domain of Notch1. FACS analysis of HEK 293 cells co-transfected with GFP and either wild type Notch or Notch1 E424Q using a human fAb identified by phage display as binding the ligand binding domain of Notch1. GFP expression marked cells expressing recombinant Notch1 protein α-axis) and binding to Notch1 is indicated along the y-axis. The fAb robustly binds to native human Notch1 (B), but does not bind to Notch1 containing the E424Q substitution in the ligand binding region (C). No binding was observed in the absence of the fAb (A).

FIG. 5: (A), (B) and (C) Identification of an Antibody that Binds the Ligand Binding Region of Multiple Notch Receptors. FACS analysis of HEK 293 cells co-transfected with GFP and wild type Notch3 (A), Notch1 (B) or Notch1 E424Q (C) using a human fAb identified by phage display as binding the ligand binding domain of Notch3. GFP expression marked transfected cells expressing recombinant Notch protein (x-axis). Binding of fAb is indicated on the y-axis.

Figure 6:
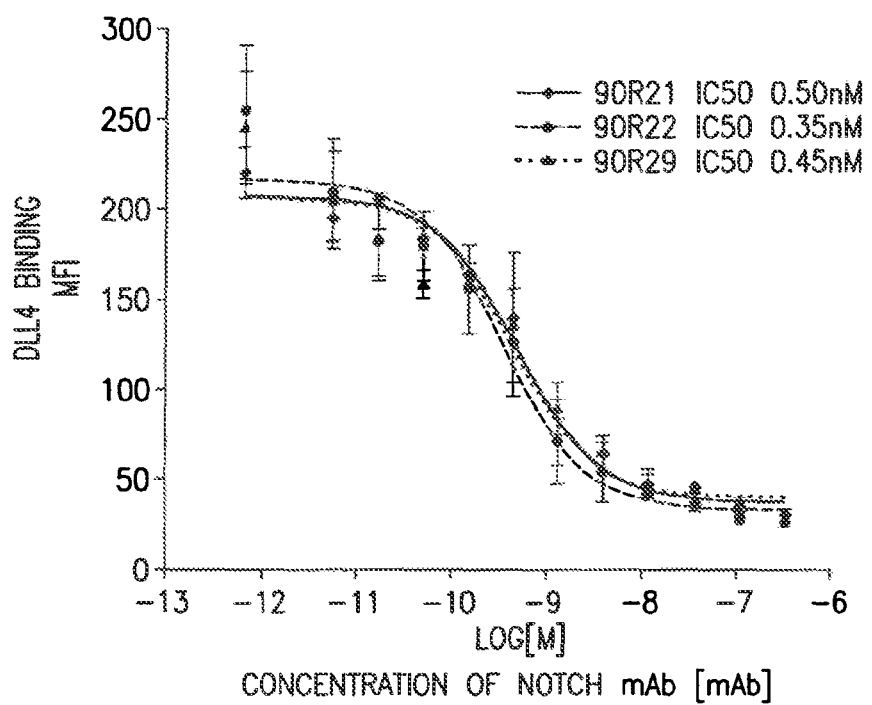

FIG. 6: Affinity Matured mAbs that Bind the Ligand Binding Domain of Notch1 Inhibit Binding of DLL4 to Notch1. FACS analysis demonstrated that various members of a series of affinity matured mAbs that bind the ligand binding domain of Notch1 potently block binding between DLL4 and Notch1.

Three affinity matured variants were tested for their ability to block binding between DLL4 and Notch1 (y-axis) in the presence of increasing concentrations of antibody (x-axis). 90R21 (black diamonds, solid line), 90R22 (black circles, dashed line) and 90M29 (black triangles, dotted line) all disrupted ligand binding.

FIG. 7: (A) and (B) Identification of a fAb that Binds the Ligand Binding Domain of Notch3 and Potently Blocks Binding of Notch Ligands. FACS analysis demonstrated the ability of a fAb that binds the Notch3 ligand binding domain as identified by phage display to block the binding of a Notch ligand (JAG1) to HEK 293 cells co-transfected with GFP and Notch3. GFP expression marked cells expressing recombinant Notch3 protein (x-axis) and binding between Notch3 and soluble human Jag 1 (h-Jag1-Fc) is indicated along the y-axis. Binding was only observed in the absence of antibody (A) and this binding was eliminated in the presence of the fAb (B).

FIG. 8: (A) and (B) Monoclonal Antibodies to the Notch Ligand Binding Domain Inhibit Notch Signaling. (A) A schematic of the Notch signaling mechanism. Upon ligand binding, gamma secretase activity cleaves the Notch receptor and liberates the intracellular domain (ICD) to activate downstream Notch signaling. (B) Monoclonal antibodies against the Notch ligand binding domain inhibit Notch signaling in response to Notch ligand DLL4. Western blot analysis of Notch ICD formation as indicative of Notch signaling confirmed that the presence of DLL4 induced robust formation of ICD (compare −DLL4 and +DLL4), and addition of a gamma secretase inhibitor (DBZ) blocked this signaling event. Antibodies to the ligand binding region of Notch (90R21, 90R22, and R9029) also inhibited ICD formation. In contrast, antibodies that bind Notch outside the ligand biding epitope (13M57) and non-binding antibodies (control mAb) have little or no affect on ICD formation.

FIG. 9: (A) and (B) Monoclonal Antibodies to the Notch Ligand Binding Domain Inhibit Tumor Growth In Vivo. NOD/SCID mice were injected with dissociated PE13 (A) or T3 (B) breast tumor cells and treated with either control antibodies (black squares); anti-Notch ligand binding region antibodies 90R21 (open circles); control antibodies in combination with Paclitaxel (black triangles); or 90R21 antibodies in combination with Paclitaxel (open triangles). Treatment with 90R21 antibodies reduced tumor growth significantly as compared to control antibody treated animals, while the combination with Paclitaxel virtually eliminated tumor growth.

DETAILED DESCRIPTION OF THE INVENTION

The term "antagonist" includes any molecule that partially or fully blocks, inhibits, or neutralizes a biological activity of the Notch pathway and such biological activity includes, but is not limited to, inhibition of tumor growth. Suitable antagonist molecules specifically include antagonist antibodies or antibody fragments, fragments or amino acid sequence variants of native Notch receptors.

The term "antibody" is used to mean an immunoglobulin molecule that recognizes and specifically binds to a target, such as a protein, polypeptide, peptide, carbohydrate, polynucleotide, lipid, or combinations of the foregoing through at least one antigen recognition site within the variable region of the immunoglobulin molecule. In certain embodiments, antibodies of the present invention include antagonist antibodies that specifically bind to a cancer stem cell marker protein and interfere with, for example, ligand binding, receptor dimerization, expression of a cancer stem cell marker protein, and/or downstream signaling of a cancer stem cell marker protein. In certain embodiments, disclosed antibodies include agonist antibodies that specifically bind to a cancer stem cell marker protein and promote, for example, ligand binding, receptor dimerization, and/or signaling by a cancer stem cell marker protein. In certain embodiments, disclosed antibodies do not interfere with or promote the biological activity of a cancer stem cell marker protein but inhibit tumor growth by, for example, antibody internalization and/or recognized by the immune system. As used herein, the term "antibody" encompasses intact polyclonal antibodies, intact monoclonal antibodies, antibody fragments (such as Fab, Fab', F(ab')2, and Fv fragments), single chain Fv (scFv) mutants, multispecific antibodies such as bispecific antibodies generated from at least two intact antibodies, chimeric antibodies, humanized antibodies, human antibodies, fusion proteins comprising an antigen determination portion of an antibody, and any other modified immunoglobulin molecule comprising an antigen recognition site so long as the antibodies exhibit the desired biological activity. An antibody can be of any the five major classes of immunoglobulins: IgA, IgD, IgE, IgG, and IgM, or subclasses (isotypes) thereof (e.g. IgG1, IgG2, IgG3, IgG4, IgA1 and IgA2), based on the identity of their heavy-chain constant domains referred to as alpha, delta, epsilon, gamma, and mu, respectively. The different classes of immunoglobulins have different and well known subunit structures and three-dimensional configurations. Antibodies can be naked or conjugated to other molecules such as toxins, radioisotopes, etc.

As used herein, the term "antibody fragment" refers to a portion of an intact antibody and refers to the antigenic determining variable regions of an intact antibody. Examples of antibody fragments include, but are not limited to Fab, Fab', F(ab')2, and Fv fragments, linear antibodies, single chain antibodies, and multispecific antibodies formed from antibody fragments.

An "Fv antibody" refers to the minimal antibody fragment that contains a complete antigen-recognition and -binding site either as two-chains, in which one heavy and one light chain variable domain form a non-covalent dimer, or as a single-chain (scFv), in which one heavy and one light chain variable domain are covalently linked by a flexible peptide linker so that the two chains associate in a similar dimeric structure. In this configuration the complementary determining regions (CDRs) of each variable domain interact to define the antigen-binding specificity of the Fv dimer. Alternatively a single variable domain (or half of an Fv) can be used to recognize and bind antigen, although generally with lower affinity.

A "monoclonal antibody" as used herein refers to homogenous antibody population involved in the highly specific recognition and binding of a single antigenic determinant, or epitope. This is in contrast to polyclonal antibodies that typically include different antibodies directed against different antigenic determinants. The term "monoclonal antibody" encompasses both intact and full-length monoclonal antibodies as well as antibody fragments (such as Fab, Fab', F(ab')2, Fv), single chain (scFv) mutants, fusion proteins comprising an antibody portion, and any other modified immunoglobulin molecule comprising an antigen recognition site. Furthermore, "monoclonal antibody" refers to such antibodies made in any number of manners including but not limited to by hybridoma, phage selection, recombinant expression, and transgenic animals.

As used herein, the term "humanized antibody" refers to forms of non-human (e.g. murine) antibodies that are specific immunoglobulin chains, chimeric immunoglobulins, or fragments thereof that contain minimal non-human sequences.

Typically, humanized antibodies are human immunoglobulins in which residues from the complementary determining region (CDR) are replaced by residues from the CDR of a non-human species (e.g. mouse, rat, rabbit, hamster) that have the desired specificity, affinity, and capability. In some instances, the Fv framework region (FR) residues of a human immunoglobulin are replaced with the corresponding residues in an antibody from a non-human species that has the desired specificity, affinity, and capability. The humanized antibody can be further modified by the substitution of additional residue either in the Fv framework region and/or within the replaced non-human residues to refine and optimize antibody specificity, affinity, and/or capability. In general, the humanized antibody will comprise substantially all of at least one, and typically two or three, variable domains containing all or substantially all of the CDR regions that correspond to the non-human immunoglobulin whereas all or substantially all of the FR regions are those of a human immunoglobulin consensus sequence. The humanized antibody can also comprise at least a portion of an immunoglobulin constant region or domain (Fc), typically that of a human immunoglobulin. Examples of methods used to generate humanized antibodies are described in U.S. Pat. No. 5,225,539.

The term "human antibody" as used herein means an antibody produced by a human or an antibody having an amino acid sequence corresponding to an antibody produced by a human made using any technique known in the art. This definition of a human antibody includes intact or full-length antibodies, fragments thereof, and/or antibodies comprising at least one human heavy and/or light chain polypeptide such as, for example, an antibody comprising murine light chain and human heavy chain polypeptides.

"Hybrid antibodies" are immunoglobulin molecules in which pairs of heavy and light chains from antibodies with different antigenic determinant regions are assembled together so that two different epitopes or two different antigens can be recognized and bound by the resulting tetramer.

The term "chimeric antibodies" refers to antibodies wherein the amino acid sequence of the immunoglobulin molecule is derived from two or more species. Typically, the variable region of both light and heavy chains corresponds to the variable region of antibodies derived from one species of mammals (e.g. mouse, rat, rabbit, etc) with the desired specificity, affinity, and capability while the constant regions are homologous to the sequences in antibodies derived from another (usually human) to avoid eliciting an immune response in that species.

The term "epitope" or "antigenic determinant" are used interchangeably herein and refer to that portion of an antigen capable of being recognized and specifically bound by a particular antibody. When the antigen is a polypeptide, epitopes can be formed both from contiguous amino acids and noncontiguous amino acids juxtaposed by tertiary folding of a protein. Epitopes formed from contiguous amino acids are typically retained upon protein denaturing, whereas epitopes formed by tertiary folding are typically lost upon protein denaturing. An epitope typically includes at least 3, and more usually, at least 5 or 8-10 amino acids in a unique spatial conformation.

The "ligand binding region", "glutamate ligand binding region", "Notch receptor ligand binding region", "Notch ligand binding region", "ligand binding domain" or grammatical variants thereof, refer to a region comprising the conserved glutamate within the EGF repeat of a ligand binding domain of at least one Notch receptor. In certain embodiments, the Notch ligand binding region comprises a conserved glutamate in an EGF11 of one or more of human Notch1, human Notch2, human Notch4, *drosophila* Notch, and *Xenopus* Notch or EGF 10 of human Notch3 critical for ligand-receptor interactions. In certain embodiments, a Notch ligand binding region comprises amino acids 422-432 (PCEHAGKCVNT; SEQ ID NO: 21) of human Notch1. In certain embodiments, a Notch ligand binding region comprises amino acids 424-425 (EH; residues 3 and 4 of SEQ ID NO: 21) of human Notch1. In certain embodiments, a Notch ligand binding region comprises amino acid 424 (E; residue 3 of SEQ ID NO: 21) of human Notch1. In certain embodiments, a Notch ligand binding region comprises amino acids 426-436 (PCEHAGKCVNT; SEQ ID NO: 22) of human Notch2. In certain embodiments, a Notch ligand binding region comprises amino acids 428-429 (EH; residues 3 and 4 of SEQ ID NO: 22) of human Notch2. In certain embodiments, a Notch ligand binding region comprises amino acid 428 (E; residue 3 of SEQ ID NO: 22) of human Notch2. In certain embodiments, a Notch ligand binding region comprises amino acids 401-411 (PCEHLGRCVNT; SEQ ID NO: 23) of human Notch3. In certain embodiments, a Notch ligand binding region comprises amino acids 403-404 (EH; residues 3 and 4 of SEQ ID NO: 23) of human Notch3. In certain embodiments, a Notch ligand binding region comprises amino acid 403 (E; residue 3 of SEQ ID NO: 23) of human Notch3. In certain embodiments, a Notch ligand binding region comprises amino acids 445-455 (PCEHGGSCLNT; SEQ ID NO: 24) of human Notch4. In certain embodiments, a Notch ligand binding region comprises amino acids 447-448 (EH; residues 3 and 4 of SEQ ID NO: 24) of human Notch4. In certain embodiments, a Notch ligand binding region comprises amino acid 447 (E; residue 3 of SEQ ID NO: 24) of human Notch4.

That an antibody "selectively binds" or "specifically binds" to an epitope, antigen, or receptor means that the antibody reacts or associates more frequently, more rapidly, with greater duration, with greater affinity, or with some combination of the above to an epitope than with alternative substances, including unrelated proteins. "Selectively binds" means, for instance, that an antibody binds to a protein with a $K_D$ of at least about 0.1 mM, but more usually at least about 1 µM. "Specifically binds" means at times that an antibody binds to a protein at times with a $K_D$ of at least about 1 µM or better, and at other times at least about 0.01 µM or better. Because of the sequence identity between proteins in the same family, specific binding can include an antibody that recognizes a homologous epitope in more than one protein of the same protein family. For example, "specific binding" to a glutamate ligand binding region on a given Notch receptor (e.g. Notch1) encompasses antibodies that recognize only the Notch ligand binding region in that particular Notch receptor but also encompasses antibodies that recognize the Notch ligand binding region of that particular Notch receptor and the glutamate ligand binding region of one or more different Notch receptors (e.g. antibodies that recognize the ligand binding region of Notch1 and Notch2; Notch1 and Notch3; Notch1 and Notch4; Notch 2 and Notch3; Notch2 and Notch4; Notch 3 and Notch4; Notch1, Notch2, and Notch3; Notch 1, Notch2, and Notch4; Notch1, Notch3, Notch4; Notch2, Notch3, and Notch4; and Notch1, Notch2, Notch3, and Notch4). Because of the sequence identity between homologous proteins in different species, specific binding can include an antibody that recognizes a protein, for instance a cancer stem cell marker protein, in more than one species.

As used herein, the terms "non-specific binding" and "background binding", when used in reference to the interaction of an antibody and a protein or peptide, refer to an interaction that is not dependent on the presence of a particular structure (i.e., the antibody is binding to proteins in general rather that a particular structure such as an epitope).

The terms "isolated" or "purified" refer to material that is substantially or essentially free from components that normally accompany it in its native state. Purity and homogeneity are typically determined using analytical chemistry techniques such as polyacrylamide gel electrophoresis or high performance liquid chromatography. A protein (e.g. an antibody) or nucleic acid of the present disclosure that is the predominant species present in a preparation is substantially purified. In particular, an isolated nucleic acid is separated from open reading frames that naturally flank the gene and encode proteins other than protein encoded by the gene. An isolated antibody is separated from other non-immunoglobulin proteins and from other immuno globulin proteins with different antigen binding specificity. It can also mean that the nucleic acid or protein is in some embodiments at least 80% pure, in some embodiments at least 85% pure, in some embodiments at least 90% pure, in some embodiments at least 95% pure, and in some embodiments at least 99% pure.

As used herein, the terms "cancer" and "cancerous" refer to or describe the physiological condition in mammals in which a population of cells are characterized by unregulated cell growth. Examples of cancer include, but are not limited to, carcinoma, lymphoma, blastoma, sarcoma, and leukemia. More particular examples of such cancers include squamous cell cancer, small-cell lung cancer, non-small cell lung cancer, adenocarcinoma of the lung, squamous carcinoma of the lung, cancer of the peritoneum, hepatocellular cancer, gastrointestinal cancer, pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney cancer, liver cancer, prostate cancer, vulval cancer, thyroid cancer, hepatic carcinoma and various types of head and neck cancers.

The terms "proliferative disorder" and "proliferative disease" refer to disorders associated with abnormal cell proliferation such as cancer.

"Tumor" and "neoplasm" as used herein refer to any mass of tissue that results from excessive cell growth or proliferation, either benign (noncancerous) or malignant (cancerous) including pre-cancerous lesions.

"Metastasis" as used herein refers to the process by which a cancer spreads or transfers from the site of origin to other regions of the body with the development of a similar cancerous lesion at the new location. A "metastatic" or "metastasizing" cell is one that loses adhesive contacts with neighboring cells and migrates via the bloodstream or lymph from the primary site of disease to invade neighboring body structures.

The terms "cancer stem cell", "tumor stem cell", or "solid tumor stem cell" are used interchangeably herein and refer to a population of cells from a solid tumor that: (1) have extensive proliferative capacity; 2) are capable of asymmetric cell division to generate one or more kinds of differentiated progeny with reduced proliferative or developmental potential; and (3) are capable of symmetric cell divisions for self-renewal or self-maintenance. These properties of "cancer stem cells", "tumor stem cells" or "solid tumor stem cells" confer on those cancer stem cells the ability to form palpable tumors upon serial transplantation into an immunocompromised mouse compared to the majority of tumor cells that fail to form tumors. Cancer stem cells undergo self-renewal versus differentiation in a chaotic manner to form tumors with abnormal cell types that can change over time as mutations occur. Solid tumor stem cells differ from the "cancer stem line" provided by U.S. Pat. No. 6,004,528. In that patent, the "cancer stem line" is defined as a slow growing progenitor cell type that itself has few mutations but which undergoes symmetric rather than asymmetric cell divisions as a result of tumorigenic changes that occur in the cell's environment. This "cancer stem line" hypothesis thus proposes that highly mutated, rapidly proliferating tumor cells arise largely as a result of an abnormal environment, which causes relatively normal stem cells to accumulate and then undergo mutations that cause them to become tumor cells. U.S. Pat. No. 6,004,528 proposes that such a model can be used to enhance the diagnosis of cancer. The solid tumor stem cell model is fundamentally different from the "cancer stem line" model and as a result exhibits utilities not offered by the "cancer stem line" model. First, solid tumor stem cells are not "mutationally spared". The "mutationally spared cancer stem line" described by U.S. Pat. No. 6,004,528 can be considered a pre-cancerous lesion, while solid tumor stem cells are cancer cells that can themselves contain the mutations that are responsible for tumorigenesis starting at the pre-cancerous stage through later stage cancer. That is, solid tumor stem cells ("cancer stem cells") would be included among the highly mutated cells that are distinguished from the "cancer stem line" in U.S. Pat. No. 6,004,528. Second, the genetic mutations that lead to cancer can be largely intrinsic within the solid tumor stem cells as well as being environmental. The solid tumor stem cell model predicts that isolated solid tumor stem cells can give rise to additional tumors upon transplantation (thus explaining metastasis) while the "cancer stem line" model would predict that transplanted "cancer stem line" cells would not be able to give rise to a new tumor, since it was their abnormal environment that was tumorigenic. Indeed, the ability to transplant dissociated, and phenotypically isolated human solid tumor stem cells to mice (into an environment that is very different from the normal tumor environment) where they still form new tumors distinguishes the present invention from the "cancer stem line" model. Third, solid tumor stem cells likely divide both symmetrically and asymmetrically, such that symmetric cell division is not an obligate property. Fourth, solid tumor stem cells can divide rapidly or slowly, depending on many variables, such that a slow proliferation rate is not a defining characteristic.

The terms "cancer cell", "tumor cell" and grammatical equivalents refer to the total population of cells derived from a tumor or a pre-cancerous lesion including both non-tumorigenic cells, which comprise the bulk of the tumor cell population, and tumorigenic stem cells (cancer stem cells).

As used herein "tumorigenic" refers to the functional features of a solid tumor stem cell including the properties of self-renewal (giving rise to additional tumorigenic cancer stem cells) and proliferation to generate all other tumor cells (giving rise to differentiated and thus non-tumorigenic tumor cells) that allow solid tumor stem cells to form a tumor.

As used herein, the terms "stem cell cancer marker(s)", "cancer stem cell marker(s)", "tumor stem cell marker(s)", or "solid tumor stem cell marker(s)" refer to a gene or genes or a protein, polypeptide, or peptide expressed by the gene or genes whose expression level, alone or in combination with other genes, is correlated with the presence of tumorigenic cancer cells compared to non-tumorigenic cells. The correlation can relate to either an increased or decreased expression of the gene (e.g. increased or decreased levels of mRNA or the peptide encoded by the gene).

As used herein, the terms "biopsy" or "biopsy tissue" refer to a sample of tissue or fluid that is removed from a subject for the purpose of determining if the sample contains cancerous tissue. In some embodiments, biopsy tissue or fluid is obtained because a subject is suspected of having cancer, and the biopsy tissue or fluid is then examined for the presence or absence of cancer.

As used herein, the term "subject" refers to any animal (e.g., a mammal), including, but not limited to humans, non-human primates, rodents, and the like, which is to be the recipient of a particular treatment or protocol describe herein. Typically, the terms "subject" and "patient" are used interchangeably herein in reference to a human subject.

"Pharmaceutically acceptable" refers to approved or approvable by a regulatory agency of the Federal or a state government or listed in the U.S. Pharmacopeia or other generally recognized pharmacopeia for use in animals, including humans.

"Pharmaceutically acceptable salt" refers to a salt of a compound that is pharmaceutically acceptable and that possesses the desired pharmacological activity of the parent compound.

"Pharmaceutically acceptable excipient, carrier or adjuvant" refers to an excipient, carrier or adjuvant that can be administered to a subject, together with at least one antibody of the present disclosure, and which does not destroy the pharmacological activity thereof and is nontoxic when administered in doses sufficient to deliver a therapeutic amount of the compound.

"Pharmaceutically acceptable vehicle" refers to a diluent, adjuvant, excipient, or carrier with which at least one antibody of the present disclosure is administered.

"Prodrug" refers to a derivative of a therapeutically effective compound that requires a transformation within the body to produce the therapeutically effective compound. Prodrugs can be pharmacologically inactive until converted to the therapeutically effective parent compound.

The term "therapeutically effective amount" refers to an amount of an antibody, polypeptide, polynucleotide, small organic molecule, or other drug effective to "treat" a disease or disorder in a subject or mammal. In the case of cancer, the therapeutically effective amount of the drug can reduce the number of cancer cells; reduce the tumor size; inhibit or stop cancer cell infiltration into peripheral organs including, for example, the spread of cancer into soft tissue and bone; inhibit and stop tumor metastasis; inhibit and stop tumor growth; relieve to some extent one or more of the symptoms associated with the cancer, reduce morbidity and mortality; improve quality of life; or a combination of such effects. To the extent the drug prevents growth and/or kills existing cancer cells, it can be referred to as cytostatic and/or cytotoxic.

As used herein, "providing a diagnosis" or "diagnostic information" refers to any information, including for example the presence of cancer stem cells, that is useful in determining whether a patient has a disease or condition and/or in classifying the disease or condition into a phenotypic category or any category having significance with regards to the prognosis of or likely response to treatment (either treatment in general or any particular treatment) of the disease or condition. Similarly, diagnosis refers to providing any type of diagnostic information, including, but not limited to, whether a subject is likely to have a condition (such as a tumor), whether a subject's tumor comprises cancer stem cells, information related to the nature or classification of a tumor as for example a high risk tumor or a low risk tumor, information related to prognosis and/or information useful in selecting an appropriate treatment. Selection of treatment can include the choice of a particular chemotherapeutic agent or other treatment modality such as surgery or radiation or a choice about whether to withhold or deliver therapy.

As used herein, the terms "providing a prognosis", "prognostic information", or "predictive information" refer to providing information, including for example the presence of cancer stem cells in a subject's tumor, regarding the impact of the presence of cancer (e.g., as determined by the diagnostic methods of the present invention) on a subject's future health (e.g., expected morbidity or mortality, the likelihood of getting cancer, and the risk of metastasis).

Terms such as "treating" or "treatment" or "to treat" or "alleviating" or "to alleviate" refer to both 1) therapeutic measures that cure, slow down, lessen symptoms of, and/or halt progression of a diagnosed pathologic condition or disorder and 2) prophylactic or preventative measures that prevent and/or slow the development of a targeted pathologic condition or disorder. Thus those in need of treatment include those already with the disorder; those prone to have the disorder; and those in whom the disorder is to be prevented. A subject is successfully "treated" according to the methods of the present invention if the patient shows one or more of the following: a reduction in the number of or complete absence of cancer cells; a reduction in the tumor size; inhibition of or an absence of cancer cell infiltration into peripheral organs including, for example, the spread of cancer into soft tissue and bone; inhibition of or an absence of tumor metastasis; inhibition or an absence of tumor growth; relief of one or more symptoms associated with the specific cancer; reduced morbidity and mortality; improvement in quality of life; or some combination of effects.

As used herein, the terms "polynucleotide" or "nucleic acid" refer to a polymer composed of a multiplicity of nucleotide units (ribonucleotide or deoxyribonucleotide or related structural variants) linked via phosphodiester bonds, including but not limited to, DNA or RNA. The term encompasses sequences that include any of the known base analogs of DNA and RNA. including, but not limited to, 4-acetylcytosine, 8-hydroxy-N-6-methyladenosine, aziridinylcytosine, pseudoisocytosine, 5-(carboxyhydroxylmethyl) uracil, 5-fluorouracil, 5-bromouracil, 5-carboxymethylaminomethyl-2-thiouracil, 5-carboxymethylaminomethyluracil, dihydrouracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, N6-methyladenine, 7-methylguanine, 5-methylaminomethyluracil, 5-methoxyaminomethyl-2-thiouracil, beta-D-mannosylqueosine, 5'-methoxycarbonylmethyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2 thiouracil, 2-thiouracil, 4-thiouracil, 5-methyluracil, N-uracil 5-oxyacetic acid methylester, uracil-5-oxyacetic acid, pseudouracil, queosine, 2-thiocytosine, and 2,6 diaminopurine.

The term "gene" refers to a nucleic acid (e.g., DNA) sequence that comprises coding sequences necessary for the production of a polypeptide, precursor, or RNA (e.g., rRNA, tRNA). The polypeptide can be encoded by a full length coding sequence or by any portion of the coding sequence so long as the desired activity or functional properties (e.g., enzymatic activity, ligand binding, signal transduction, immunogenicity, etc.) of the full-length or fragment are retained. The term also encompasses the coding region of a structural gene and the sequences located adjacent to the coding region on both the 5' and 3' ends for a distance of about 1 kb or more on either end such that the gene corresponds to the length of the full-length mRNA. Sequences located 5' of the coding region and present on the mRNA are referred to as 5' non-translated sequences. Sequences located 3' or downstream of the coding region and present on the mRNA are referred to as 3' non-translated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene that are transcribed into nuclear RNA (hnRNA); introns can contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide. In addition to containing introns, genomic forms of a gene can also include sequences located on both the 5' and 3' end of the sequences that are present on the RNA transcript. These sequences are referred to as "flanking" sequences or regions (these flanking sequences are located 5' or 3' to the non-translated sequences present on the mRNA transcript). The 5' flanking region can contain regulatory sequences such as promoters and enhancers that control or influence the transcription of the gene. The 3' flanking region can contain sequences that direct the termination of transcription, post transcriptional cleavage and polyadenylation.

The term "recombinant" when used with reference to a cell, nucleic acid, protein or vector indicates that the cell, nucleic acid, protein or vector has been modified by the introduction of a heterologous nucleic acid or protein, the alteration of a native nucleic acid or protein, or that the cell is derived from a cell so modified. Thus, e.g., recombinant cells express genes that are not found within the native (non-recombinant) form of the cell or express native genes that are overexpressed or otherwise abnormally expressed such as, for example, expressed as non-naturally occurring fragments or splice variants. By the term "recombinant nucleic acid" herein is meant nucleic acid, originally formed in vitro, in general, by the manipulation of nucleic acid, e.g., using polymerases and endonucleases, in a form not normally found in nature. In this manner, operably linkage of different sequences is achieved. Thus an isolated nucleic acid, in a linear form, or an expression vector formed in vitro by ligating DNA molecules that are not normally joined, are both considered recombinant for the purposes of this invention. It is understood that once a recombinant nucleic acid is made and introduced into a host cell or organism, it will replicate non-recombinantly, i.e., using the in vivo cellular machinery of the host cell rather than in vitro manipulations; however, such nucleic acids, once produced recombinantly, although subsequently replicated non-recombinantly, are still considered recombinant for the purposes of the invention. Similarly, a "recombinant protein" is a protein made using recombinant techniques, i.e., through the expression of a recombinant nucleic acid as depicted above.

As used herein, the term "heterologous gene" refers to a gene that is not in its natural environment. For example, a heterologous gene includes a gene from one species introduced into another species. A heterologous gene also includes a gene native to an organism that has been altered in some way (e.g., mutated, added in multiple copies, linked to non-native regulatory sequences, etc). Heterologous genes are distinguished from endogenous genes in that the heterologous gene sequences are typically joined to DNA sequences that are not found naturally associated with the gene sequences in the chromosome or are associated with portions of the chromosome not found in nature (e.g., genes expressed in loci where the gene is not normally expressed).

As used herein, the term "vector" is used in reference to nucleic acid molecules that transfer DNA segment(s) from one cell to another. The term "vehicle" is sometimes used interchangeably with "vector." Vectors are often derived from plasmids, bacteriophages, or plant or animal viruses.

"Ligation" refers to the process of forming phosphodiester bonds between two double stranded nucleic acid fragments. Unless otherwise provided, ligation can be accomplished using known buffers and conditions with 10 units to T4 DNA ligase ("ligase") per 0.5 ug of approximately equimolar amounts of the DNA fragments to be ligated. Ligation of nucleic acid can serve to link two proteins together in-frame to produce a single protein, or fusion protein.

As used herein, the term "gene expression" refers to the process of converting genetic information encoded in a gene into RNA (e.g., mRNA, rRNA, tRNA, or snRNA) through "transcription" of the gene (e.g., via the enzymatic action of an RNA polymerase), and for protein encoding genes, into protein through "translation" of mRNA. Gene expression can be regulated at many stages in the process. "Up-regulation" or "activation" refers to regulation that increases the production of gene expression products (e.g., RNA or protein), while "down-regulation" or "repression" refers to regulation that decrease production. Molecules (e.g., transcription factors) that are involved in up-regulation or down-regulation are often called "activators" and "repressors," respectively.

The terms "polypeptide," "peptide," "protein," and "protein fragment" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymers.

The term "amino acid" refers to naturally occurring and synthetic amino acids, as well as amino acid analogs and amino acid mimetics that function similarly to the naturally occurring amino acids. Naturally occurring amino acids are those encoded by the genetic code, as well as those amino acids that are later modified, e.g., hydroxyproline, gamma-carboxyglutamate, and O-phosphoserine. Amino acid analogs refers to compounds that have the same basic chemical structure as a naturally occurring amino acid, e.g., an alpha carbon that is bound to a hydrogen, a carboxyl group, an amino group, and an R group, e.g., homoserine, norleucine, methionine sulfoxide, methionine methyl sulfonium. Such analogs can have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions similarly to a naturally occurring amino acid.

"Conservatively modified variants" applies to both amino acid and nucleic acid sequences. "Amino acid variants" refers to amino acid sequences. With respect to particular nucleic acid sequences, conservatively modified variants refers to those nucleic acids which encode identical or essentially identical amino acid sequences, or where the nucleic acid does not encode an amino acid sequence, to essentially identical or associated (e.g., naturally contiguous) sequences. Because of the degeneracy of the genetic code, a large number of functionally identical nucleic acids encode most proteins. For instance, the codons GCA, GCC, GCG and GCU all encode the amino acid alanine Thus, at every position where an alanine is specified by a codon, the codon can be altered to another of the corresponding codons described without altering the encoded polypeptide. Such nucleic acid variations are "silent variations," which are one species of conservatively modified variations. Every nucleic acid sequence herein which encodes a polypeptide also describes silent variations of the nucleic acid. One of skill will recognize that in certain contexts each codon in a nucleic acid (except AUG, which is ordinarily the only codon for methionine, and TGG, which is ordinarily the only codon for tryptophan) can be modified to yield a functionally identical molecule. Accordingly, silent variations of a nucleic acid which encodes a polypeptide is implicit in a described sequence with respect to the expression product, but not with respect to actual probe sequences. As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" including where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention. Typically conservative substitutions include: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, Proteins (1984)).

The term "epitope tagged" as used herein refers to a chimeric polypeptide comprising a cancer stem cell marker protein, or a domain sequence or portion thereof, fused to an "epitope tag". The epitope tag polypeptide comprises enough amino acid residues to provide an epitope for recognition by an antibody, yet is short enough such that it does not interfere with the activity of the cancer stem cell marker protein. Suitable epitope tags generally have at least six amino acid residues, usually between about 8 to about 50 amino acid residues, and at times between about 10 to about 20 residues. Commonly used epitope tags include Fc, HA, His, and FLAG tags.

DESCRIPTION OF THE PRESENT INVENTION

The present invention provides compositions and methods for studying, diagnosing, characterizing, and treating cancer. In particular, the present invention provides antagonists, including antibodies, against a Notch receptor and methods of using such antagonists to inhibit tumor growth and treat cancer in human patients. In certain embodiments, antibodies of the present invention specifically bind to the conserved ligand binding region of at least one Notch receptor and inhibit tumor growth.

The present invention for the first time identifies a conserved ligand binding region within the ligand binding domain of the Notch family of receptors. Specifically, the ligand binding region encompasses a conserved glutamate within EGF11 of Notch1, Notch2, and Notch4 and EGF10 of Notch3 that is necessary for ligand binding, and this invention provides molecules, as well as methods for generating molecules, that specifically interact with this ligand binding region to disrupt ligand binding to a Notch receptor. In certain embodiments, the present invention provides an antagonist that specifically binds to the ligand binding region of at least one Notch receptor and inhibits the growth of tumor cells. In certain embodiments, the antagonist is an antibody. In certain embodiments, the present invention provides an isolated antagonist that specifically binds to the ligand binding region of two or more Notch receptors and inhibits the growth of tumor cells. In certain embodiments, the antagonist is an antibody.

The present invention also provides pharmaceutical compositions and articles of manufacture. In certain embodiments, the pharmaceutical composition comprises an antagonist of the present disclosure and a pharmaceutically acceptable vehicle. In certain embodiments, an article of manufacture comprises a container and a composition contained therein, wherein the composition comprises an antagonist or a pharmaceutical composition of the present disclosure. In certain embodiments, the article of manufacture further comprises a package inset indicating that the composition can be used to treat cancer. In certain embodiments, the package inset indicates that the composition can be used to treat cancer comprising cancer stem cells.

Further provided are methods of treating cancer in a subject. In certain embodiments, the method of treating cancer comprises administering a therapeutically effective amount of an antagonist of the present disclosure in an amount effective to inhibit tumor cell growth. Examples of solid tumors that can be treated using a therapeutic composition of the instant invention include, but are not limited to, sarcomas and carcinomas. In certain methods of the present invention, the cancer is selected from the group consisting of breast, colon, pancreatic, prostate, lung, head and neck, rectal, and colorectal cancer. In certain embodiments, the cancer comprises tumor stem cells.

Cancer Stem Cells and Notch Receptors

Common cancers arise in tissues that contain a subpopulation of proliferating cells that are responsible for replenishing the short-lived mature cells. In such organs, cell maturation is arranged in a hierarchy in which a rare population of stem cells give rise both to the more differentiated cells and perpetuate themselves through a process called self renewal (Akashi & Weissman, Developmental Biology of Hematopoiesis, Oxford Univ. Press, NY, 2001; Spangrude et al., 1988, Science 241:58-61; Baum et al., 1992, PNAS 89:2804-8; Morrison et al., 1995, PNAS 92:10302-6; Morrison et al., 1996, Immunity 5:207-16; Morrison et al., 1995, Annu Rev. Cell Dev. Biol. 11:35-71; Morrison et al., 1997, Dev. 124: 1929-39; Morrison & Weissman, 1994, Immunity 1:661; Morrison et al., 1997, Cell 88:287-98; Uchida et al., 2000, PNAS 97:14720-5; Morrison et al., 2000, Cell 101:499-510). Although it is likely that most tissues contain stem cells, due to their rarity these cells have been rigorously identified and purified to study their biological, molecular, and biochemical properties in only a few tissues. The best characterized stem cells are those that give rise to the hematopoietic system, called hematopoietic stem cells (HSCs). The utility of HSCs has been demonstrated in cancer therapy with their extensive use for bone marrow transplantation to regenerate the hematolymphoid system following myeloablative protocols (Baum et al., Bone Marrow Transplantation, Blackwell Scientific Publications, Boston, 1994). Understanding the cellular biology of the tissues in which cancers arise, and specifically of the stem cells residing in those tissues, promises to provide new insights into cancer biology.

Like the tissues in which they originate, solid tumors consist of a heterogeneous population of cells. That the majority of these cells lack tumorigenicity suggested that the development and maintenance of solid tumors also relies on a small population of stem cells (i.e., tumorigenic cancer cells) with the capacity to proliferate and efficiently give rise both to additional tumor stem cells (self-renewal) and to the majority of more differentiated tumor cells that lack tumorigenic potential (i.e., non-tumorigenic cancer cells). The concept of cancer stem cells was first introduced soon after the discovery of hematopoietic stem cells (HSC) and was established experimentally in acute myelogenous leukemia (AML) (Park et al., 1971, *J. Natl. Cancer Inst.* 46:411-22; Lapidot et al., 1994, *Nature* 367:645-8; Bonnet & Dick, 1997, *Nat. Med.* 3:730-7; Hope et al., 2004, *Nat. Immunol.* 5:738-43). Stem cells from solid tumors have more recently been isolated based on their expression of a unique pattern of cell-surface receptors and on the assessment of their properties of self-renewal and proliferation in culture and in xenograft animal models. An ESA+ CD44+ CD24−/low Lineage-population greater than 50-fold enriched for the ability to form tumors relative to unfractionated tumor cells was discovered (Al-Hajj et al., 2003, *Proc. Nat'l. Acad. Sci.* 100:3983-8). The ability to isolate tumorigenic cancer stem cells from the bulk of non-tumorigenic tumor cells has led to the identification of cancer stem cell markers, genes with differential expression in cancer stem cells compared to non-tumorigenic tumor cells or normal breast epithelium, using microarray analysis. The present invention employs the knowledge of these identified cancer stem cell markers to study, characterize, diagnosis, and treat cancer.

Normal stem cells and cancer stem cells share the ability to proliferate and self-renew, thus is not surprising that a number of genes that regulate normal stem cell development contribute to tumorigenesis (reviewed in Reya et al., 2001, Nature 414:105-111 and Taipale & Beachy, 2001, Nature 411:349-354). The cancer stem cell markers of the present invention relate to human Notch receptors. The Notch signaling pathway is one of several critical regulators of embryonic pattern formation, post-embryonic tissue maintenance, and stem cell biology. More specifically, Notch signaling is involved in the process of lateral inhibition between adjacent cell fates and plays an important role in cell fate determination during asymmetric cell divisions. Unregulated Notch signaling is associated with numerous human cancers where it can alter the developmental fate of tumor cells to maintain them in an undifferentiated and proliferative state (Brennan and Brown, 2003, *Breast Cancer Res.* 5:69). Thus carcinogenesis can proceed by usurping homeostatic mechanisms controlling normal development and tissue repair by stem cell populations (Beachy et al., 2004, *Nature* 432:324).

The Notch receptor was first identified in *Drosophila* mutants. Haploinsufficiency of *Drosophila* Notch results in notches at the wing margin whereas loss-of-function produces an embryonic lethal "neurogenic" phenotype where cells of the epidermis switch fate to neural tissue (Moohr, 1919, *Genet.* 4:252; Poulson, 1937, *PNAS* 23:133; Poulson, 1940, *J. Exp. Zool.* 83:271). The Notch receptor is a single-pass transmembrane receptor containing numerous tandem epidermal growth factor (EGF)-like repeats and cysteine-rich Notch/LIN-12 repeats within a large extracellular domain (Wharton et al., 1985, *Cell* 43:567; Kidd et al., 1986, *Mol. Cell. Biol.* 6:3094; reviewed in Artavanis et al., 1999, *Science* 284:770). Four mammalian Notch proteins have been identified (NOTCH1, NOTCH2, NOTCH3, and NOTCH4), and mutations in these receptors invariably result in developmental abnormalities and human pathologies including several cancers as described in detail below (Gridley, 1997, *Mol. Cell. Neurosci.* 9:103; Joutel & Tournier-Lasserve, 1998, *Semin. Cell Dev. Biol.* 9:619-25).

The Notch receptor is activated by single-pass transmembrane ligands of the Delta, Serrated, Lag-2 (DSL) family. The known Notch ligands in mammals, Delta-like 1 (Dll1), Delta-like 3 (Dll3), Delta-like 4 (Dll4), Jagged 1 and Jagged 2, are characterized by a DSL domain and tandem EGF-like repeats within the extracellular domain. The extracellular domain of the Notch receptor interacts with that of its ligands, typically on adjacent cells, resulting in two proteolytic cleavages of Notch, an extracellular cleavage mediated by an ADAM protease and a cleavage within the transmembrane domain mediated by gamma secretase. This latter cleavage generates the Notch intracellular domain (NICD). The NICD then enters the nucleus where it activates the CBF1, Suppressor of Hairless [Su(H)], Lag-2 (CSL) family of transcription factors as the major downstream effectors to increase transcription of nuclear basic helix-loop-helix transcription factors of the Hairy and Enhancer of Split [E(spl)] family (Artavanis et al., 1999, *Science* 284:770; Brennan and Brown, 2003, *Breast Cancer Res.* 5:69; Iso et al., 2003, *Arterioscler. Thromb. Vasc. Biol.* 23:543). Alternative intracellular pathways involving the cytoplasmic protein Deltex identified in *Drosophila* may also exist in mammals (Martinez et al., 2002, *Curr. Opin. Genet. Dev.* 12:524-33), and this Deltex-dependent pathway may act to suppress expression of Wnt target genes (Brennan et al., 1999, *Curr. Biol.* 9:707-710; Lawrence et al., 2001, *Curr. Biol.* 11:375-85).

Hematopoietic stem cells (HSCs) are the best understood stem cells in the body, and Notch signaling is implicated both in their normal maintenance as well as in leukemic transformation (Kopper & Hajdu, 2004, *Pathol. Oncol. Res.* 10:69-73). HSCs are a rare population of cells that reside in a stromal niche within the adult bone marrow. These cells are characterized both by a unique gene expression profile as well as an ability to continuously give rise to more differentiated progenitor cells to reconstitute the entire hematopoietic system. Constitutive activation of Notch1 signaling in HSCs and progenitor cells establishes immortalized cell lines that generate both lymphoid and myeloid cells in vitro and in long-term reconstitution assays (Varnum-Finney et al., 2000, *Nat. Med.* 6:1278-81), and the presence of Jagged 1 increases engraftment of human bone marrow cell populations enriched for HSCs (Karanu et al., 2000, *J. Exp. Med.* 192:1365-72). More recently, Notch signaling has been demonstrated in HSCs in vivo and shown to be involved in inhibiting HSC differentiation. Furthermore, Notch signaling appears to be required for Wnt-mediated HSC self-renewal (Duncan et al., 2005, *Nat. Immunol.* 6:314).

The Notch signaling pathway also plays a central role in the maintenance of neural stem cells and is implicated both in their normal maintenance as well as in brain cancers (Kopper & Hajdu, 2004, *Pathol. Oncol. Res.* 10:69-73; Purow et al., 2005, *Cancer Res.* 65:2353-63; Hallahan et al., 2004, *Cancer Res.* 64:7794-800). Neural stem cells give rise to all neuronal and glial cells in the mammalian nervous system during development, and more recently have been identified in the adult brain (Gage, 2000, *Science* 287:1433-8). Mice deficient for Notch1; the Notch target genes Hes1, 3, and 5; and a regulator of Notch signaling presenilin1 (PS1) show decreased numbers of embryonic neural stem cells. Furthermore, adult neural stem cells are reduced in the brains of PS1 heterozygote mice (Nakamura et al., 2000, *J. Neurosci.* 20:283-93; Hitoshi et al., 2002, *Genes Dev.* 16:846-58). The reduction in neural stem cells appears to result from their premature differentiation into neurons (Hatakeyama et al., 2004, *Dev.* 131:5539-50) suggesting that Notch signaling regulates neural stem cell differentiation and self-renewal.

Aberrant Notch signaling is implicated in a number of human cancers. The NOTCH1 gene in humans was first identified in a subset of T-cell acute lymphoblastic leukemias as a translocated locus resulting in activation of the Notch pathway (Ellisen et al., 1991, *Cell* 66:649-61). Constitutive activation of Notch1 signaling in T-cells in mouse models similarly generates T-cell lymphomas suggesting a causative role (Robey et al., 1996, *Cell* 87:483-92; Pear et al., 1996, *J. Exp. Med.* 183:2283-91; Yan et al., 2001, *Blood* 98:3793-9; Bellavia et al., 2000, *EMBO J.* 19:3337-48). Recently NOTCH1 point mutations, insertions, and deletions producing aberrant NOTCH1 signaling have been found to be frequently present in both childhood and adult T-cell acute lymphoblastic leukemia/lymphoma (Pear & Aster, 2004, *Curr. Opin. Hematol.* 11:416-33).

The frequent insertion of the mouse mammary tumor virus into both the Notch1 and Notch4 locus in mammary tumors and the resulting activated Notch protein fragments first implicated Notch signaling in breast cancer (Gallahan & Callahan, 1987, *J. Virol.* 61:66-74; Brennan & Brown, 2003, *Breast Cancer Res.* 5:69; Politi et al., 2004, *Semin. Cancer Biol.* 14:341-7). Further studies in transgenic mice have confirmed a role for Notch in ductal branching during normal mammary gland development, and a constitutively active form of Notch4 in mammary epithelial cells inhibits epithelial differentiation and results in tumorigenesis (Jhappan et al., 1992, *Genes & Dev.* 6:345-5; Gallahan et al., 1996, *Cancer Res.* 56:1775-85; Smith et al., 1995, *Cell Growth Differ.* 6:563-77; Soriano et al., 2000, *Int. J. Cancer* 86:652-9; Uyttendaele et al., 1998, *Dev. Biol.* 196:204-17; Politi et al., 2004, *Semin. Cancer Biol.* 14:341-7). Currently the evidence for a role for Notch in human breast cancer is limited to the expression of Notch receptors in breast carcinomas and their correlation with clinical outcome (Weijzen et al., 2002, *Nat. Med.* 8:979-86; Parr et al., 2004, *Int. J. Mol. Med.* 14:779-86). Furthermore, overexpression of the Notch pathway has been observed in cervical cancers (Zagouras et al., 1995, *PNAS* 92:6414-8), renal cell carcinomas (Rae et al., 2000, *Int. J. Cancer* 88:726-32), head and neck squamous cell carcinomas (Leethanakul et al., 2000, *Oncogene* 19:3220-4), endometrial cancers (Suzuki et al., 2000, *Int. J. Oncol.* 17:1131-9), and neuroblastomas (van Limpt et al., 2000, *Med. Pediatr. Oncol.* 35:554-8) indicative of a potential role for Notch in the development of a number of neoplasms. Interestingly, Notch signaling might play a role in the maintenance of the undifferentiated state of Apc-mutant neoplastic cells of the colon (van Es & Clevers, 2005, *Trends Mol. Med.* 11:496-502).

The Notch pathway is also involved in multiple aspects of vascular development including proliferation, migration, smooth muscle differentiation, angiogenesis and arterial-venous differentiation (Iso et al., 2003, *Arterioscler. Thromb. Vasc. Biol.* 23:543). For example, homozygous null mutations in Notch-¼ and Jagged-1 as well as heterozygous loss of Dll4 result in severe though variable defects in arterial development and yolk sac vascularization. Furthermore, Dll1-deficient and Notch-2-hypomorphic mice embryos show hemorrhage that likely results from poor development of vascular structures (Gale et al., 2004, *PNAS*, 101:15949-54; Krebs et al., 2000, *Genes Dev.* 14:1343-52; Xue et al., 1999, *Hum. Mel Genet.* 8:723-30; Hrabe de Angelis et al., 1997, *Nature* 386:717-21; McCright et al., 2001, *Dev.* 128: 491-502). In humans, mutations in JAGGED1 are associated with Alagille syndrome, a developmental disorder that includes vascular defects, and mutations in NOTCH3 are responsible for an inherited vascular dementia (CADASIL) in which vessel homeostasis is defective (Joutel et al., 1996, *Nature* 383:707-10).

The identification of Notch receptors as expressed in cancer stem cells compared to normal breast epithelium suggested targeting the Notch pathway to eliminate not only the majority of non-tumorigenic cancer cells, but the tumorigenic cells responsible for the formation and reoccurrence of solid tumors. Furthermore, because of the prominent role of angiogenesis in tumor formation and maintenance, targeting the Notch pathway via antibodies against Notch receptors can also effectively inhibit angiogenesis, starving a cancer of nutrients and contributing to its elimination.

Notch receptors interact with their ligands via a ligand binding domain comprising several EGF repeats within the extracellular domain. Specifically, EGF repeats 11 and 12 of the Notch receptor family (EGF10-11 in Notch3) define a domain that is both necessary and sufficient to mediate ligand binding (Rebay et al., 1991, Cell 67:687-99; U.S. Pat. Nos. 5,786,158, 6,090,922), though other EGF repeats and glycosylation are required for optimal binding (Xu et al., *J. Biol. Chem.* 280: 30158-65). Sequence comparison revealed a conserved glutamate (E) within EGF11 of human Notch1, Notch2, Notch3 (homologous EGF10), and Notch4 but not in any of the other thirty-six EGF domains in these proteins (FIG. 1). Furthermore, this glutamate is conserved in EGF11 of *drosophila* Notch and *Xenopus* Notch (FIG. 1), but again in no other EGF repeats, and x-ray crystallography data show this glutamate on the surface of the folded EGF11 repeat (Hambleton et al., 2004, *Structure*, 12: 217-83). Together these data indicate an important role for this conserved glutamate residue in ligand binding by EGF11, and that antagonists targeting this ligand binding region can act as effective cancer therapeutics as described in detail below and in the examples.

The present invention contemplates use of the discovery of a conserved ligand binding region in human Notch receptors to identify agents that bind to this ligand binding region for the treatment of diseases mediated or aggravated by Notch signaling. As used herein "agent" refers to any molecule that specifically binds to the ligand binding region of any Notch receptor protein. Such agents include, but are not limited to, small organic molecules, small inorganic molecules, antibodies, and antibody fragments.

The conservation of the ligand binding domain, and particularly the glutamate residue, across Notch receptor proteins suggests the design of agents that bind to the ligand binding region of more than one Notch receptor. In certain embodiments, an agent of the present invention specifically binds to at least one human Notch receptor. In certain embodiments, an agent of the present invention specifically binds to at least two human Notch receptors. In certain embodiments, an agent of the present invention specifically binds to two or more human Notch receptors. In certain embodiments, an agent of the present invention binds to human Notch1, Notch2, Notch3, and Notch4. In some embodiments, the agent is an antibody.

The conservation of the ligand binding domain, and particularly the glutamate residue, suggests the design of agents that bind specifically to at least the conserved glutamate in the ligand binding region. In certain embodiments, an agent of the present invention specifically binds to an epitope within amino acids 422-432 (PCEHAGKCVNT; SEQ ID NO: 21) of human Notch1. In certain embodiments, an agent of the present invention specifically binds to at least amino acids 424-425 (EH; residues 3 and 4 of SEQ ID NO: 21) of human Notch1. In certain embodiments, an agent of the present invention specifically binds to at least amino acid 424 (E; residue 3 of SEQ ID NO: 21) of human Notch1. In certain embodiments, an agent of the present invention specifically binds to an epitope within amino acids 426-436 (PCE-HAGKCVNT; SEQ ID NO: 22) of human Notch2. In certain embodiments, an agent of the present invention specifically binds to at least amino acids 428-429 (EH; residues 3 and 4 of SEQ ID NO: 22) of human Notch2. In certain embodiments, an agent of the present invention specifically binds to at least amino acid 428 (E; residue 3 of SEQ ID NO: 22) of human Notch2. In certain embodiments, an agent of the present invention specifically binds to an epitope within amino acids 401-411 (PCEHLGRCVNT; SEQ ID NO: 23) of human Notch3. In certain embodiments, an agent of the present invention specifically binds to at least amino acids 403-404 (EH; residues 3 and 4 of SEQ ID NO: 23) of human Notch3. In certain embodiments, an agent of the present invention specifically binds to at least amino acid 403 (E; residue 3 of SEQ ID NO: 23) of human Notch3. In certain embodiments, an agent of the present invention specifically binds to an epitope within amino acids 445-55 (PCEHGGSCLNT; SEQ ID NO: 24) of human Notch4. In certain embodiments, an agent of the present invention specifically binds to at least amino acids 447-448 (EH; residues 3 and 4 of SEQ ID NO: 24) of human Notch4. In certain embodiments, an agent of the present invention specifically binds to at least amino acid 447 (E; residue 3 of SEQ ID NO: 24) of human Notch4. In some embodiments, the agent is an antibody.

The conservation of the ligand binding domain, and particularly the glutamate residue, suggests the design of antibodies that bind specifically to an epitope comprising the conserved glutamate in the ligand binding region. In certain embodiments, an antibody of the present invention specifically binds to an epitope comprising amino acids 422-432 (PCEHAGKCVNT; SEQ ID NO: 21) of human Notch1. In certain embodiments, an antibody of the present invention specifically binds to an epitope comprising amino acids 424-425 (EH; residues 3 and 4 of SEQ ID NO: 21) of human Notch1. In certain embodiments, an antibody of the present invention specifically binds to an epitope comprising amino acid 424 (E; residue 3 of SEQ ID NO: 21) of human Notch1. In certain embodiments, an antibody of the present invention specifically binds to an epitope comprising amino acids 426-436 (PCEHAGKCVNT; SEQ ID NO: 22) of human Notch2. In certain embodiments, an antibody of the present invention specifically binds to an epitope comprising amino acids 428-429 (EH; residues 3 and 4 of SEQ ID NO: 22) of human Notch2. In certain embodiments, an antibody of the present invention specifically binds to an epitope comprising amino acid 428 (E; residue 3 of SEQ ID NO: 22) of human Notch2. In certain embodiments, an antibody of the present invention specifically binds to an epitope comprising amino acids 401-411 (PCEHLGRCVNT; SEQ ID NO: 23) of human Notch3. In certain embodiments, an antibody of the present invention specifically binds to an epitope comprising amino acids 403-404 (EH; residues 3 and 4 of SEQ ID NO: 23) of human Notch3. In certain embodiments, an antibody of the present invention specifically binds to an epitope comprising amino acid 403 (E; residue 3 of SEQ ID NO: 23) of human Notch3. In certain embodiments, an antibody of the present invention specifically binds to an epitope comprising amino acids 445-455 (PCEHGGSCLNT; SEQ ID NO: 24) of human Notch4. In certain embodiments, an antibody of the present invention specifically binds to an epitope comprising amino acids 447-448 (EH; residues 3 and 4 of SEQ ID NO: 24) of human Notch4. In certain embodiments, an antibody of the present invention specifically binds to an epitope comprising amino acid 447 (E; residue 3 of SEQ ID NO: 24) of human Notch4. In some embodiments, the antibody is a monoclonal antibody. In some embodiments, the antibody is a chimeric antibody. In certain embodiments, the antibody is a humanized antibody. In certain embodiments, the antibody is a human antibody.

Diagnostic Assays

The present invention provides Notch receptors as cancer stem cell markers, the expression of which can be analyzed to detect, characterize, diagnosis, or monitor a disease associated with cancer. In some embodiments, expression of a cancer stem cell marker is determined by polynucleotide expression such as, for example, mRNA encoding the cancer stem cell marker. The polynucleotide can be detected and quantified by any of a number of means well known to those of skill in the art. In some embodiments, mRNA encoding a cancer stem cell marker is detected by in situ hybridization of tissue sections from, for example, a patient biopsy. In some embodiments, RNA is isolated from a tissue and detected by, for example, Northern blot, quantitative RT-PCR, or microarrays. For example, total RNA can be extracted from a tissue sample and primers that specifically hybridize and amplify a cancer stem cell marker can be used to detect expression of a cancer stem cell marker polynucleotide using RT-PCR.

In certain embodiments, expression of a cancer stem cell marker can be determined by detection of the corresponding polypeptide. The polypeptide can be detected and quantified by any of a number of means well known to those of skill in the art. In some embodiments, a cancer stem cell marker polypeptide is detected using analytic biochemical methods such as, for example, electrophoresis, capillary electrophoresis, high performance liquid chromatography (HPLC) or thin layer chromatography (TLC). The isolated polypeptide can also be sequenced according to standard techniques. In some embodiments, a cancer stem cell marker protein is detected with antibodies raised against the protein using, for example, immunofluorescence or immunohistochemistry on tissue sections. Alternatively antibodies against a cancer stem cell marker can detect expression using, for example, ELISA, FACS, Western blot, immunoprecipitation or protein microarrays. For example, cancer stem cells can be isolated from a patient biopsy and expression of a cancer stem cell marker protein detected with fluorescently labeled antibodies using FACS. In another method, the cells expressing a cancer stem cell marker can be detected in vivo using labeled antibodies in typical imaging system. For example, antibodies labeled with paramagnetic isotopes can be used for magnetic resonance imaging (MRI).

In some embodiments of the present invention, a diagnostic assay comprises determining the expression or not of a cancer stem cell marker in tumor cells using, for example, immunohistochemistry, in situ hybridization, or RT-PCR. In other embodiments, a diagnostic assay comprises determining expression levels of a cancer stem cell marker using, for example, quantitative RT-PCR. In some embodiments, a diagnostic assay further comprises determining expression levels of a cancer stem cell marker compared to a control tissue such as, for example, normal epithelium.

Detection of a cancer stem cell marker expression can then be used to provide a prognosis and select a therapy. A prognosis can be based on any known risk expression of a cancer stem cell marker indicates. Furthermore, detection of a cancer stem cell marker can be used to select an appropriate therapy including, for example, treatment with antibodies against the detected cancer stem cell marker protein. In certain embodiments, the antibody specifically binds to the extracellular domain of at least one human Notch receptor. In certain embodiments, the antibody specifically binds to a ligand binding region within EGF11 of at least one Notch receptor.

Antibodies

In the context of the present invention, a suitable antibody is an agent that can have one or more of the following effects, for example: interfere with the expression of a cancer stem cell marker; interfere with activation of a cancer stem cell signal transduction pathway by, for example, sterically inhibiting interactions between a cancer stem cell marker and its ligand, receptor or co-receptors; activate a cancer stem cell signal transduction pathway by, for example, acting as a ligand or promoting the binding of an endogenous ligand; or bind to a cancer stem cell marker and inhibit tumor cell proliferation.

In certain embodiments, antibodies against a cancer stem cell marker act extracellularly to modulate the function of a cancer stem cell marker protein. In some embodiments, extracellular binding of an antibody against a cancer stem cell marker can inhibit the signaling of a cancer stem cell marker protein by, for example, inhibiting intrinsic activation (e g kinase activity) of a cancer stem cell marker and/or by sterically inhibiting the interaction, for example, of a cancer stem cell marker with its ligand, with its receptor, with a co-receptor, or with the extracellular matrix. In some embodiments, extracellular binding of an antibody against a cancer stem cell marker can down-regulate cell-surface expression of a cancer stem cell marker such as, for example, by internalization of a cancer stem cell marker protein or decreasing cell surface trafficking of a cancer stem cell marker. In some embodiments, extracellular binding of an antibody against a cancer stem cell marker can promote the signaling of a cancer stem cell marker protein by, for example, acting as a decoy ligand or increasing ligand binding.

In certain embodiments, antibodies against a cancer stem cell marker bind to a cancer stem cell marker protein and have one or more of the following effects inhibit proliferation of tumor cells, trigger cell death of tumor cells, or prevent metastasis of tumor cells. In certain embodiments, antibodies against a cancer stem cell marker trigger cell death via a conjugated toxin, chemotherapeutic agent, radioisotope, or other such agent. For example, an antibody against a cancer stem cell marker is conjugated to a toxin that is activated in tumor cells expressing the cancer stem cell marker by protein internalization.

In certain embodiments, antibodies against a cancer stem cell marker mediate cell death of a cell expressing the cancer stem cell marker protein via antibody-dependent cellular cytotoxicity (ADCC). ADCC involves cell lysis by effector cells that recognize the Fc portion of an antibody. Many lymphocytes, monocytes, tissue macrophages, granulocytes and eosinophils, for example, have Fc receptors and can mediate cytolysis (Dillman, 1994, *J. Clin. Oncol.* 12:1497).

In certain embodiments, antibodies against a cancer stem cell marker trigger cell death of a cell expressing a cancer stem cell marker protein by activating complement-dependent cytotoxicity (CDC). CDC involves binding of serum complement to the Fc portion of an antibody and subsequent activation of the complement protein cascade, resulting in cell membrane damage and eventual cell death. Biological activity of antibodies is known to be determined, to a large extent, by the constant domains or Fc region of the antibody molecule (Uananue and Benacerraf, Textbook of Immunology, 2nd Edition, Williams & Wilkins, p. 218 (1984)). Antibodies of different classes and subclasses differ in this respect, as do antibodies of the same subclass but from different species. Of human antibodies, IgM is the most efficient class of antibodies to bind complement, followed by IgG1, IgG3, and IgG2 whereas IgG4 appears quite deficient in activating the complement cascade (Dillman, 1994, *J. Clin. Oncol.* 12:1497; Jefferis et al., 1998, *Immunol. Rev.* 163:59-76). According to the present invention, antibodies of those classes having the desired biological activity are prepared.

The ability of any particular antibody against a cancer stem cell to mediate lysis of the target cell by complement activation and/or ADCC can be assayed. The cells of interest are grown and labeled in vitro; the antibody is added to the cell culture in combination with either serum complement or immune cells which can be activated by the antigen antibody complexes. Cytolysis of the target cells is detected, for example, by the release of label from the lysed cells. In fact, antibodies can be screened using the patient's own serum as a source of complement and/or immune cells. The antibody that is capable of activating complement or mediating ADCC in the in vitro test can then be used therapeutically in that particular patient.

In certain embodiments, antibodies against a cancer stem cell marker can trigger cell death inhibiting angiogenesis. Angiogenesis is the process by which new blood vessels form from pre-existing vessels and is a fundamental process required for normal growth, for example, during embryonic development, wound healing, and in response to ovulation. Solid tumor growth larger than 1-2 $mm^2$ also requires angiogenesis to supply nutrients and oxygen without which tumor cells die. In certain embodiments, an antibody against a cancer stem cell marker targets vascular cells that express the cancer stem cell marker including, for example, endothelial cells, smooth muscle cells, or components of the extracellular matrix required for vascular assembly. In certain embodiments, an antibody against a cancer stem cell marker inhibits growth factor signaling required by vascular cell recruitment, assembly, maintenance, or survival.

The antibodies against a cancer stem cell marker find use in the diagnostic and therapeutic methods described herein. In certain embodiments, the antibodies of the present invention are used to detect the expression of a cancer stem cell marker protein in biological samples such as, for example, a patient tissue biopsy, pleural effusion, or blood sample. Tissue biopsies can be sectioned and protein detected using, for example, immunofluorescence or immunohistochemistry. In addition, individual cells from a sample can be isolated, and protein expression detected on fixed or live cells by FACS analysis. In certain embodiments, antibodies can be used on protein arrays to detect expression of a cancer stem cell marker, for example, on tumor cells, in cell lysates, or in other protein samples. In certain embodiments, the antibodies of the present invention are used to inhibit the growth of tumor cells by contacting the antibodies with tumor cells in in vitro cell based assays, in vivo animal models, etc. In certain embodiments, the antibodies are used to treat cancer in a patient by administering a therapeutically effective amount of an antibody against a cancer stem cell marker.

The antibodies of the invention can be prepared by any conventional means known in the art. For example, polyclonal antibodies can be prepared by immunizing an animal (e.g. a rabbit, rat, mouse, donkey, etc) by multiple subcutaneous or intraperitoneal injections of the relevant antigen (a purified peptide fragment, full-length recombinant protein, fusion protein, etc) optionally conjugated to keyhole limpet hemocyanin (KLH), serum albumin, etc. diluted in sterile saline and combined with an adjuvant (e.g. Complete or Incomplete Freund's Adjuvant) to form a stable emulsion. The polyclonal antibody is then recovered from blood, ascites and the like, of an animal so immunized. Collected blood is clotted, and the serum decanted, clarified by centrifugation, and assayed for antibody titer. The polyclonal antibodies can be purified from serum or ascites according to standard methods in the art including affinity chromatography, ion-exchange chromatography, gel electrophoresis, dialysis, etc.

Monoclonal antibodies can be prepared using hybridoma methods, such as those described by Kohler and Milstein (1975) *Nature* 256:495. Using the hybridoma method, a mouse, hamster, or other appropriate host animal, is immunized as described above to elicit the production by lymphocytes of antibodies that will specifically bind to an immunizing antigen. Lymphocytes can also be immunized in vitro. Following immunization, the lymphocytes are isolated and fused with a suitable myeloma cell line using, for example, polyethylene glycol, to form hybridoma cells that can then be selected away from unfused lymphocytes and myeloma cells. Hybridomas that produce monoclonal antibodies directed specifically against a chosen antigen as determined by immunoprecipitation, immunoblotting, or by an in vitro binding assay (e.g. radioimmunoassay (RIA); enzyme-linked immunosorbent assay (ELISA)) can then be propagated either in vitro culture using standard methods (Goding, Monoclonal Antibodies: Principles and Practice, Academic Press, 1986) or in vivo as ascites tumors in an animal. The monoclonal antibodies can then be purified from the culture medium or ascites fluid as described for polyclonal antibodies above.

Alternatively monoclonal antibodies can also be made using recombinant DNA methods as described in U.S. Pat. No. 4,816,567. The polynucleotides encoding a monoclonal antibody are isolated from mature B-cells or hybridoma cell, such as by RT-PCR using oligonucleotide primers that specifically amplify the genes encoding the heavy and light chains of the antibody, and their sequence is determined using conventional procedures. The isolated polynucleotides encoding the heavy and light chains are then cloned into suitable expression vectors, which when transfected into host cells such as *E. coli* cells, simian COS cells, Chinese hamster ovary (CHO) cells, or myeloma cells that do not otherwise produce immunoglobulin protein, monoclonal antibodies are generated by the host cells. Also, recombinant monoclonal antibodies or fragments thereof of the desired species can be isolated from phage display libraries expressing CDRs of the desired species as described (McCafferty et al., 1990, *Nature*, 348:552-554; Clackson et al., 1991, *Nature*, 352:624-628; and Marks et al., 1991, *J. Mol. Biol.*, 222:581-597).

The polynucleotide(s) encoding a monoclonal antibody can further be modified in a number of different manners using recombinant DNA technology to generate alternative antibodies. In some embodiments, the constant domains of the light and heavy chains of, for example, a mouse monoclonal antibody can be substituted 1) for those regions of, for example, a human antibody to generate a chimeric antibody or 2) for a non-immunoglobulin polypeptide to generate a fusion antibody. In some embodiments, the constant regions are truncated or removed to generate the desired antibody fragment of a monoclonal antibody. Site-directed or high-density mutagenesis of the variable region can be used to optimize specificity, affinity, etc. of a monoclonal antibody.

In some embodiments of the present invention, the monoclonal antibody against a cancer stem cell marker is a humanized antibody. Humanized antibodies are antibodies that contain minimal sequences from non-human (e.g. murine) antibodies within the variable regions. Such antibodies are used therapeutically to reduce antigenicity and HAMA (human anti-mouse antibody) responses when administered to a human subject. In practice, humanized antibodies are typically human antibodies with minimum to no non-human sequences. A human antibody is an antibody produced by a human or an antibody having an amino acid sequence corresponding to an antibody produced by a human.

Humanized antibodies can be produced using various techniques known in the art. An antibody can be humanized by substituting the CDR of a human antibody with that of a non-human antibody (e.g. mouse, rat, rabbit, hamster, etc.) having the desired specificity, affinity, and capability (Jones et al., 1986, *Nature*, 321:522-525; Riechmann et al., 1988, *Nature*, 332:323-327; Verhoeyen et al., 1988, *Science*, 239:1534-1536). The humanized antibody can be further modified by the substitution of additional residue either in the Fv framework region and/or within the replaced non-human residues to refine and optimize antibody specificity, affinity, and/or capability.

In addition, fully human antibodies can be directly prepared using various techniques known in the art. Immortalized human B lymphocytes immunized in vitro or isolated from an immunized individual that produce an antibody directed against a target antigen can be generated (See, e.g., Cole et al., Monoclonal Antibodies and Cancer Therapy, Alan R. Liss, p. 77 (1985); Boerner et al., 1991, *J. Immunol.*, 147 (1):86-95; and U.S. Pat. No. 5,750,373). Also, the human antibody can be selected from a phage library, where that phage library expresses human antibodies (Vaughan et al., 1996, *Nat. Biotech.*, 14:309-314; Sheets et al., 1998, *Proc. Nat'l. Acad. Sci.*, 95:6157-6162; Hoogenboom and Winter, 1991, *J. Mol. Biol.*, 227:381; Marks et al., 1991, *J. Mol. Biol.*, 222:581). Human antibodies can also be made in transgenic mice containing human immunoglobulin loci that are capable upon immunization of producing the full repertoire of human antibodies in the absence of endogenous immunoglobulin production. This approach is described in U.S. Pat. Nos. 5,545,807; 5,545,806; 5,569,825; 5,625,126; 5,633,425; and 5,661,016.

This invention also encompasses bispecific antibodies that specifically recognize a cancer stem cell marker. Bispecific antibodies are antibodies that are capable of specifically recognizing and binding at least two different epitopes. The different epitopes can either be within the same molecule (e.g. the same cancer stem cell marker polypeptide) or on different molecules such that both, for example, the antibodies can specifically recognize and bind a cancer stem cell marker as well as, for example, 1) an effector molecule on a leukocyte such as a T-cell receptor (e.g. CD3) or Fc receptor (e.g. CD64, CD32, or CD16) or 2) a cytotoxic agent as described in detail below. Bispecific antibodies can be intact antibodies or antibody fragments.

Exemplary bispecific antibodies can bind to two different epitopes, at least one of which originates in a polypeptide of the invention. Alternatively, an anti-antigenic arm of an immunoglobulin molecule can be combined with an arm which binds to a triggering molecule on a leukocyte such as a T cell receptor molecule (e.g. CD2, CD3, CD28, or B7), or Fc receptors for IgG so as to focus cellular defense mechanisms to the cell expressing the particular antigen. Bispecific antibodies can also be used to direct cytotoxic agents to cells which express a particular antigen. These antibodies possess an antigen-binding arm and an arm which binds a cytotoxic agent or a radionuclide chelator, such as EOTUBE, DPTA, DOTA, or TETA. Techniques for making bispecific antibodies are common in the art (Millstein et al., 1983, *Nature* 305:537-539; Brennan et al., 1985, *Science* 229:81; Suresh et al, 1986, *Methods in Enzymol.* 121:120; Traunecker et al., 1991, *EMBO J.* 10:3655-3659; Shalaby et al., 1992, *J. Exp. Med.* 175:217-225; Kostelny et al., 1992, *J. Immunol.* 148:1547-1553; Gruber et al., 1994, *J. Immunol.* 152:5368; and U.S. Pat. No. 5,731,168). Antibodies with more than two valencies are also contemplated. For example, trispecific antibodies can be prepared (Tutt et al., *J. Immunol.* 147:60 (1991))

In certain embodiments are provided an antibody fragment to, for example, increase tumor penetration. Various techniques are known for the production of antibody fragments: Traditionally, these fragments are derived via proteolytic digestion of intact antibodies (for example Morimoto et al., 1993, Journal of Biochemical and Biophysical Methods 24:107-117; Brennan et al., 1985, *Science,* 229:81). In certain embodiments, antibody fragments are produced recombinantly. Fab, Fv, and scFv antibody fragments can all be expressed in and secreted from *E. coli* or other host cells, thus allowing the production of large amounts of these fragments. Such antibody fragments can also be isolated from the antibody phage libraries discussed above. The antibody fragment can also be linear antibodies as described in U.S. Pat. No. 5,641,870, for example, and can be monospecific or bispecific. Other techniques for the production of antibody fragments will be apparent to the skilled practitioner.

According to the present invention, techniques can be adapted for the production of single-chain antibodies specific to a polypeptide of the invention (see U.S. Pat. No. 4,946,778). In addition, methods can be adapted for the construction of Fab expression libraries (Huse, et al., *Science* 246:1275-1281 (1989)) to allow rapid and effective identification of monoclonal Fab fragments with the desired specificity for the Notch2 receptor, or derivatives, fragments, or homologs thereof. Antibody fragments that contain the idiotypes to a polypeptide of the invention can be produced by techniques in the art including, but not limited to: (a) an F(ab')2 fragment produced by pepsin digestion of an antibody molecule; (b) an Fab fragment generated by reducing the disulfide bridges of an F(ab')2 fragment, (c) an Fab fragment generated by the treatment of the antibody molecule with papain and a reducing agent, and (d) Fv fragments.

It can further be desirable, especially in the case of antibody fragments, to modify an antibody in order to increase its serum half-life. This can be achieved, for example, by incorporation of a salvage receptor binding epitope into the antibody fragment by mutation of the appropriate region in the antibody fragment or by incorporating the epitope into a peptide tag that is then fused to the antibody fragment at either end or in the middle (e.g., by DNA or peptide synthesis).

Heteroconjugate antibodies are also within the scope of the present invention. Heteroconjugate antibodies are composed of two covalently joined antibodies. Such antibodies have, for example, been proposed to target immune cells to unwanted cells (U.S. Pat. No. 4,676,980). It is contemplated that the antibodies can be prepared in vitro using known methods in synthetic protein chemistry, including those involving crosslinking agents. For example, immunotoxins can be constructed using a disulfide exchange reaction or by forming a thioether bond. Examples of suitable reagents for this purpose include iminothiolate and methyl-4-mercaptobutyrimidate.

For the purposes of the present invention, it should be appreciated that modified antibodies can comprise any type of variable region that provides for the association of the antibody with the polypeptides of human Notch2. In this regard, the variable region can comprise or be derived from any type of mammal that can be induced to mount a humoral response and generate immunoglobulins against the desired tumor associated antigen. As such, the variable region of the modified antibodies can be, for example, of human, murine, non-human primate (e.g. cynomolgus monkeys, macaques, etc.) or lupine origin. In some embodiments both the variable and constant regions of the modified immunoglobulins are human. In other embodiments the variable regions of compatible antibodies (usually derived from a non-human source) can be engineered or specifically tailored to improve the binding properties or reduce the immunogenicity of the molecule. In this respect, variable regions useful in the present invention can be humanized or otherwise altered through the inclusion of imported amino acid sequences.

The variable domains in both the heavy and light chains are altered by at least partial replacement of one or more CDRs and, if necessary, by partial framework region replacement and sequence changing. Although the CDRs can be derived from an antibody of the same class or even subclass as the antibody from which the framework regions are derived, it is envisaged that the CDRs will be derived from an antibody of different class and preferably from an antibody from a different species. It may not be necessary to replace all of the CDRs with the complete CDRs from the donor variable region to transfer the antigen binding capacity of one variable domain to another. Rather, it may only be necessary to transfer those residues that are necessary to maintain the activity of the antigen binding site. Given the explanations set forth in U.S. Pat. Nos. 5,585,089, 5,693,761 and 5,693,762, it will be well within the competence of those skilled in the art, either by carrying out routine experimentation or by trial and error testing to obtain a functional antibody with reduced immunogenicity.

Alterations to the variable region notwithstanding, those skilled in the art will appreciate that the modified antibodies of this invention will comprise antibodies, or immunoreactive fragments thereof, in which at least a fraction of one or more of the constant region domains has been deleted or otherwise altered so as to provide desired biochemical characteristics such as increased tumor localization or reduced serum half-life when compared with an antibody of approximately the same immunogenicity comprising a native or unaltered constant region. In some embodiments, the constant region of the modified antibodies will comprise a human constant region. Modifications to the constant region compatible with this invention comprise additions, deletions or substitutions of one or more amino acids in one or more domains. That is, the modified antibodies disclosed herein can comprise alterations or modifications to one or more of the three heavy chain constant domains (CH1, CH2 or CH3) and/or to the light chain constant domain (CL). In some embodiments of the invention modified constant regions wherein one or more domains are partially or entirely deleted are contemplated. In some embodiments the modified antibodies will comprise domain deleted constructs or variants wherein the entire CH2 domain has been removed (ΔCH2 constructs). In some embodiments the omitted constant region domain will be replaced by a short amino acid spacer (e.g. 10 residues) that provides some of the molecular flexibility typically imparted by the absent constant region.

Besides their configuration, it is known in the art that the constant region mediates several effector functions. For example, binding of the C1 component of complement to antibodies activates the complement system. Activation of complement is important in the opsonisation and lysis of cell pathogens. The activation of complement also stimulates the inflammatory response and can also be involved in autoimmune hypersensitivity. Further, antibodies bind to cells via the Fc region, with a Fc receptor site on the antibody Fc region binding to a Fc receptor (FcR) on a cell. There are a number of Fc receptors which are specific for different classes of antibody, including IgG (gamma receptors), IgE (eta receptors), IgA (alpha receptors) and IgM (mu receptors). Binding of antibody to Fc receptors on cell surfaces triggers a number of important and diverse biological responses including engulfment and destruction of antibody-coated particles, clearance of immune complexes, lysis of antibody-coated target cells by killer cells (called antibody-dependent cell-mediated cytotoxicity, or ADCC), release of inflammatory mediators, placental transfer and control of immunoglobulin production. Although various Fc receptors and receptor sites have been studied to a certain extent, there is still much which is unknown about their location, structure and functioning.

While not limiting the scope of the present invention, it is believed that antibodies comprising constant regions modified as described herein provide for altered effector functions that, in turn, affect the biological profile of the administered antibody. For example, the deletion or inactivation (through point mutations or other means) of a constant region domain may reduce Fc receptor binding of the circulating modified antibody thereby increasing tumor localization. In other cases it may be that constant region modifications, consistent with this invention, moderate complement binding and thus reduce the serum half life and nonspecific association of a conjugated cytotoxin. Yet other modifications of the constant region can be used to eliminate disulfide linkages or oligosaccharide moieties that allow for enhanced localization due to increased antigen specificity or antibody flexibility. Similarly, modifications to the constant region in accordance with this invention can easily be made using well known biochemical or molecular engineering techniques well within the purview of the skilled artisan.

It will be noted that the modified antibodies can be engineered to fuse the CH3 domain directly to the hinge region of the respective modified antibodies. In other constructs it may be desirable to provide a peptide spacer between the hinge region and the modified CH2 and/or CH3 domains. For example, compatible constructs could be expressed wherein the CH2 domain has been deleted and the remaining CH3 domain (modified or unmodified) is joined to the hinge region with a 5-20 amino acid spacer. Such a spacer can be added, for instance, to ensure that the regulatory elements of the constant domain remain free and accessible or that the hinge region remains flexible. However, it should be noted that amino acid spacers can, in some cases, prove to be immunogenic and elicit an unwanted immune response against the construct. Accordingly, any spacer added to the construct be relatively non-immunogenic or, even omitted altogether if the desired biochemical qualities of the modified antibodies can be maintained.

Besides the deletion of whole constant region domains, it will be appreciated that the antibodies of the present invention may be provided by the partial deletion or substitution of a few or even a single amino acid. For example, the mutation of a single amino acid in selected areas of the CH2 domain may be enough to substantially reduce Fc binding and thereby increase tumor localization. Similarly, it may be desirable to simply delete that part of one or more constant region domains that control the effector function (e.g. complement CLQ binding) to be modulated. Such partial deletions of the constant regions can improve selected characteristics of the antibody (serum half-life) while leaving other desirable functions associated with the subject constant region domain intact. Moreover, as alluded to above, the constant regions of the disclosed antibodies can be modified through the mutation or substitution of one or more amino acids that enhances the profile of the resulting construct. In this respect it may be possible to disrupt the activity provided by a conserved binding site (e.g. Fc binding) while substantially maintaining the configuration and immunogenic profile of the modified antibody. Certain embodiments can comprise the addition of one or more amino acids to the constant region to enhance desirable characteristics such as effector function or provide for more cytotoxin or carbohydrate attachment. In such embodiments it can be desirable to insert or replicate specific sequences derived from selected constant region domains.

The present invention further embraces variants and equivalents which are substantially homologous to the chimeric, humanized and human antibodies, or antibody fragments thereof, set forth herein. These can contain, for example, conservative substitution mutations, i.e. the substitution of one or more amino acids by similar amino acids. For example, conservative substitution refers to the substitution of an amino acid with another within the same general class such as, for example, one acidic amino acid with another acidic amino acid, one basic amino acid with another basic amino acid or one neutral amino acid by another neutral amino acid. What is intended by a conservative amino acid substitution is well known in the art.

The invention also pertains to immunoconjugates comprising an antibody conjugated to a cytotoxic agent. Cytotoxic agents include chemotherapeutic agents, growth inhibitory agents, toxins (e.g., an enzymatically active toxin of bacterial, fungal, plant, or animal origin, or fragments thereof), radioactive isotopes (i.e., a radioconjugate), etc. Chemotherapeutic agents useful in the generation of such immunoconjugates include, for example, methotrexate, adriamicin, doxorubicin, melphalan, mitomycin C, chlorambucil, daunorubicin or other intercalating agents. Enzymatically active toxins and fragments thereof that can be used include diphtheria A chain, nonbinding active fragments of diphtheria toxin, exotoxin A chain, ricin A chain, abrin A chain, modeccin A chain, alpha-sarcin, Aleurites fordii proteins, dianthin proteins, Phytolaca americana proteins (PAPI, PAPII, and PAP-S), momordica charantia inhibitor, curcin, crotin, sapaonaria officinalis inhibitor, gelonin, mitogellin, restrictocin, phenomycin, enomycin, and the tricothecenes. In some embodiments, the antibodies can be conjugated to $^{90}$Y, $^{125}$I, $^{131}$I, $^{123}$I, $^{111}$In, $^{105}$Rh, $^{153}$Sm, $^{67}$Cu, $^{67}$Ga, $^{166}$Ho, $^{177}$Lu, radioisotopes, such as $^{186}$Re and $^{188}$Re using anyone of a number of well known chelators or direct labeling. In other embodiments, the disclosed compositions can comprise antibodies coupled to drugs, prodrugs or lymphokines such as interferon. Conjugates of the antibody and cytotoxic agent are made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutareldehyde), bis-azido compounds (such as bis(p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). Conjugates of an antibody and one or more small molecule toxins, such as a calicheamicin, maytansinoids, a trichothene, and CC1065, and the derivatives of these toxins that have toxin activity, can also be used. In some embodiments, the modified antibodies can be complexed with other immunologically active ligands (e.g. antibodies or fragments thereof) wherein the resulting molecule binds to both the neoplastic cell and an effector cell such as a T cell.

Regardless of how useful quantities are obtained, the antibodies of the present invention can be used in any one of a number of conjugated (i.e. an immunoconjugate) or unconjugated forms. Alternatively, the antibodies of this invention can be used in a nonconjugated or "naked" form to harness the subject's natural defense mechanisms including complement-dependent cytotoxicity (CDC) and antibody dependent cellular toxicity (ADCC) to eliminate the malignant cells. The selection of which conjugated or unconjugated modified antibody to use will depend of the type and stage of cancer, use of adjunct treatment (e.g., chemotherapy or external radiation) and patient condition. It will be appreciated that one skilled in the art could readily make such a selection in view of the teachings herein.

The antibodies of the present invention can be assayed for immunospecific binding by any method known in the art. The immunoassays which can be used include, but are not limited to, competitive and non-competitive assay systems using techniques such as BIAcore analysis, FACS analysis, immunofluorescence, immunocytochemistry, Western blots, radioimmunoassays, ELISA, "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, and protein A immunoassays. Such assays are routine and well known in the art (see, e.g., Ausubel et al, eds, 1994, Current Protocols in Molecular Biology, Vol. 1, John Wiley & Sons, Inc., New York, which is incorporated by reference herein in its entirety).

In some embodiments, the immunospecificity of an antibody against a cancer stem cell marker is determined using ELISA. An ELISA assay comprises preparing antigen, coating wells of a 96 well microtiter plate with antigen, adding the antibody against a cancer stem cell marker conjugated to a detectable compound such as an enzymatic substrate (e.g. horseradish peroxidase or alkaline phosphatase) to the well, incubating for a period of time and detecting the presence of the antigen. In some embodiments, the antibody against a cancer stem cell marker is not conjugated to a detectable compound, but instead a second conjugated antibody that recognizes the antibody against a cancer stem cell marker is added to the well. In some embodiments, instead of coating the well with the antigen, the antibody against a cancer stem cell marker can be coated to the well and a second antibody conjugated to a detectable compound can be added following the addition of the antigen to the coated well. One of skill in the art would be knowledgeable as to the parameters that can be modified to increase the signal detected as well as other variations of ELISAs known in the art (see e.g. Ausubel et al, eds, 1994, Current Protocols in Molecular Biology, Vol. 1, John Wiley & Sons, Inc., New York at 11.2.1).

The binding affinity of an antibody to a cancer stem cell marker antigen and the off-rate of an antibody-antigen interaction can be determined by competitive binding assays. One example of a competitive binding assay is a radioimmunoassay comprising the incubation of labeled antigen (e.g. $^3$H or $^{125}$I), or fragment or variant thereof, with the antibody of interest in the presence of increasing amounts of unlabeled antigen followed by the detection of the antibody bound to the labeled antigen. The affinity of the antibody against a cancer stem cell marker and the binding off-rates can be determined from the data by scatchard plot analysis. In some embodiments, BIAcore kinetic analysis is used to determine the binding on and off rates of antibodies against a cancer stem cell marker. BIAcore kinetic analysis comprises analyzing the binding and dissociation of antibodies from chips with immobilized cancer stem cell marker antigens on their surface.

Polynucleotides

In certain embodiments, the present invention also encompasses isolated polynucleotides that encode a polypeptide comprising an antibody, or fragment thereof, against a human Notch receptor. Thus, the term "polynucleotide encoding a polypeptide" encompasses a polynucleotide which includes only coding sequences for the polypeptide as well as a polynucleotide which includes additional coding and/or non-coding sequences. The polynucleotides of the invention can be in the form of RNA or in the form of DNA. DNA includes cDNA, genomic DNA, and synthetic DNA; and can be double-stranded or single-stranded, and if single stranded can be the coding strand or non-coding (anti-sense) strand.

The present invention further relates to variants of the hereinabove described polynucleotides encoding, for example, fragments, analogs, and derivatives. The variant of the polynucleotide can be a naturally occurring allelic variant of the polynucleotide or a non-naturally occurring variant of the polynucleotide. In certain embodiments, the polynucleotide can have a coding sequence which is a naturally occurring allelic variant of the coding sequence of the disclosed polypeptides. As known in the art, an allelic variant is an alternate form of a polynucleotide sequence that have, for example, a substitution, deletion, or addition of one or more nucleotides, which does not substantially alter the function of the encoded polypeptide.

In certain embodiments the polynucleotides comprise the coding sequence for the mature polypeptide fused in the same reading frame to a polynucleotide which aids, for example, in expression and secretion of a polypeptide from a host cell (e.g. a leader sequence which functions as a secretory sequence for controlling transport of a polypeptide from the cell). The polypeptide having a leader sequence is a preprotein and can have the leader sequence cleaved by the host cell to form the mature form of the polypeptide. The polynucleotides can also encode for a proprotein which is the mature protein plus additional 5' amino acid residues. A mature protein having a prosequence is a proprotein and is an inactive form of the protein. Once the prosequence is cleaved an active mature protein remains.

In certain embodiments the polynucleotides comprise the coding sequence for the mature polypeptide fused in the same reading frame to a marker sequence that allows, for example, for purification of the encoded polypeptide. For example, the marker sequence can be a hexa-histidine tag supplied by a pQE-9 vector to provide for purification of the mature polypeptide fused to the marker in the case of a bacterial host, or the marker sequence can be a hemagglutinin (HA) tag derived from the influenza hemagglutinin protein when a mammalian host (e.g. COS-7 cells) is used.

In certain embodiments, the present invention provides isolated nucleic acid molecules having a nucleotide sequence at least 80% identical, at least 85% identical, at least 90% identical, at least 95% identical, and in some embodiments, at least 96%, 97%, 98% or 99% identical to a polynucleotide encoding a polypeptide comprising an antibody, or fragment thereof, against a human Notch receptor.

By a polynucleotide having a nucleotide sequence at least, for example, 95% "identical" to a reference nucleotide sequence is intended that the nucleotide sequence of the polynucleotide is identical to the reference sequence except that the polynucleotide sequence can include up to five point mutations per each 100 nucleotides of the reference nucleotide sequence. In other words, to obtain a polynucleotide having a nucleotide sequence at least 95% identical to a reference nucleotide sequence, up to 5% of the nucleotides in the reference sequence can be deleted or substituted with another nucleotide, or a number of nucleotides up to 5% of the total nucleotides in the reference sequence can be inserted into the reference sequence. These mutations of the reference sequence can occur at the amino- or carboxy-terminal positions of the reference nucleotide sequence or anywhere between those terminal positions, interspersed either individually among nucleotides in the reference sequence or in one or more contiguous groups within the reference sequence.

As a practical matter, whether any particular nucleic acid molecule is at least 80% identical, at least 85% identical, at least 90% identical, and in some embodiments, at least 95%, 96%, 97%, 98%, or 99% identical to a reference sequence can be determined conventionally using known computer programs such as the Bestfit program (Wisconsin Sequence Analysis Package, Version 8 for Unix, Genetics Computer Group, University Research Park, 575 Science Drive, Madison, Wis. 53711). Bestfit uses the local homology algorithm of Smith and Waterman, Advances in Applied Mathematics 2: 482 489 (1981), to find the best segment of homology between two sequences. When using Bestfit or any other sequence alignment program to determine whether a particular sequence is, for instance, 95% identical to a reference sequence according to the present invention, the parameters are set such that the percentage of identity is calculated over the full length of the reference nucleotide sequence and that gaps in homology of up to 5% of the total number of nucleotides in the reference sequence are allowed.

The polynucleotide variants can contain alterations in the coding regions, non-coding regions, or both. In some embodiments the polynucleotide variants contain alterations which produce silent substitutions, additions, or deletions, but do not alter the properties or activities of the encoded polypeptide. In some embodiments, nucleotide variants are produced by silent substitutions due to the degeneracy of the genetic code. Polynucleotide variants can be produced for a variety of reasons, e.g., to optimize codon expression for a particular host (change codons in the human mRNA to those preferred by a bacterial host such as $E.\ coli$).

Polypeptides

The polypeptides of the present invention can be recombinant polypeptides, natural polypeptides, or synthetic polypeptides comprising an antibody, or fragment thereof, against a human Notch receptor. It will be recognized in the art that some amino acid sequences of the invention can be varied without significant effect of the structure or function of the protein. Thus, the invention further includes variations of the polypeptides which show substantial activity or which include regions of an antibody, or fragment thereof, against human Notch receptor protein. Such mutants include deletions, insertions, inversions, repeats, and type substitutions.

The polypeptides and analogs can be further modified to contain additional chemical moieties not normally part of the protein. Those derivatized moieties can improve the solubility, the biological half life or absorption of the protein. The moieties can also reduce or eliminate any desirable side effects of the proteins and the like. An overview for those moieties can be found in REMINGTON'S PHARMACEUTICAL SCIENCES, 20th ed., Mack Publishing Co., Easton, Pa. (2000).

The isolated polypeptides described herein can be produced by any suitable method known in the art. Such methods range from direct protein synthetic methods to constructing a DNA sequence encoding isolated polypeptide sequences and expressing those sequences in a suitable transformed host. In some embodiments, a DNA sequence is constructed using recombinant technology by isolating or synthesizing a DNA sequence encoding a wild-type protein of interest. Optionally, the sequence can be mutagenized by site-specific mutagenesis to provide functional analogs thereof. See, e.g. Zoeller et al., Proc. Nat'l. Acad. Sci. USA 81:5662-5066 (1984) and U.S. Pat. No. 4,588,585.

In some embodiments a DNA sequence encoding a polypeptide of interest would be constructed by chemical synthesis using an oligonucleotide synthesizer. Such oligonucleotides can be designed based on the amino acid sequence of the desired polypeptide and selecting those codons that are favored in the host cell in which the recombinant polypeptide of interest will be produced. Standard methods can be applied to synthesize an isolated polynucleotide sequence encoding an isolated polypeptide of interest. For example, a complete amino acid sequence can be used to construct a back-translated gene. Further, a DNA oligomer containing a nucleotide sequence coding for the particular isolated polypeptide can be synthesized. For example, several small oligonucleotides coding for portions of the desired polypeptide can be synthesized and then ligated. The individual oligonucleotides typically contain 5' or 3' overhangs for complementary assembly.

Once assembled (by synthesis, site-directed mutagenesis or another method), the polynucleotide sequences encoding a particular isolated polypeptide of interest will be inserted into an expression vector and operatively linked to an expression control sequence appropriate for expression of the protein in a desired host. Proper assembly can be confirmed by nucleotide sequencing, restriction mapping, and expression of a biologically active polypeptide in a suitable host. As is well known in the art, in order to obtain high expression levels of a transfected gene in a host, the gene must be operatively linked to transcriptional and translational expression control sequences that are functional in the chosen expression host.

Recombinant expression vectors are used to amplify and express DNA encoding cancer stem cell marker polypeptide fusions. Recombinant expression vectors are replicable DNA constructs which have synthetic or cDNA-derived DNA fragments encoding a cancer stem cell marker polypeptide fusion or a bioequivalent analog operatively linked to suitable transcriptional or translational regulatory elements derived from mammalian, microbial, viral or insect genes. A transcriptional unit generally comprises an assembly of (1) a genetic element or elements having a regulatory role in gene expression, for example, transcriptional promoters or enhancers, (2) a structural or coding sequence which is transcribed into mRNA and translated into protein, and (3) appropriate transcription and translation initiation and termination sequences, as described in detail below. Such regulatory elements can include an operator sequence to control transcription. The ability to replicate in a host, usually conferred by an origin of replication, and a selection gene to facilitate recognition of transformants can additionally be incorporated. DNA regions are operatively linked when they are functionally related to each other. For example, DNA for a signal peptide (secretory leader) is operatively linked to DNA for a polypeptide if it is expressed as a precursor which participates in the secretion of the polypeptide; a promoter is operatively linked to a coding sequence if it controls the transcription of the sequence; or a ribosome binding site is operatively linked to a coding sequence if it is positioned so as to permit translation. Generally, operatively linked means contiguous and, in the case of secretory leaders, means contiguous and in reading frame. Structural elements intended for use in yeast expression systems include a leader sequence enabling extracellular secretion of translated protein by a host cell. Alternatively, where recombinant protein is expressed without a leader or transport sequence, it can include an N-terminal methionine residue. This residue can optionally be subsequently cleaved from the expressed recombinant protein to provide a final product.

The choice of expression control sequence and expression vector will depend upon the choice of host. A wide variety of expression host/vector combinations can be employed. Useful expression vectors for eukaryotic hosts, include, for example, vectors comprising expression control sequences from SV40, bovine papilloma virus, adenovirus and cytomegalovirus. Useful expression vectors for bacterial hosts include known bacterial plasmids, such as plasmids from *Escherichia coli*, including pCR 1, pBR322, pMB9 and their derivatives, wider host range plasmids, such as M13 and filamentous single-stranded DNA phages.

Suitable host cells for expression of a cancer stem cell marker protein include prokaryotes, yeast, insect or higher eukaryotic cells under the control of appropriate promoters. Prokaryotes include gram negative or gram positive organisms, for example *E. coli* or bacilli. Higher eukaryotic cells include established cell lines of mammalian origin as described below. Cell-free translation systems could also be employed. Appropriate cloning and expression vectors for use with bacterial, fungal, yeast, and mammalian cellular hosts are described by Pouwels et al. (Cloning Vectors: A Laboratory Manual, Elsevier, N.Y., 1985), the relevant disclosure of which is hereby incorporated by reference.

Various mammalian or insect cell culture systems are also advantageously employed to express recombinant protein. Expression of recombinant proteins in mammalian cells can be performed because such proteins are generally correctly folded, appropriately modified and completely functional. Examples of suitable mammalian host cell lines include the COS-7 lines of monkey kidney cells, described by Gluzman (Cell 23:175, 1981), and other cell lines capable of expressing an appropriate vector including, for example, L cells, C127, 3T3, Chinese hamster ovary (CHO), HeLa and BHK cell lines. Mammalian expression vectors can comprise nontranscribed elements such as an origin of replication, a suitable promoter and enhancer linked to the gene to be expressed, and other 5' or 3' flanking nontranscribed sequences, and 5' or 3' nontranslated sequences, such as necessary ribosome binding sites, a polyadenylation site, splice donor and acceptor sites, and transcriptional termination sequences. Baculovirus systems for production of heterologous proteins in insect cells are reviewed by Luckow and Summers, Bio/Technology 6:47 (1988).

The proteins produced by a transformed host can be purified according to any suitable method. Such standard methods include chromatography (e.g., ion exchange, affinity and sizing column chromatography), centrifugation, differential solubility, or by any other standard technique for protein purification. Affinity tags such as hexa-histidine, maltose binding domain, influenza coat sequence and glutathione-S-transferase can be attached to the protein to allow easy purification by passage over an appropriate affinity column. Isolated proteins can also be physically characterized using such techniques as proteolysis, nuclear magnetic resonance and x-ray crystallography.

For example, supernatants from systems which secrete recombinant protein into culture media can be first concentrated using a commercially available protein concentration filter, for example, an Amicon or Millipore Pellicon ultrafiltration unit. Following the concentration step, the concentrate can be applied to a suitable purification matrix. Alternatively, an anion exchange resin can be employed, for example, a matrix or substrate having pendant diethylaminoethyl (DEAE) groups. The matrices can be acrylamide, agarose, dextran, cellulose or other types commonly employed in protein purification. Alternatively, a cation exchange step can be employed. Suitable cation exchangers include various insoluble matrices comprising sulfopropyl or carboxymethyl groups. Finally, one or more reversed-phase high performance liquid chromatography (RP-HPLC) steps employing hydrophobic RP-HPLC media, e.g., silica gel having pendant methyl or other aliphatic groups, can be employed to further purify a cancer stem cell protein-Fc composition. Some or all of the foregoing purification steps, in various combinations, can also be employed to provide a homogeneous recombinant protein.

Recombinant protein produced in bacterial culture can be isolated, for example, by initial extraction from cell pellets, followed by one or more concentration, salting-out, aqueous ion exchange or size exclusion chromatography steps. High performance liquid chromatography (HPLC) can be employed for final purification steps. Microbial cells employed in expression of a recombinant protein can be disrupted by any convenient method, including freeze-thaw cycling, sonication, mechanical disruption, or use of cell lysing agents.

Inhibiting Tumor Cell Growth

The present invention provides methods for inhibiting the growth of tumorigenic cells expressing a cancer stem cell marker using the antibodies against a cancer stem cell marker described herein. In certain embodiments, the method of inhibiting the growth of tumorigenic cells expressing a cancer stem cell marker comprises contacting the cell with an antibody against a cancer stem cell marker in vitro. For example, an immortalized cell line or a cancer cell line that expresses a cancer stem cell marker is cultured in medium to which is added an antibody against the expressed cancer stem cell marker to inhibit cell growth. In some embodiments, tumor cells comprising tumor stem cells are isolated from a patient sample such as, for example, a tissue biopsy, pleural effusion, or blood sample and cultured in medium to which is added an antibody against a cancer stem cell marker to inhibit cell growth.

In some embodiments, the method of inhibiting the growth of tumorigenic cells expressing a cancer stem cell marker comprises contacting the cell with an antibody against a cancer stem cell marker in vivo. In certain embodiments, contacting a tumorigenic cell with an antibody against a cancer stem cell marker is undertaken in an animal model. For example, xenografts expressing a cancer stem cell marker are grown in immunocompromised mice (e.g. NOD/SCID mice) that are administered an antibody against a cancer stem cell marker to inhibit tumor growth. In some embodiments, cancer stem cells that express a cancer stem cell marker are isolated from a patient sample such as, for example, a tissue biopsy, pleural effusion, or blood sample and injected into immunocompromised mice that are then administered an antibody against the cancer stem cell marker to inhibit tumor cell growth. In some embodiments, the antibody against a cancer stem cell marker is administered at the same time or shortly after introduction of tumorigenic cells into the animal to prevent tumor growth. In some embodiments, the antibody against a cancer stem cell marker is administered as a therapeutic after the tumorigenic cells have grown to a specified size.

Pharmaceutical Compositions

The present invention further provides pharmaceutical compositions comprising antibodies that target a cancer stem cell marker. These pharmaceutical compositions find use in inhibiting tumor cell growth and treating cancer in human patients.

Formulations are prepared for storage and use by combining a purified antibody of the present invention with a pharmaceutically acceptable vehicle (e.g. carrier, excipient)

(Remington, The Science and Practice of Pharmacy 20th Edition Mack Publishing, 2000). Suitable pharmaceutically acceptable vehicles include, but are not limited to, nontoxic buffers such as phosphate, citrate, and other organic acids; salts such as sodium chloride; antioxidants including ascorbic acid and methionine; preservatives (e.g. octadecyldimethylbenzyl ammonium chloride; hexamethonium chloride; benzalkonium chloride; benzethonium chloride; phenol, butyl or benzyl alcohol; alkyl parabens, such as methyl or propyl paraben; catechol; resorcinol; cyclohexanol; 3-pentanol; and m-cresol); low molecular weight polypeptides (e.g. less than about 10 amino acid residues); proteins such as serum albumin, gelatin, or immunoglobulins; hydrophilic polymers such as polyvinylpyrrolidone; amino acids such as glycine, glutamine, asparagine, histidine, arginine, or lysine; carbohydrates such as monosacchandes, disaccharides, glucose, mannose, or dextrins; chelating agents such as EDTA; sugars such as sucrose, mannitol, trehalose or sorbitol; salt-forming counter-ions such as sodium; metal complexes (e.g. Zn-protein complexes); and non-ionic surfactants such as TWEEN or polyethylene glycol (PEG).

The pharmaceutical composition of the present invention can be administered in any number of ways for either local or systemic treatment. Administration can be topical (such as to mucous membranes including vaginal and rectal delivery) such as transdermal patches, ointments, lotions, creams, gels, drops, suppositories, sprays, liquids and powders; pulmonary (e.g., by inhalation or insufflation of powders or aerosols, including by nebulizer; intratracheal, intranasal, epidermal and transdermal); oral; or parenteral including intravenous, intraarterial, subcutaneous, intraperitoneal or intramuscular injection or infusion; or intracranial (e.g., intrathecal or intraventricular) administration.

The therapeutic formulation can be in unit dosage form. Such formulations include tablets, pills, capsules, powders, granules, solutions or suspensions in water or non-aqueous media, or suppositories for oral, parenteral, or rectal administration or for administration by inhalation. In solid compositions such as tablets the principal active ingredient is mixed with a pharmaceutical carrier. Conventional tableting ingredients include corn starch, lactose, sucrose, sorbitol, talc, stearic acid, magnesium stearate, dicalcium phosphate or gums, and other diluents (e.g. water) to form a solid preformulation composition containing a homogeneous mixture of a compound of the present invention, or a non-toxic pharmaceutically acceptable salt thereof. The solid preformulation composition is then subdivided into unit dosage forms of the type described above. The tablets, pills, etc of the novel composition can be coated or otherwise compounded to provide a dosage form affording the advantage of prolonged action. For example, the tablet or pill can comprise an inner composition covered by an outer component. Furthermore, the two components can be separated by an enteric layer that serves to resist disintegration and permits the inner component to pass intact through the stomach or to be delayed in release. A variety of materials can be used for such enteric layers or coatings, such materials including a number of polymeric acids and mixtures of polymeric acids with such materials as shellac, cetyl alcohol and cellulose acetate.

Pharmaceutical formulations include antibodies of the present invention complexed with liposomes (Epstein, et al., 1985, *Proc. Natl. Acad. Sci. USA* 82:3688; Hwang, et al., 1980, *Proc. Natl. Acad. Sci. USA* 77:4030; and U.S. Pat. Nos. 4,485,045 and 4,544,545). Liposomes with enhanced circulation time are disclosed in U.S. Pat. No. 5,013,556. Some liposomes can be generated by the reverse phase evaporation with a lipid composition comprising phosphatidylcholine, cholesterol, and PEG-derivatized phosphatidylethanolamine (PEG-PE). Liposomes are extruded through filters of defined pore size to yield liposomes with the desired diameter.

The antibodies can also be entrapped in microcapsules. Such microcapsules are prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions as described in Remington, The Science and Practice of Pharmacy 20th Ed. Mack Publishing (2000).

In addition sustained-release preparations can be prepared. Suitable examples of sustained-release preparations include semipermeable matrices of solid hydrophobic polymers containing the antibody, which matrices are in the form of shaped articles (e.g. films, or microcapsules). Examples of sustained-release matrices include polyesters, hydrogels such as poly (2-hydroxyethyl-methacrylate) or poly(vinylalcohol), polylactides (U.S. Pat. No. 3,773,919), copolymers of L-glutamic acid and 7 ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), sucrose acetate isobutyrate, and poly-D-(−)-3-hydroxybutyric acid.

Treatment and Combination Therapy

In some embodiments, the treatment involves the combined administration of an antibody of the present invention and a chemotherapeutic agent or cocktail of multiple different chemotherapeutic agents. Treatment with an antibody can occur prior to, concurrently with, or subsequent to administration of chemotherapies. Chemotherapies contemplated by the invention include chemical substances or drugs which are known in the art and are commercially available, such as Doxorubicin, 5-Fluorouracil, Cytosine arabinoside ("Ara-C"), Cyclophosphamide, Thiotepa, Busulfan, Cytoxin, Taxol, Methotrexate, Cisplatin, Melphalan, Vinblastine and Carboplatin. Combined administration can include co-administration, either in a single pharmaceutical formulation or using separate formulations, or consecutive administration in either order but generally within a time period such that all active agents can exert their biological activities simultaneously. Preparation and dosing schedules for such chemotherapeutic agents can be used according to manufacturers' instructions or as determined empirically by the skilled practitioner. Preparation and dosing schedules for such chemotherapy are also described in Chemotherapy Service Ed., M. C. Perry, Williams & Wilkins, Baltimore, Md. (1992).

In other embodiments, the treatment involves the combined administration of an antibody of the present invention and radiation therapy. Treatment with the antibody can occur prior to, concurrently with, or subsequent to administration of radiation therapy. Any dosing schedules for such radiation therapy can be used as determined by the skilled practitioner.

In other embodiments, the treatment can involve the combined administration of antibodies of the present invention with other antibodies against additional tumor associated antigens including, but not limited to, antibodies that bind to the EGF receptor (EGFR) (Erbitux®), the erbB2 receptor (HER2) (Herceptin®), and vascular endothelial growth factor (VEGF) (Avastin®). Furthermore, treatment can include administration of one or more cytokines, can be accompanied by surgical removal of cancer cells or any other therapy deemed necessary by a treating physician.

For the treatment of the disease, the appropriate dosage of an antibody of the present invention depends on the type of disease to be treated, the severity and course of the disease, the responsiveness of the disease, whether the antibody is administered for therapeutic or preventative purposes, previous therapy, patient's clinical history, and so on all at the discretion of the treating physician. The antibody can be administered one time or over a series of treatments lasting from several days to several months, or until a cure is effected or a diminution of the disease state is achieved (e.g. reduction in tumor size). Optimal dosing schedules can be calculated from measurements of drug accumulation in the body of the patient and will vary depending on the relative potency of an individual antibody. The administering physician can easily determine optimum dosages, dosing methodologies and repetition rates. In general, dosage is from 0.01 µg to 100 mg per kg of body weight, and can be given once or more daily, weekly, monthly or yearly. The treating physician can estimate repetition rates for dosing based on measured residence times and concentrations of the drug in bodily fluids or tissues.

The present invention provides kits comprising the antibodies described herein and that can be used to perform the methods described herein. In certain embodiments, a kit comprises at least one purified antibody against a cancer stem cell marker in one or more containers. In some embodiments, the kits contain all of the components necessary and/or sufficient to perform a detection assay, including all controls, directions for performing assays, and any necessary software for analysis and presentation of results. One skilled in the art will readily recognize that the disclosed antibodies of the present invention can be readily incorporated into one of the established kit formats which are well known in the art.

Embodiments of the present disclosure can be further defined by reference to the following examples, which describe in detail preparation of antibodies of the present disclosure and methods for using antibodies of the present disclosure. It will be apparent to those skilled in the art that many modifications, both to materials and methods, can be practiced without departing from the scope of the present disclosure. Wherever possible, the same reference numbers will be used throughout the drawings to refer to the same or like parts. As used herein and in the appended claims, the singular forms "a," "or," and "the" include plural referents unless the context clearly dictates otherwise. Thus, for example, reference to "an antibody" includes a plurality of such antibodies or one or more antibodies and equivalents thereof known to those skilled in the art. Furthermore, all numbers expressing quantities of ingredients, reaction conditions, purity, polypeptide and polynucleotide lengths, and so forth, used in the specification, are modified by the term "about," unless otherwise indicated. Accordingly, the numerical parameters set forth in the specification and claims are approximations that can vary depending upon the desired properties of the present invention. All of the various embodiments or options described herein can be combined in any and all variations.

EXAMPLES

Example 1

Defining a Conserved Notch Receptor Ligand Binding Region

This example describes the discovery of a conserved ligand binding region within the Notch family of receptors. This ligand binding region comprises a conserved glutamate within EGF11, or its equivalent, that is necessary for ligand binding.

Notch receptors interact with their ligands via a ligand binding domain comprising two of the thirty-six EGF repeats within the extracellular domain. Specifically, EGF repeats 11 and 12 of the Notch receptor family (EGF10-11 in Notch3) define a domain that is both necessary and sufficient to mediate ligand binding (Rebay et al., 1991, Cell 67:687-99; U.S. Pat. Nos. 5,786,158, 6,090,922). Optimal binding, however, requires the participation of additional EGF repeats as well as glycosylation, including within EGF11-12 (Xu et al., *J. Biol. Chem.* 280: 30158-65).

To further define the region within the EGF11-12 domain required for ligand binding, sequence comparison between Notch receptor EGF repeats was conducted. This analysis revealed a conserved glutamate (E) within EGF11 of human Notch1, Notch2, Notch3 (homologous EGF10), and Notch4 but not in any of the other thirty-six EGF repeats in these proteins (FIG. 1). Furthermore, this glutamate was found to also be conserved in EGF11 of both *Drosophila* and *Xenopus* Notch, but again in no other EGF repeats, as well as conserved in a single EGF repeat (EGF9) of *C. elegans* Notch (FIG. 1). X-ray crystallography data show this glutamate on the surface of the folded EGF11 repeat (Hambleton et al., 2004, *Structure*, 12: 217-83), thus together these data indicate an important role for this conserved glutamate residue in ligand binding by EGF11.

To demonstrate such a role, glutamate 424 in EGF11 of Notch1 was replaced with the charge variant glutamine (Q) using standard recombinant DNA technology techniques and the ability of the mutated receptor (E424Q) to bind Notch receptor ligands was tested. Full-length wild type Notch1 or Notch1 E424Q was co-transfected with GFP into HEK 293 cells. Twenty-four hours post transfection, either Jagged1 or DLL4 protein was added to the cells and binding was assessed using FACS. GFP expression marked cells expressing Notch1 protein (FIG. 2, x-axis). Cells expressing wild type Notch1 bound both DLL4 (FIG. 2, top left box) and Jagged1 (FIG. 2, bottom left box). In contrast, significantly fewer cells expressing Notch1 E424Q showed any binding to either DLL4 (FIG. 2, top right box) or Jagged1 (FIG. 2, bottom right box).

In analogous experiments with the human Notch2 receptor, glutamate 428 of EGF 11 was replaced with the charge variant glutamine (Q) using standard recombinant DNA technology techniques and the ability of the mutated receptor (E428Q) to bind Notch receptor ligands was tested. Cells expressing wild type Notch2 bound both DLL4 (FIG. 3, top left box) and Jagged1 (FIG. 3, bottom left box). In contrast, significantly fewer cells expressing Notch2 E428Q showed any binding to either DLL4 (FIG. 3, top right box) or Jagged1 (FIG. 3, bottom right box).

To further assess the necessity of glutamate 424 in ligand binding by Notch1 EGF11 and glutamate 428 in ligand binding by Notch2 EGF11, additional mutations in this conserved glutamate are generated. Using standard recombinant DNA technology, this conserved glutamate in EGF11 is replaced with other charge variant amino acids, including, for example, arginine and asparagine, as well as with a charge equivalent amino acid, aspartate. Mutated full-length Notch receptors are then co-transfected into HEK 293 cells with GFP and binding to ligands Jagged1 and DLL4 is assessed by FACS as described above. The necessity of this conserved glutamate in the EGF11 repeat of human Notch4 and in the EGF10 repeat of human Notch3 is similarly assessed.

Similar mutagenesis experiments are used to determine the necessity of other amino acids in defining a ligand binding region in the human Notch receptors. For example, in certain embodiments, individual mutations are made in the amino acids surrounding this conserved glutamate and the effect of these mutations on ligand binding is assessed. In this manner a conserved Notch receptor ligand binding region within EGF 11 comprising the conserved glutamate residue is defined.

Example 2

Antibodies Targeting a Notch Receptor Ligand Binding Region

Based on the identification of a conserved Notch receptor ligand binding region, antagonists targeting the conserved glutamate residue in EGF11 (EGF10 of Notch3) are generated as therapeutics against diseases, including cancer, driven by Notch receptor signaling. In certain embodiments, antibodies that specifically recognize a Notch glutamate ligand binding region were generated.

Antigen Production

In certain embodiments, a recombinant polypeptide fragment of EGF11 of a human Notch receptor (or EGF10 of Notch3) is generated as an antigen for antibody production. Standard recombinant DNA technology is used to isolate a polynucleotide encoding, for example, amino acids 411-446 of Notch1. This polynucleotide is ligated in-frame N-terminal to a human Fc-tag and cloned into a transfer plasmid vector for baculovirus mediated expression in insect cells. Standard transfection, infection, and cell culture protocols are used to produce recombinant insect cells expressing the corresponding Notch1 EGF11 polypeptide (O'Reilley et al., *Baculovirus expression vectors: A Laboratory Manual*, Oxford: Oxford University Press (1994)).

In certain embodiments, a polypeptide of the glutamate ligand binding domain surrounding the conserved glutamate is generated. In some embodiments, the polypeptide is generated using the sequence of a specific human Notch receptor. For example, in some embodiments, the polypeptide PCE-HAGKCVNT (SEQ ID NO: 21) from Notch1 EGF11 can be used to generate antibodies targeting the ligand binding region. In some embodiments, the polypeptide PCE-HAGKCVNT (SEQ ID NO: 22) from Notch2 EGF11 can be used to generate antibodies targeting the ligand binding region. In some embodiments, the polypeptide PCE-HLGRCVNT (SEQ ID NO: 23) from Notch3 EGF10 can be used to generate antibodies targeting the ligand binding region. In some embodiments, the polypeptide PCE-HGGSCLNT (SEQ ID NO: 24) from Notch4 EGF11 can be used to generate antibodies targeting the ligand binding region. In certain embodiments, the polypeptide is generated so as to contain the maximum number of amino acids between the maximum number of Notch receptors and with non-conserved amino acids optimized by charge matching in an effort to generate antibodies recognizing the glutamate ligand binding region of multiple Notch receptors. In certain embodiments, the polypeptide issued to generate antibodies targeting the Notch receptor ligand binding region is NPCEHXG-ZCXNX (SEQ ID NO: 27), where X is a non-polar, aliphatic amino acid residue and Z is a positively charged amino acid residue. In some embodiments, the polypeptide QPCE-HAGRCANT (SEQ ID NO: 28) is used to generate antibodies targeting the ligand binding domain.

Immunization

Following antigen generation, mice (n=3) are immunized with either purified Notch glutamate ligand binding region antigen protein or a synthetic peptide using standard techniques. Blood from individual mice is screened approximately 70 days after initial immunization for antigen recognition using ELISA and FACS analysis (described in detail below). The two animals with the highest antibody titers are selected for final antigen boost after which spleen cells are isolated for hybridoma production. Hybridoma cells are plated at 1 cell per well in 96 well plates, and the supernatant from each well screened by ELISA and FACS analysis against antigen protein. Several hybridomas with high antibody titer are selected and scaled up in static flask culture. Antibodies are purified from the hybridoma supernatant using protein A or protein G agarose chromatography. Purified monoclonal antibodies are again tested by FACS and are isotyped to select for IgG and IgM antibodies.

FACS Analysis

To select monoclonal antibodies produced by hybridomas clones that recognize the native Notch ligand binding region, FACS analysis is used. HEK 293 cells are co-transfected with expression vectors encoding a full-length cDNA clone of Notch1, Notch2, Notch3, or Notch4 and the transfection marker GFP. Twenty-four to forty-eight hours post-transfection, cells are collected in suspension and incubated on ice with anti-Notch glutamate ligand binding region antibodies or control IgG to detect background antibody binding. The cells are washed and primary antibodies detected with anti-mouse secondary antibodies conjugated to a fluorescent chromophore. Labeled cells are then sorted by FACS to identify anti-Notch glutamate ligand binding antibodies that specifically recognize cell surface expression of one or more native cell-surface Notch receptor proteins.

The ability of antibodies directed against a Notch glutamate ligand binding region to interfere with the interaction between Notch and its ligands, Jagged1 and DLL4, is next determined. HEK 293 cells expressing full length Notch protein are incubated with either DLL4-Fc or Jagged1-Fc in the presence of anti-Notch glutamate ligand binding region antibodies or control antibodies. Binding of Fc fusion proteins to cells expressing a Notch receptor is detected by PE-conjugated goat anti-Fc antibody and flow cytometry. The ability of anti-Notch glutamate ligand binding region antibodies to inhibit the binding of Notch to DLL4 or Jagged1 is thus determined by a changed in fluorescence intensity.

Chimeric Antibodies

After monoclonal antibodies that specifically recognize a Notch ligand binding region are identified, these antibodies are modified to overcome the human anti-mouse antibody (HAMA) immune response when rodent antibodies are used as therapeutics agents. The variable regions of the heavy-chain and light-chain of the selected monoclonal antibody are isolated by RT-PCR from hybridoma cells and ligated in-frame to human IgG1 heavy-chain and kappa light chain constant regions, respectively, in mammalian expression vectors. Alternatively a human Ig expression vector such as TCAE 5.3 is used that contains the human $IgG_1$ heavy-chain and kappa light-chain constant region genes on the same plasmid (Preston et al., 1998, *Infection & Immunity* 66:4137-42). Expression vectors encoding chimeric heavy- and light-chains are then co-transfected into Chinese hamster ovary (CHO) cells for chimeric antibody production. Immunoreactivity and affinity of chimeric antibodies are compared to parental murine antibodies by ELISA and FACS.

Humanized Antibodies

As chimeric antibody therapeutics are still frequently antigenic, producing a human anti-chimeric antibody (HACA) immune response, chimeric antibodies against anti-Notch ligand binding region can undergo further humanization. To generate humanized antibodies the three short hypervariable sequences, or complementary determining regions (CDRs), of the chimeric antibody heavy- and light-chain variable domains described above are engineered using recombinant DNA technology into the variable domain framework of a human heavy- and light-chain sequences, respectively, and then cloned into a mammalian expression vector for expression in CHO cells. The immunoreactivity and affinity of the humanized antibodies are compared to parental chimeric antibodies by ELISA and FACS. Additionally, site-directed or high-density mutagenesis of the variable region can be used to optimize specificity, affinity, etc. of the humanized antibody.

Human Antibodies

In certain embodiments, human antibodies that specifically recognize a Notch glutamate ligand binding region were isolated using phage display. A synthetic antibody library containing human antibody variable domains is panned for specific and high affinity recognition of the Notch ligand binding region by using either a ligand binding region protein from a specific Notch receptor or the generic polypeptide to the ligand region described in detail above. In some embodiments, polypeptides with and without a mutation in the conserved glutamate are used; the peptide with the mutated glutamate residue is used to remove antibodies that recognize regions outside of the glutamate necessary for ligand binding with the remaining antibodies then recognizing only the wild type synthetic peptide. CDR cassettes in the library are then specifically exchanged via unique flanking restriction sites for antibody optimization for binding to the glutamate-containing peptide. Optimized human variable regions are then cloned into an Ig expression vector containing human IgG$_1$ heavy-chain and kappa light-chain for expression of human antibodies in CHO cells.

In certain embodiments, phage display identified a specific fAb that binds to the ligand binding domain within Notch1. In certain embodiments, phage display identified a specific fAb that binds to the ligand binding domain within Notch3. In certain embodiments, a fAb was discovered that bound to the ligand binding domain of both Notch3 and Notch1. In certain embodiments, $2 \times 10^{13}$ Fab displaying phage particles from a human fAb phage library were incubated with cells expressing full length recombinant protein or passively immobilized recombinant protein fragments, non-specific phage were washed off, and then specific phage were eluted with either low pH (cells) or DTT (recombinant protein). The eluted output was used to infect TG1 F+ bacteria, rescued with helper phage, and then Fab display induced with IPTG (0.25 mM). The output of this rescued round one served as the starting point for further selections in rounds two, three, four, and five as indicated in Table 1.

Notch ligand binding region (substitution E424Q). The lead fAb bound only to the selected antigen and not Notch1 (E424Q).

To confirm that the lead Notch1 fAb was specific for the ligand binding region of Notch1, HEK293 cells were co-transfected with GFP and either wild type full length Notch1 or Notch1 containing the amino acid substitution E424Q. As shown in FIG. 4, the lead Notch1 fAb demonstrates robust binding to Notch1 expressing cells, but failed to bind to cells overexpressing Notch1 protein with the E424Q amino acid substitution.

To identify high affinity mAbs, affinity maturation of the Notch1 lead fAb specific for the ligand binding region of Notch1 was performed. This was accomplished through the use of phage display to identify a series of alternative light chains which provided greater affinity for Notch1 than the parental fAb. Affinity maturation identified 90R21, 90R22, and 90R29 anti-Notch1 ligand binding domain antibodies. The 90R21 heavy chain comprises the amino acids of SEQ ID NO: 1, including CDR1 (SEQ ID NO: 2); CDR2 (SEQ ID NO: 3) and CDR3 (SEQ ID NO: 4). The 90R21 light chain comprises the amino acids of SEQ ID NO: 5, including CDR1 (SEQ ID NO: 6); CDR2 (SEQ ID NO: 7) and CDR3 (SEQ ID NO: 8). 90R21 was deposited with ATCC on Feb. 1, 2008 (deposit No. PTA-8909).

For Notch3, the phage display library was panned for binding to the analogous epitope within Notch3 (comprising amino acid 403 of Notch 3) using similar approach for as Notch 1. Human protein selections did not yield fAbs that bound the E403Q epitope, thus murine protein selection was used. The lead fAb, 122R5, bound human and murine Notch3 only to the selected antigen and not Notch3 (E403Q). The 122R5 heavy chain comprises the amino acids of SEQ ID NO: 9, including CDR1 (SEQ ID NO: 10); CDR2 (SEQ ID NO: 11) and CDR3 (SEQ ID NO: 12). The 122R5 light chain comprises the amino acids of SEQ ID NO: 13, including CDR1 (SEQ ID NO: 14); CDR2 (SEQ ID NO: 15) and CDR3 (SEQ ID NO: 16). The fAb122R5 also demonstrated the ability to bind to Notch1, but not to Notch 1(E424Q), demonstrating that it was possible to identify antibodies that bind to the critical ligand binding region of multiple Notch family members (FIG. 5).

Example 3

In Vitro Assays to Evaluate Anti-Notch Glutamate Ligand Binding Region Antibodies This example describes representative in vitro assays to test the activity of antibodies generated against a Notch receptor glutamate ligand binding region on cell proliferation, Notch pathway activation, and cytotoxicity.

Binding Assay

The ability of antibodies specific for the critical ligand binding region to inhibit binding of Notch ligands to Notch

TABLE 1

| | Selected Antigen* | | | | |
|---|---|---|---|---|---|
| fAb | R1 | R2 | R3 | R4 | R5 |
| Anti-Notch1 | hNotch1(EGF10-15)Fc | hNotch1(EGF10-15)Fc | Cells | Cells | Cells |
| Anti-Notch3 | mNotch3(EGF9-14)Fc | mNotch3(EGF9-14)Fc | mNotch3(EGF9-14)Fc | | |

*Note:
h, human; m, mouse was evaluated. In certain embodiments, the ability of a panel of affinity matured monoclonal antibodies specific for the Notch1 ligand binding region to inhibit binding of DLL4 to Notch1 was determined by FACS analysis (FIG. 6). HEK293 cells stably transfected with human Notch1 were incubated with soluble DLL4-fc fusion protein in the presence of increasing concentrations of 90R21, 90R22, and 90R29 antibodies. All three monoclonal antibodies blocked the binding between DLL4 and Notch1 overexpressing cells. Furthermore, the distinct fAb identified as binding to the analogous epitope within Notch3 (comprising amino acid 403 of Notch 3) also potently blocked the binding of Notch ligands to Notch 3 (FIG. 7). HEK293 cells co-transfected with GFP and full length Notch3 were incubated with a soluble human Jag1-fc fusion protein in the absence (No Ab) or presence (122R03E1) of the fAb. The fAb blocked the binding between Jag1 and Notch3 overexpressing cells. These data indicate that antibodies to this critical ligand binding region potently impact binding of Notch ligands to Notch receptors.

Proliferation Assay

The expression of Notch receptors by different cancer cell lines is quantified using Taqman analysis. Cell lines identified as expressing Notch are plated at a density of $10^4$ cell per well in 96-well tissue culture microplates and allowed to spread for 24 hours. Subsequently cells are cultured for an additional 12 hours in fresh DMEM with 2% FCS at which point anti-Notch ligand binding region or control antibodies are added to the culture medium in the presence of 10 μmol/L BrdU. Following BrdU labeling, the culture media is removed, and the cells fixed at room temperature for 30 minutes in ethanol and reacted for 90 minutes with peroxidase-conjugated monoclonal anti-BrdU antibody (clone BMG 6H8, Fab fragments). The substrate is developed in a solution containing tetramethylbenzidine and stopped after 15 minutes with 25 μl of 1 mol/L $H_2SO_4$. The color reaction is measured with an automatic ELISA plate reader using a 450 nm filter (UV Microplate Reader; Bio-Rad Laboratories, Richmond, Calif.). All experiments are performed in triplicate. The ability of anti-Notch ligand binding region antibodies to inhibit cell proliferation compared to control antibodies is determined.

Pathway Activation Assays

In certain embodiments, the ability of antibodies against a Notch ligand binding region to block activation of the Notch signaling pathway is determined in vitro. HEK 293 cells cultured in DMEM supplemented with antibiotics and 10% FCS are co-transfected with 1) Hes1-Luc reporter vector containing the Hes1 promoter upstream of a firefly luciferase reporter gene to measure Notch signaling levels (Jarriault et al., 1995, *Nature* 377:355-8) in response to DLL4 ligand; 2) a *Renilla luciferase* reporter (Promega; Madison, Wis.) as an internal control for transfection efficiency; and 3) an expression vector encoding full-length Notch receptor. Transfected cells are then incubated with 10 μg/ml DLL4-Fc protein in the presence or absence of antibodies against a Notch ligand binding region. Forty-eight hours following transfection, luciferase levels are measured using a dual luciferase assay kit (Promega; Madison, Wis.) with firefly luciferase activity normalized to *Renilla luciferase* activity. The ability of antibodies to inhibit DLL4 induced Notch pathway activation is thus determined.

Figure 8B:
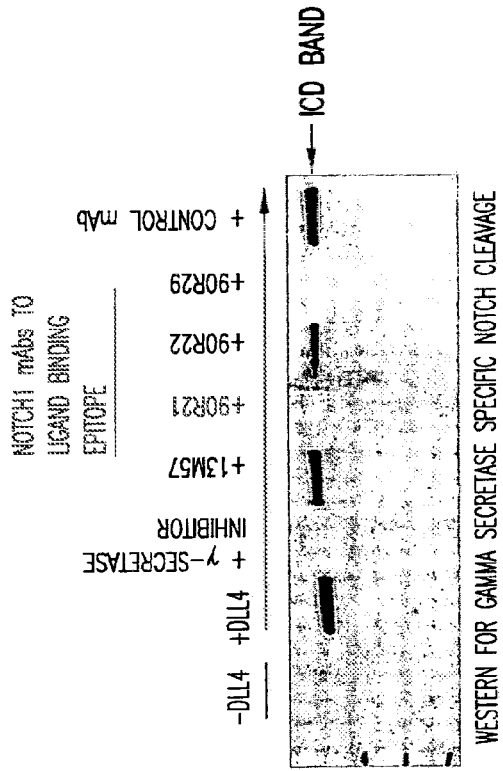
Figure 8A:
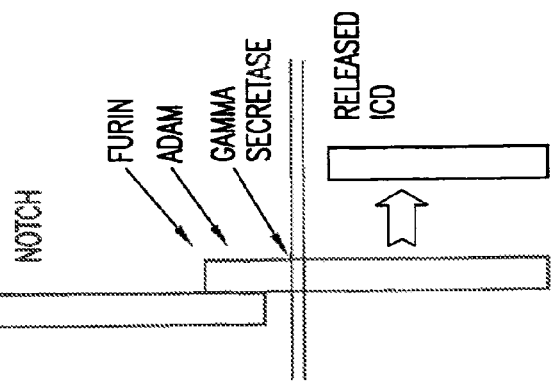

In certain embodiments, the ability of antibodies against a Notch ligand binding region to block Notch signaling was measured by inhibition of Notch cleavage in response to ligand stimulation. Hela cells stably expressing Notch1 were cultured in DMEM supplemented with antibiotics and 10% FCS. Cells were then incubated in the presence of 10 ug/ml soluble DLL4-Fc protein in the presence or absence of monoclonal antibodies against a Notch ligand binding domain, control antibodies, antibodies against Notch1 binding outside the ligand binding region (13M57), and gamma secretase inhibitor DBZ. Cells were harvested and cell lysates analyzed by western blot using an antibody that recognizes the cleaved intracellular domain (ICD) of Notch generated in response to ligand induced signaling (FIG. 8A). As shown in FIG. 8B, antibodies to the ligand binding region (90R21, 90R22, and 90R29) prevented formation of Notch ICD in response to Notch ligand similar to gamma secretase inhibitor DBZ. In contrast, 13M57 and control antibodies had no affect on formation of the ICD in response to DLL4.

Complement-Dependent Cytotoxicity Assay

In certain embodiments, cancer cell lines expressing one or more Notch receptors or cancer stem cells isolated from a patient sample passaged as a xenograft in immunocompromised mice (as described in detail below) are used to measure complement dependent cytotoxicity (CDC) mediated by an antibody against a Notch ligand binding region. Cells are suspended in 200 μl RPMI 1640 culture medium supplemented with antibiotics and 5% FBS at $10^6$ cells/ml. Suspended cells are then mixed with 200 μl serum or heat-inactivated serum with antibodies against Notch2 or control antibodies in triplicate. Cell mixtures are incubated for 1 to 4 hours at 37° C. in 5% $CO_2$. Treated cells are then collected, resuspended in 100 μl FITC-labeled annexin V diluted in culture medium and incubated at room temperature for 10 minutes. One hundred microliters of a propidium iodide solution (25 μg/ml) diluted in HBSS is added and incubated for 5 minutes at room temperature. Cells are collected, resuspended in culture medium and analyzed by flow cytometry. Flow cytometry of FITC stained cells provides total cell counts, and propidium iodide uptake by dead cells as a percentage of total cell numbers is used to measure cell death in the presence of serum and antibodies against Notch2 compared to heat-inactivated serum and control antibodies. The ability of anti-Notch ligand binding region antibodies to mediated complement-dependent cytotoxicity is thus determined.

Antibody-Dependent Cellular Cytotoxicity Assay

In certain embodiments, cancer cell lines expressing one or more Notch receptors or cancer stem cells isolated from a patients sample passaged as a xenograft in immunocompromised mice (as described in detail below) are used to measure antibody dependent cellular cytotoxicity (ADCC) mediated by an antibody against a Notch ligand binding region. Cells are suspended in 200 μl phenol red-free RPMI 1640 culture medium supplemented with antibiotics and 5% FBS at $10^6$ cells/ml. Peripheral blood mononuclear cells (PBMCs) are isolated from heparinized peripheral blood by Ficoll-Paque density gradient centrifugation for use as effector cells. Target cells (T) are then mixed with PBMC effector cells (E) at E/T ratios of 25:1, 10:1, and 5:1 in 96-well plates in the presence of at least one Notch EGF11 antibody or a control antibody. Controls include incubation of target cells alone and effector cells alone in the presence of antibody. Cell mixtures are incubated for 1 to 6 hours at 37° C. in 5% $CO_2$. Released lactate dehydrogenase (LDH), a stable cytosolic enzyme released upon cell lysis, is then measured by a colorimetric assay (CytoTox96 Non-radioactive Cytotoxicity Assay; Promega; Madison, Wis.). Absorbance data at 490 nm are collected with a standard 96-well plate reader and background corrected. The percentage of specific cytotoxicity is calculated according to the formula: % cytotoxicity=100× (experimental LDH release–effector spontaneous LDH release–target spontaneous LDH release)/(target maximal LDH release−target spontaneous LDH release). The ability of antibodies against a Notch ligand binding region to mediated antibody dependent cellular cytotoxicity is thus determined.

Example 4

In Vivo Prevention of Tumor Growth Using Anti-Notch Ligand Binding Region Antibodies This example describes the use of anti-Notch ligand binding region antibodies to prevent tumor growth in a xenograft model. This example also describes the effects of anti-Notch ligand binding region antibody treatment of Notch target gene expression.

In certain embodiments, tumor cells from a patient sample (solid tumor biopsy or pleural effusion) that have been passaged as a xenograft in mice were prepared for repassaging into experimental animals. Tumor tissue was removed under sterile conditions, cut up into small pieces, minced completely using sterile blades, and single cell suspensions obtained by enzymatic digestion and mechanical disruption. Specifically, pleural effusion cells or the resulting tumor pieces were mixed with ultra-pure collagenase III in culture medium (200-250 units of collagenase per mL) and incubated at 37° C. for 3-4 hours with pipetting up and down through a 10-mL pipette every 15-20 minutes. Digested cells were filtered through a 45 µM nylon mesh, washed with RPMI/20% FBS, and washed twice with HBSS. Dissociated tumor cells were then injected subcutaneously into the mammary fat pads of NOD/SCID mice to elicit tumor growth.

In certain embodiments, dissociated tumor cells are first sorted into tumorigenic and non-tumorigenic cells based on cell surface markers before injection into experimental animals. Specifically, tumor cells dissociated as described above are washed twice with Hepes buffered saline solution (HBSS) containing 2% heat-inactivated calf serum (HICS) and resuspended at $10^6$ cells per 100 µl. Antibodies are added and the cells incubated for 20 minutes on ice followed by two washes with HBSS/2% HICS. Antibodies include anti-ESA (Biomeda, Foster City, Calif.), anti-CD44, anti-CD24, and Lineage markers anti-CD2, -CD3, -CD10, -CD16, -CD18, -CD31, -CD64, and -CD140b (collectively referred to as Lin; PharMingen, San Jose, Calif.). Antibodies are directly conjugated to fluorochromes to positively or negatively select cells expressing these markers. Mouse cells are eliminated by selecting against H2 Kd+ cells, and dead cells are eliminated by using the viability dye 7AAD. Flow cytometry is performed on a FACSVantage (Becton Dickinson, Franklin Lakes, N.J.). Side scatter and forward scatter profiles are used to eliminate cell clumps. Isolated ESA+, CD44+, CD24−/low, Lin− tumorigenic cells are then injected subcutaneously into NOD/SCID mice to elicit tumor growth.

Figure 9A:
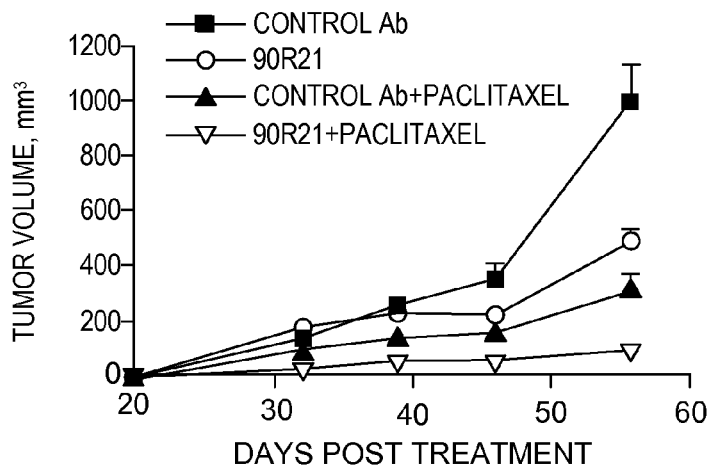
Figure 9B:
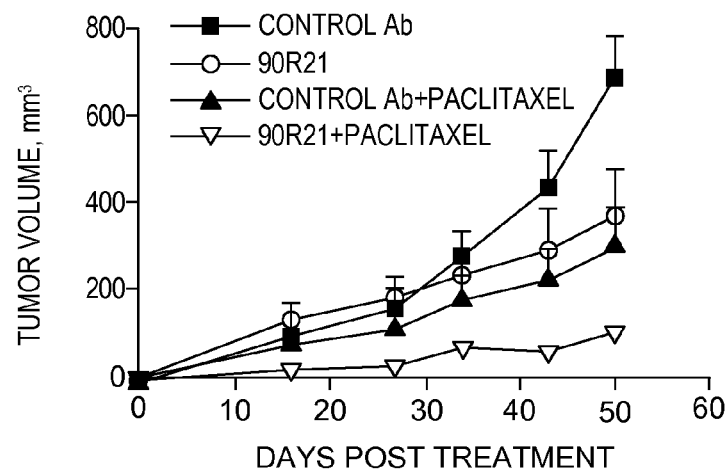

In certain embodiments, anti-Notch ligand binding region antibodies were analyzed for their ability to reduce the growth of breast tumors in vivo. Dissociated PE13 (FIG. 9A) or T3 (FIG. 9B) breast tumor cells (50,000 cells per animal; 10 animals per treatment group) were injected subcutaneously into the right mammary fat pads of NOD/SCID mice. T3 cells were injected in combination with the implantation of an estrogen pellet. Treatment began two days following cell injection. Animals were divided into four treatment groups: control antibody; anti-Notch ligand binding region antibody 90821; control antibody in combination with Paclitaxel; and 90R21 in combination with Paclitaxel. Antibodies were administered twice a week at 10 mg/kg and Paclitaxel was administered once a week at 10 mg/kg. While treatment with 90R21 significantly reduced tumor growth compared to control antibody treated animals after 55 days, combination treatment with 90821 and Paclitaxel virtually eliminated T3 tumor growth (FIG. 9).

In certain embodiments, anti-Notch ligand binding region antibodies are analyzed for their ability to reduce the growth of UM-C9 colon tumors. Dissociated UM-C9 cells (10,000 per animal) are injected subcutaneously into the right flank region of 6-8 week old NOD/SCID mice. The day after tumor cell injection, animals are injected intraperitoneal (i.p.) with 10 mg/kg anti-Notch ligand binding region antibodies (n=10) or PBS (n=10) two times per week for the duration of the experiment. Tumor growth is monitored weekly until growth is detected, after which point tumor growth is measured twice weekly. The ability of Notch ligand binding region antibodies to reduce tumor growth is thus determined.

In certain embodiments, the expression of Notch target genes followed during the course of treatment with anti-Notch ligand binding region antibodies. Dissociated OM-C9 cells (10,000 per animal) are injected subcutaneously into the right flank region of 6-8 week old NOD/SCID mice. The day after tumor cell injection, animals are injected intraperitoneal (i.p.) with 10 mg/kg anti-Notch ligand binding region antibodies (n=10) or PBS (n=10) two times per week for the duration of the experiment. Tumor growth is monitored weekly until growth is detected, after which tumor growth is measured weekly. At the end of the experiment, tumor cells are removed from treated and control animals and expression of Notch target genes is determined using quantitative RT-PCR. Specifically, total RNA is extracted from frozen colon tumor samples using standard protocols. Gene expression analysis is performed in triplicate with 100 ng of purified total RNA using standard reverse transcriptase and quantitative PCR conditions with primers and probes designed for each gene. Data are analyzed using the Comparative Ct Method with GUSB as an internal control (See Applied Biosystems User Bulletins on Relative Quantitation of Gene Expression). The effect of anti-Notch ligand binding region antibodies on expression of three Notch target genes: ATOH1, HES1, and HEY1 is thus determined.

Example 5

In Vivo Treatment of Tumors Using Anti-Notch Ligand Binding Region Antibodies

This example describes the use of anti-Notch ligand binding region antibodies to treat cancer in a xenograft model. In certain embodiments, tumor cells from a patient sample (solid tumor biopsy or pleural effusion) that have been passaged as a xenograft in mice are prepared for repassaging into experimental animals. Tumor tissue is removed, cut up into small pieces, minced completely using sterile blades, and single cell suspensions obtained by enzymatic digestion and mechanical disruption. Dissociated tumor cells are then injected subcutaneously either into the mammary fat pads, for breast tumors, or into the flank, for non-breast tumors, of NOD/SCID mice to elicit tumor growth. Alternatively, ESA+, CD44+, CD24−/low, Lin− tumorigenic tumor cells are isolated as described in detail above and injected.

Following tumor cell injection, animals are monitored for tumor growth. Once tumors reach an average size of approximately 150 to 200 mm, antibody treatment begins. Each animal receives 100 µg Notch ligand binding region antibodies or control antibodies i.p. two to five times per week for a total of 6 weeks. Tumor size is assessed twice a week during these 6 weeks. The ability of Notch ligand binding region antibodies to prevent further tumor growth or to reduce tumor size compared to control antibodies is thus determined.

At the end point of antibody treatment, tumors are harvested for further analysis. In some embodiments, a portion of the tumor is analyzed by immunofluorescence to assess antibody penetration into the tumor and tumor response. A portion of each harvested tumor from anti-Notch ligand binding region treated and control antibody treated mice is fresh-frozen in liquid nitrogen, embedded in O.C.T., and cut on a cryostat as 10 µm sections onto glass slides. In some embodiments, a portion of each tumor is formalin-fixed, paraffin-embedded, and cut on a microtome as 10 µm section onto glass slides. Sections are post-fixed and incubated with chromophore labeled antibodies that specifically recognize injected antibodies to detect anti-Notch ligand binding region antibodies or control antibodies present in the tumor biopsy. Furthermore antibodies that detect different tumor and tumor-recruited cell types such as, for example, anti-VE cadherin (CD144) or anti-PECAM-1 (CD31) antibodies to detect vascular endothelial cells, anti-smooth muscle alpha-actin antibodies to detect vascular smooth muscle cells, anti-Ki67 antibodies to detect proliferating cells, TUNEL assays to detect dying cells, anti-intracellular domain (ICD) Notch fragment antibodies to detect Notch signaling can be used to assess the effects of antibody treatment on, for example, angiogenesis, tumor growth and tumor morphology.

In certain embodiments, the effect of anti-Notch ligand binding region antibody treatment on tumor cell gene expression is also assessed. Total RNA is extracted from a portion of each harvested tumor from experimental antibody treated and control antibody treated mice and used for quantitative RT-PCR. Expression levels of Notch receptors, Notch receptor ligands, components of the Notch signaling pathway, as well as addition cancer stem cell markers previously identified (e.g. CD44) are analyzed relative to the house-keeping gene GAPDH as an internal control. Changes in tumor cell gene expression upon Notch ligand binding region antibody treatment are thus determined.

In addition, the effect of anti-Notch ligand binding region antibody treatment on the presence of cancer stem cells in a tumor is assessed. Tumor samples from experimental versus control antibody treated mice are cut up into small pieces, minced completely using sterile blades, and single cell suspensions obtained by enzymatic digestion and mechanical disruption. Dissociated tumor cells are then analyzed by FACS analysis for the presence of tumorigenic cancer stem cells based on ESA+, CD44+, CD24−/low, Lin− surface cell marker expression as described in detail above.

The tumorigenicity of cells isolated based on ESA+, CD44+, CD24−/low, Lin− expression following anti-Notch EGF11 antibody treatment can then assessed. ESA+, CD44+, CD24−/low, Lin− cancer stem cells isolated from experimental antibody treated versus control antibody treated mice are re-injected subcutaneously into the mammary fat pads of NOD/SCID mice. The tumorigenicity of cancer stem cells based on the number of injected cells required for consistent tumor formation is then determined.

Example 6

Treatment of Human Cancer Using Anti-Notch Ligand Binding Region Antibodies

This example describes methods for treating cancer using antibodies against a Notch receptor ligand binding region to target tumors comprising cancer stem cells and/or tumor cells in which Notch receptor or Notch receptor ligand expression has been detected. The presence of cancer stem cell marker expression can first be determined from a tumor biopsy. Tumor cells from a biopsy from a patient diagnosed with cancer are removed under sterile conditions. In some embodiments the tissue biopsy is fresh-frozen in liquid nitrogen, embedded in O.C.T., and cut on a cryostat as 10 µm sections onto glass slides. In some embodiments, the tissue biopsy is formalin-fixed, paraffin-embedded, and cut on a microtome as 10 µm section onto glass slides. Sections are incubated with anti-Notch ligand binding region antibodies to detect protein expression.

The presence of cancer stem cells can also be determined. Tissue biopsy samples are cut up into small pieces, minced completely using sterile blades, and cells subject to enzymatic digestion and mechanical disruption to obtain a single cell suspension. Dissociated tumor cells are then incubated with anti-ESA, -CD44, -CD24, -Lin, and -Notch ligand antibodies to detect cancer stem cells, and the presence of ESA+, CD44+, CD24−/low, Lin−, Notch ligand+ tumor stem cells is determined by flow cytometry as described in detail above.

Cancer patients whose tumors are diagnosed as expressing a Notch receptor or Notch receptor ligand are treated with anti-Notch ligand binding region antibodies. In certain embodiments, humanized or human monoclonal anti-Notch ligand binding region antibodies generated as described above are purified and formulated with a suitable pharmaceutical vehicle for injection. In some embodiments, patients are treated with the Notch ligand binding region antibodies at least once a month for at least 10 weeks. In some embodiments, patients are treated with the Notch ligand binding region antibodies at least once a week for at least about 14 weeks. Each administration of the antibody should be a pharmaceutically effective dose. In some embodiments, between about 2 to about 100 mg/ml of an anti-Notch ligand binding region antibody is administered. In some embodiments, between about 5 to about 40 mg/ml of an anti-Notch ligand binding region antibody is administered. The antibody can be administered prior to, concurrently with, or after standard radiotherapy regimens or chemotherapy regimens using one or more chemotherapeutic agent, such as oxaliplatin, fluorouracil, leucovorin, or streptozocin. Patients are monitored to determine whether such treatment has resulted in an anti-tumor response, for example, based on tumor regression, reduction in the incidences of new tumors, lower tumor antigen expression, decreased numbers of cancer stem cells, or other means of evaluating disease prognosis.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims. All publications, patents and patent applications cited herein are incorporated by reference in their entirety into the disclosure.

What is claimed is:

1. An isolated anti-human Notch3 receptor monoclonal antibody that specifically binds to the glutamate ligand binding region of SEQ ID NO:23 on human Notch3.

2. The antibody of claim 1, which is an antagonist of Notch signaling.

3. The antibody of claim 2, which blocks ligand binding.

4. The antibody of claim 1, which specifically binds to an epitope comprising the glutamate residue at position 403 of human Notch3 receptor.

5. The antibody of claim 1, which also binds human Notch1.

6. The antibody of claim 1, which comprises a heavy chain variable region comprising CDR amino acid sequences CDR1 (SEQ ID NO:10); CDR2 (SEQ ID NO:11); and CDR3 (SEQ ID NO:12).

7. The antibody of claim 6, which further comprises a light chain variable region comprising CDR amino acid sequences CDR1 (SEQ ID NO:14); CDR2 (SEQ ID NO:15); and CDR3 (SEQ ID NO:16).

8. The antibody of claim 7, which also binds human Notch1.

9. The antibody of claim 7, which is 122R5 (ATCC deposit No. PTA-8908).

10. The antibody of claim 1, which comprises a heavy chain variable region comprising amino acids 20-143 of SEQ ID NO:9 and a light chain variable region comprising amino acids 20-127 of SEQ ID NO:13.

11. The antibody of claim 1, which is an antibody fragment.

12. The antibody of claim 1, which is a human antibody or a humanized antibody.

13. An isolated host cell that produces the antibody of claim 1.

14. A hybridoma that produces the antibody of claim 1.

15. A composition comprising the antibody of claim 1 and a pharmaceutically acceptable vehicle.

* * * * *

SEQUENCE LISTING

<160> NUMBER OF SEQ ID NOS: 70

<210> SEQ ID NO 1
<211> LENGTH: 460
<212> TYPE: PRT
<213> ORGANISM: Artificial Sequence
<220> FEATURE:
<223> OTHER INFORMATION: Synthetic 90R21 Heavy chain

<400> SEQUENCE: 1

Met Lys His Leu Trp Phe Phe Leu Leu Leu Val Ala Ala Pro Arg Trp
1               5                   10                  15

Val Leu Ser Glu Val Gln Leu Leu Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Ser Asn Tyr Gly Met Ser Trp Val Arg Gln Ala Pro Gly Lys Gly Leu
    50                  55                  60

Glu Trp Val Ser Ser Ile Ser Gly Tyr Gly Ser Asn Thr Tyr Tyr Ala
65                  70                  75                  80

Asp Ser Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Tyr Cys Ala Arg Ile Ser Gln Gln Ala Val Trp Gly Gln Gly Thr
        115                 120                 125

Leu Val Thr Val Ser Ser Ala Ser Thr Lys Gly Pro Ser Val Phe Pro
    130                 135                 140

Leu Ala Pro Cys Ser Arg Ser Thr Ser Glu Ser Thr Ala Ala Leu Gly
145                 150                 155                 160

Cys Leu Val Lys Asp Tyr Phe Pro Glu Pro Val Thr Val Ser Trp Asn
                165                 170                 175

Ser Gly Ala Leu Thr Ser Gly Val His Thr Phe Pro Ala Val Leu Gln
            180                 185                 190

Ser Ser Gly Leu Tyr Ser Leu Ser Ser Val Val Thr Val Pro Ser Ser
        195                 200                 205

Asn Phe Gly Thr Gln Thr Tyr Thr Cys Asn Val Asp His Lys Pro Ser
    210                 215                 220

Asn Thr Lys Val Asp Lys Thr Val Glu Arg Lys Cys Cys Val Glu Cys
225                 230                 235                 240

Pro Pro Cys Pro Ala Pro Pro Val Ala Gly Pro Ser Val Phe Leu Phe
                245                 250                 255

Pro Pro Lys Pro Lys Asp Thr Leu Met Ile Ser Arg Thr Pro Glu Val
            260                 265                 270

Thr Cys Val Val Val Asp Val Ser His Glu Asp Pro Glu Val Gln Phe
        275                 280                 285

Asn Trp Tyr Val Asp Gly Val Glu Val His Asn Ala Lys Thr Lys Pro
    290                 295                 300

Arg Glu Glu Gln Phe Asn Ser Thr Phe Arg Val Val Ser Val Leu Thr
305                 310                 315                 320

Val Val His Gln Asp Trp Leu Asn Gly Lys Glu Tyr Lys Cys Lys Val
                325                 330                 335

Ser Asn Lys Gly Leu Pro Ala Pro Ile Glu Lys Thr Ile Ser Lys Thr
            340                 345                 350

```
Lys Gly Gln Pro Arg Glu Pro Gln Val Tyr Thr Leu Pro Pro Ser Arg
        355                 360                 365

Glu Glu Met Thr Lys Asn Gln Val Ser Leu Thr Cys Leu Val Lys Gly
    370                 375                 380

Phe Tyr Pro Ser Asp Ile Ala Val Glu Trp Glu Ser Asn Gly Gln Pro
385                 390                 395                 400

Glu Asn Asn Tyr Lys Thr Thr Pro Pro Met Leu Asp Ser Asp Gly Ser
                405                 410                 415

Phe Phe Leu Tyr Ser Lys Leu Thr Val Asp Lys Ser Arg Trp Gln Gln
            420                 425                 430

Gly Asn Val Phe Ser Cys Ser Val Met His Glu Ala Leu His Asn His
        435                 440                 445

Tyr Thr Gln Lys Ser Leu Ser Leu Ser Pro Gly Lys
    450                 455                 460

<210> SEQ ID NO 2
<211> LENGTH: 10
<212> TYPE: PRT
<213> ORGANISM: Artificial Sequence
<220> FEATURE:
<223> OTHER INFORMATION: Synthetic 90R21 Heavy chain CDR1

<400> SEQUENCE: 2

Gly Phe Thr Phe Ser Asn Tyr Gly Met Ser
1               5                   10

<210> SEQ ID NO 3
<211> LENGTH: 17
<212> TYPE: PRT
<213> ORGANISM: Artificial Sequence
<220> FEATURE:
<223> OTHER INFORMATION: Synthetic 90R21 Heavy chain CDR2

<400> SEQUENCE: 3

Ser Ile Ser Gly Tyr Gly Ser Asn Thr Tyr Tyr Ala Asp Ser Val Lys
1               5                   10                  15

Gly

<210> SEQ ID NO 4
<211> LENGTH: 6
<212> TYPE: PRT
<213> ORGANISM: Artificial Sequence
<220> FEATURE:
<223> OTHER INFORMATION: Synthetic 90R21 Heavy chain CDR3

<400> SEQUENCE: 4

Ile Ser Gln Gln Ala Val
1               5

<210> SEQ ID NO 5
<211> LENGTH: 234
<212> TYPE: PRT
<213> ORGANISM: Artificial Sequence
<220> FEATURE:
<223> OTHER INFORMATION: Synthetic 90R21 Light chain

<400> SEQUENCE: 5

Met Ala Trp Ala Leu Leu Leu Thr Leu Leu Thr Gln Gly Thr Gly
1               5                   10                  15

Ser Trp Ala Gln Ser Ala Leu Thr Gln Pro Ala Ser Val Ser Gly Ser
            20                  25                  30
```

```
Pro Gly Gln Ser Ile Thr Ile Ser Cys Thr Gly Thr Ser Ser Asp Ile
            35                  40                  45

Gly Gly Tyr Gln Tyr Val Ser Trp Tyr Gln Gln His Pro Gly Lys Ala
    50                  55                  60

Pro Lys Leu Met Ile Tyr Tyr Val Ser Asn Arg Pro Ser Gly Val Ser
65                  70                  75                  80

Asn Arg Phe Ser Gly Ser Lys Ser Gly Asn Thr Ala Ser Leu Thr Ile
                85                  90                  95

Ser Gly Leu Gln Ala Glu Asp Glu Ala Asp Tyr Tyr Cys Gln Ser Ala
            100                 105                 110

Asp Ser Ser Ser Trp Val Phe Gly Gly Gly Thr Lys Leu Thr Val Leu
            115                 120                 125

Gly Gln Pro Lys Ala Ala Pro Ser Val Thr Leu Phe Pro Pro Ser Ser
    130                 135                 140

Glu Glu Leu Gln Ala Asn Lys Ala Thr Leu Val Cys Leu Ile Ser Asp
145                 150                 155                 160

Phe Tyr Pro Gly Ala Val Thr Val Ala Trp Lys Ala Asp Ser Ser Pro
                165                 170                 175

Val Lys Ala Gly Val Glu Thr Thr Thr Pro Ser Lys Gln Ser Asn Asn
            180                 185                 190

Lys Tyr Ala Ala Ser Ser Tyr Leu Ser Leu Thr Pro Glu Gln Trp Lys
            195                 200                 205

Ser His Arg Ser Tyr Ser Cys Gln Val Thr His Glu Gly Ser Thr Val
    210                 215                 220

Glu Lys Thr Val Ala Pro Thr Glu Cys Ser
225                 230

<210> SEQ ID NO 6
<211> LENGTH: 14
<212> TYPE: PRT
<213> ORGANISM: Artificial Sequence
<220> FEATURE:
<223> OTHER INFORMATION: Synthetic 90R21 Light chain CDR1

<400> SEQUENCE: 6

Thr Gly Thr Ser Ser Asp Ile Gly Gly Tyr Gln Tyr Val Ser
1               5                   10

<210> SEQ ID NO 7
<211> LENGTH: 8
<212> TYPE: PRT
<213> ORGANISM: Artificial Sequence
<220> FEATURE:
<223> OTHER INFORMATION: Synthetic 90R21 Light chain CDR2

<400> SEQUENCE: 7

Tyr Val Ser Asn Arg Pro Ser Gly
1               5

<210> SEQ ID NO 8
<211> LENGTH: 8
<212> TYPE: PRT
<213> ORGANISM: Artificial Sequence
<220> FEATURE:
<223> OTHER INFORMATION: Synthetic 90R21 Light chain CDR3

<400> SEQUENCE: 8

Gln Ser Ala Asp Ser Ser Ser Trp
1               5
```

```
<210> SEQ ID NO 9
<211> LENGTH: 466
<212> TYPE: PRT
<213> ORGANISM: Artificial Sequence
<220> FEATURE:
<223> OTHER INFORMATION: Synthetic 122R5 Heavy chain

<400> SEQUENCE: 9

Met Lys His Leu Trp Phe Phe Leu Leu Leu Val Ala Ala Pro Arg Trp
1               5                   10                  15

Val Leu Ser Gln Val Gln Leu Val Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Ser Asp Asn Ala Ile His Trp Val Arg Gln Ala Pro Gly Lys Gly Leu
    50                  55                  60

Glu Trp Val Ser Ala Ile Ser Ser Tyr Gly Gly Thr Tyr Tyr Ala
65                  70                  75                  80

Asp Ser Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Tyr Cys Ala Arg Pro Gly Phe Gln Phe Ser Phe Thr Phe Met Asp
        115                 120                 125

Ile Trp Gly Gln Gly Thr Leu Val Thr Val Ser Ser Ala Ser Thr Lys
    130                 135                 140

Gly Pro Ser Val Phe Pro Leu Ala Pro Cys Ser Arg Ser Thr Ser Glu
145                 150                 155                 160

Ser Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Asn Phe Gly Thr Gln Thr Tyr Thr Cys Asn
    210                 215                 220

Val Asp His Lys Pro Ser Asn Thr Lys Val Asp Lys Thr Val Glu Arg
225                 230                 235                 240

Lys Cys Cys Val Glu Cys Pro Pro Cys Pro Ala Pro Val Ala Gly
                245                 250                 255

Pro Ser Val Phe Leu Phe Pro Pro Lys Pro Lys Asp Thr Leu Met Ile
            260                 265                 270

Ser Arg Thr Pro Glu Val Thr Cys Val Val Val Asp Val Ser His Glu
        275                 280                 285

Asp Pro Glu Val Gln Phe Asn Trp Tyr Val Asp Gly Val Glu Val His
    290                 295                 300

Asn Ala Lys Thr Lys Pro Arg Glu Glu Gln Phe Asn Ser Thr Phe Arg
305                 310                 315                 320

Val Val Ser Val Leu Thr Val Val His Gln Asp Trp Leu Asn Gly Lys
                325                 330                 335

Glu Tyr Lys Cys Lys Val Ser Asn Lys Gly Leu Pro Ala Pro Ile Glu
            340                 345                 350

Lys Thr Ile Ser Lys Thr Lys Gly Gln Pro Arg Glu Pro Gln Val Tyr
        355                 360                 365
```

```
Thr Leu Pro Pro Ser Arg Glu Glu Met Thr Lys Asn Gln Val Ser Leu
        370                 375                 380

Thr Cys Leu Val Lys Gly Phe Tyr Pro Ser Asp Ile Ala Val Glu Trp
385                 390                 395                 400

Glu Ser Asn Gly Gln Pro Glu Asn Asn Tyr Lys Thr Thr Pro Pro Met
                405                 410                 415

Leu Asp Ser Asp Gly Ser Phe Phe Leu Tyr Ser Lys Leu Thr Val Asp
            420                 425                 430

Lys Ser Arg Trp Gln Gln Gly Asn Val Phe Ser Cys Ser Val Met His
        435                 440                 445

Glu Ala Leu His Asn His Tyr Thr Gln Lys Ser Leu Ser Leu Ser Pro
    450                 455                 460

Gly Lys
465

<210> SEQ ID NO 10
<211> LENGTH: 10
<212> TYPE: PRT
<213> ORGANISM: Artificial Sequence
<220> FEATURE:
<223> OTHER INFORMATION: Synthetic 122R5 Heavy chain CDR1

<400> SEQUENCE: 10

Gly Phe Thr Phe Ser Asp Asn Ala Ile His
1               5                   10

<210> SEQ ID NO 11
<211> LENGTH: 17
<212> TYPE: PRT
<213> ORGANISM: Artificial Sequence
<220> FEATURE:
<223> OTHER INFORMATION: Synthetic 122R5 Heavy chain CDR2

<400> SEQUENCE: 11

Ala Ile Ser Ser Tyr Gly Ser Gly Thr Tyr Tyr Ala Asp Ser Val Lys
1               5                   10                  15

Gly

<210> SEQ ID NO 12
<211> LENGTH: 12
<212> TYPE: PRT
<213> ORGANISM: Artificial Sequence
<220> FEATURE:
<223> OTHER INFORMATION: Synthetic 122R5 Heavy chain CDR3

<400> SEQUENCE: 12

Pro Gly Phe Gln Phe Ser Phe Thr Phe Met Asp Ile
1               5                   10

<210> SEQ ID NO 13
<211> LENGTH: 232
<212> TYPE: PRT
<213> ORGANISM: Artificial Sequence
<220> FEATURE:
<223> OTHER INFORMATION: Synthetic 122R5 Light chain

<400> SEQUENCE: 13

Met Ala Trp Ala Leu Leu Leu Thr Leu Leu Thr Gln Gly Thr Gly
1               5                   10                  15

Ser Trp Ala Asp Ile Glu Leu Thr Gln Pro Pro Ser Val Ser Val Ala
            20                  25                  30
```

```
Pro Gly Gln Thr Ala Arg Ile Ser Cys Ser Gly Asp Ala Leu Gly Ser
        35                  40                  45

Lys Tyr Ala Ser Trp Tyr Gln Gln Lys Pro Gly Gln Ala Pro Val Leu
 50                  55                  60

Val Ile Tyr Asp Asp Lys Asn Arg Pro Ser Gly Ile Pro Glu Arg Phe
 65                  70                  75                  80

Ser Gly Ser Asn Ser Gly Asn Thr Ala Thr Leu Thr Ile Ser Gly Thr
                 85                  90                  95

Gln Ala Glu Asp Glu Ala Asp Tyr Tyr Cys Gln Ser Trp Asp Gly Lys
            100                 105                 110

Ser Lys Val Val Phe Gly Gly Thr Lys Leu Thr Val Leu Gly Gln
            115                 120                 125

Pro Lys Ala Ala Pro Ser Val Thr Leu Phe Pro Pro Ser Ser Glu Glu
        130                 135                 140

Leu Gln Ala Asn Lys Ala Thr Leu Val Cys Leu Ile Ser Asp Phe Tyr
145                 150                 155                 160

Pro Gly Ala Val Thr Val Ala Trp Lys Ala Asp Ser Ser Pro Val Lys
                165                 170                 175

Ala Gly Val Glu Thr Thr Thr Pro Ser Lys Gln Ser Asn Asn Lys Tyr
            180                 185                 190

Ala Ala Ser Ser Tyr Leu Ser Leu Thr Pro Glu Gln Trp Lys Ser His
        195                 200                 205

Arg Ser Tyr Ser Cys Gln Val Thr His Glu Gly Ser Thr Val Glu Lys
    210                 215                 220

Thr Val Ala Pro Thr Glu Cys Ser
225                 230

<210> SEQ ID NO 14
<211> LENGTH: 11
<212> TYPE: PRT
<213> ORGANISM: Artificial Sequence
<220> FEATURE:
<223> OTHER INFORMATION: Synthetic 122R5 Light chain CDR1

<400> SEQUENCE: 14

Ser Gly Asp Ala Leu Gly Ser Lys Tyr Ala Ser
1               5                   10

<210> SEQ ID NO 15
<211> LENGTH: 8
<212> TYPE: PRT
<213> ORGANISM: Artificial Sequence
<220> FEATURE:
<223> OTHER INFORMATION: Synthetic 122R5 Light chain CDR2

<400> SEQUENCE: 15

Asp Asp Lys Asn Arg Pro Ser Gly
1               5

<210> SEQ ID NO 16
<211> LENGTH: 9
<212> TYPE: PRT
<213> ORGANISM: Artificial Sequence
<220> FEATURE:
<223> OTHER INFORMATION: Synthetic 122R5 Light chain CDR3

<400> SEQUENCE: 16

Gln Ser Trp Asp Gly Lys Ser Lys Val
1               5
```

<210> SEQ ID NO 17
<211> LENGTH: 402
<212> TYPE: DNA
<213> ORGANISM: Artificial Sequence
<220> FEATURE:
<223> OTHER INFORMATION: Synthetic 90R21 Heavy chain DNA

<400> SEQUENCE: 17

```
atgaagcatc tctggttttt cctgctgctc gttgccgctc cacgtgggt gctgtctgaa      60
gtccagctgc tcgagagcgg aggagggctc gtgcagcccg agggagcct cagactgtct     120
tgcgccgctt ctggattcac tttttcaaac tatgggatga gctgggttag acaggctcct     180
ggcaagggcc tcgagtgggt tagtagtatc agcggatatg gtagcaacac ttattacgca     240
gattctgtga aggggcggtt taccatcagt agggataaca gcagaacac cctctatctg     300
caaatgaatt cactgagagc cgaggatacc gccgtttact attgcgcccg gatctcccag     360
caggccgtct gggggcaggg caccctcgtg acagtcagct ca                        402
```

<210> SEQ ID NO 18
<211> LENGTH: 375
<212> TYPE: DNA
<213> ORGANISM: Artificial Sequence
<220> FEATURE:
<223> OTHER INFORMATION: Synthetic 90R21 Light chain DNA

<400> SEQUENCE: 18

```
atggcctggg ctctgctgct cctcaccctc ctcactcagg gcacaggatc ctgggctcag      60
tctgccctca cccagcctgc ttccgtgtca ggttccctg gccagtcaat aaccatttcc     120
tgcaccggga catcatccga tattggagga taccagtacg tgagttggta ccagcaacac     180
cccggtaaag cccaaaaact catgatctac tacgtgtcca atagccttc aggagtttct     240
aatcgcttta gcgggagcaa gagtggcaac accgcatcac tcactattag tggactccag     300
gcagaggacg aagcagatta ttactgtcag agcgccgaca gttcttcctg gtgttcggc     360
ggtgggacta agtta                                                      375
```

<210> SEQ ID NO 19
<211> LENGTH: 420
<212> TYPE: DNA
<213> ORGANISM: Artificial Sequence
<220> FEATURE:
<223> OTHER INFORMATION: Synthetic 122R5 Heavy chain DNA

<400> SEQUENCE: 19

```
atgaaacacc tgtggttctt cctcctgctg gtggcagctc ccagatgggt cctgtccgaa      60
gtgcaattgg tggaaagcgg cggcggcctg gtgcaaccgg cggcagcct gcgtctgagc     120
tgcgcggcct ccggatttac cttctctgat aatgctattc attgggtgcg ccaagcccct     180
ggaagggtc tcgagtgggt gagcgctatc tcttcttatg gtagcggtac ctattatgcg     240
gatagcgtga aggccgtttt taccatttca cgtgataatt cgaaaaacac cctgtatctg     300
caaatgaaca gcctgcgtgc ggaagatacg gccgtgtatt attgcgcgcg tcctggtttt     360
cagttttctt ttacttttat ggatatttgg ggccaaggca ccctggtgac ggttagctca     420
```

<210> SEQ ID NO 20
<211> LENGTH: 369
<212> TYPE: DNA
<213> ORGANISM: Artificial Sequence
<220> FEATURE:
<223> OTHER INFORMATION: Synthetic 122R5 Light chain DNA

```
<400> SEQUENCE: 20
atggcctggg ctctgctgct cctcaccctc ctcactcagg gcacaggatc ctgggctgat      60
atcgaactga cccagccgcc ttcagtgagc gttgcaccag gtcagaccgc gcgtatctcg     120
tgtagcggcg atgctcttgg ttctaagtat gcttcttggt accagcagaa acccgggcag     180
gcgccagttc ttgtgattta tgatgataag aatcgtccct caggcatccc ggaacgcttt     240
agcggatcca cagcggcaa caccgcgacc ctgaccatta gcggcactca ggcggaagac     300
gaagcggatt attattgcca gtcttgggat ggtaagtcta aggttgtgtt tggcggcggc     360
acgaagtta                                                              369

<210> SEQ ID NO 21
<211> LENGTH: 11
<212> TYPE: PRT
<213> ORGANISM: Homo sapiens

<400> SEQUENCE: 21

Pro Cys Glu His Ala Gly Lys Cys Ile Asn Thr
1               5                   10

<210> SEQ ID NO 22
<211> LENGTH: 11
<212> TYPE: PRT
<213> ORGANISM: Homo sapiens

<400> SEQUENCE: 22

Pro Cys Glu His Ala Gly Lys Cys Val Asn Thr
1               5                   10

<210> SEQ ID NO 23
<211> LENGTH: 11
<212> TYPE: PRT
<213> ORGANISM: Homo sapiens

<400> SEQUENCE: 23

Pro Cys Glu His Leu Gly Arg Cys Val Asn Thr
1               5                   10

<210> SEQ ID NO 24
<211> LENGTH: 11
<212> TYPE: PRT
<213> ORGANISM: Homo sapiens

<400> SEQUENCE: 24

Pro Cys Glu His Gly Gly Ser Cys Leu Asn Thr
1               5                   10

<210> SEQ ID NO 25
<211> LENGTH: 11
<212> TYPE: PRT
<213> ORGANISM: Homo sapiens
<220> FEATURE:
<221> NAME/KEY: MISC_FEATURE
<222> LOCATION: (5)..(5)
<223> OTHER INFORMATION: Xaa = non-polar, aliphatic amino acid residue
<220> FEATURE:
<221> NAME/KEY: MISC_FEATURE
<222> LOCATION: (7)..(7)
<223> OTHER INFORMATION: Xaa = positively charged amino acid residue
<220> FEATURE:
<221> NAME/KEY: MISC_FEATURE
<222> LOCATION: (9)..(9)
<223> OTHER INFORMATION: Xaa = non-polar, aliphatic amino acid residue
<220> FEATURE:
```

```
<221> NAME/KEY: MISC_FEATURE
<222> LOCATION: (11)..(11)
<223> OTHER INFORMATION: Xaa = non-polar, aliphatic amino acid residue

<400> SEQUENCE: 25

Pro Cys Glu His Xaa Gly Xaa Cys Xaa Asn Xaa
1               5                   10

<210> SEQ ID NO 26
<211> LENGTH: 11
<212> TYPE: PRT
<213> ORGANISM: Homo sapiens

<400> SEQUENCE: 26

Pro Cys Glu His Ala Gly Arg Cys Ala Asn Thr
1               5                   10

<210> SEQ ID NO 27
<211> LENGTH: 12
<212> TYPE: PRT
<213> ORGANISM: Artificial Sequence
<220> FEATURE:
<223> OTHER INFORMATION: Notch receptor antibody-generating polypeptide
<220> FEATURE:
<221> NAME/KEY: MISC_FEATURE
<222> LOCATION: (6)..(6)
<223> OTHER INFORMATION: Xaa = non-polar, aliphatic amino acid residue
<220> FEATURE:
<221> NAME/KEY: MISC_FEATURE
<222> LOCATION: (8)..(8)
<223> OTHER INFORMATION: Xaa = positively charged amino acid
<220> FEATURE:
<221> NAME/KEY: MISC_FEATURE
<222> LOCATION: (10)..(10)
<223> OTHER INFORMATION: Xaa = non-polar, aliphatic amino acid residue
<220> FEATURE:
<221> NAME/KEY: MISC_FEATURE
<222> LOCATION: (12)..(12)
<223> OTHER INFORMATION: Xaa = non-polar, aliphatic amino acid residue

<400> SEQUENCE: 27

Asn Pro Cys Glu His Xaa Gly Xaa Cys Xaa Asn Xaa
1               5                   10

<210> SEQ ID NO 28
<211> LENGTH: 12
<212> TYPE: PRT
<213> ORGANISM: Artificial Sequence
<220> FEATURE:
<223> OTHER INFORMATION: Notch receptor antibody-generating polypeptide

<400> SEQUENCE: 28

Gln Pro Cys Glu His Ala Gly Arg Cys Ala Asn Thr
1               5                   10

<210> SEQ ID NO 29
<211> LENGTH: 36
<212> TYPE: PRT
<213> ORGANISM: Homo sapiens

<400> SEQUENCE: 29

Arg Cys Ser Gln Pro Gly Glu Thr Cys Leu Asn Gly Gly Lys Cys Glu
1               5                   10                  15

Ala Ala Asn Gly Thr Glu Ala Cys Val Cys Gly Gly Ala Pro Val Gly
                20                  25                  30

Pro Arg Cys Gln
            35
```

<210> SEQ ID NO 30
<211> LENGTH: 42
<212> TYPE: PRT
<213> ORGANISM: Homo sapiens

<400> SEQUENCE: 30

Asp Pro Asn Pro Cys Leu Ser Thr Pro Cys Lys Asn Ala Gly Thr Cys
1               5                   10                  15

His Val Val Asp Arg Arg Gly Val Ala Asp Tyr Ala Cys Ser Cys Ala
            20                  25                  30

Leu Gly Pro Ser Gly Pro Leu Cys Leu Thr
        35                  40

<210> SEQ ID NO 31
<211> LENGTH: 40
<212> TYPE: PRT
<213> ORGANISM: Homo sapiens

<400> SEQUENCE: 31

Pro Leu Asp Asn Ala Cys Leu Thr Asn Pro Cys Arg Asn Gly Gly Thr
1               5                   10                  15

Cys Asp Leu Leu Thr Leu Thr Glu Tyr Lys Cys Arg Cys Pro Pro Gly
            20                  25                  30

Trp Ser Gly Lys Ser Cys Gln Gln
        35                  40

<210> SEQ ID NO 32
<211> LENGTH: 37
<212> TYPE: PRT
<213> ORGANISM: Homo sapiens

<400> SEQUENCE: 32

Ala Asp Pro Cys Ala Ser Asn Pro Cys Ala Asn Gly Gly Gln Cys Leu
1               5                   10                  15

Pro Phe Glu Ala Ser Tyr Ile Cys His Cys Pro Pro Ser Pro His Gly
            20                  25                  30

Pro Thr Cys Arg Gln
        35

<210> SEQ ID NO 33
<211> LENGTH: 39
<212> TYPE: PRT
<213> ORGANISM: Homo sapiens
<220> FEATURE:
<221> NAME/KEY: misc_feature
<222> LOCATION: (8)..(8)
<223> OTHER INFORMATION: Xaa can be any naturally occurring amino acid

<400> SEQUENCE: 33

Asp Val Asn Glu Cys Gly Gln Xaa Pro Gly Leu Cys Arg His Gly Gly
1               5                   10                  15

Thr Cys His Asn Glu Val Gly Ser Tyr Arg Cys Val Cys Arg Ala Thr
            20                  25                  30

His Thr Gly Pro Asn Cys Glu
        35

<210> SEQ ID NO 34
<211> LENGTH: 39
<212> TYPE: PRT
<213> ORGANISM: Homo sapiens

<400> SEQUENCE: 34

```
Arg Pro Tyr Val Pro Cys Ser Pro Ser Pro Cys Gln Asn Gly Gly Thr
1               5                   10                  15

Cys Arg Pro Thr Gly Asp Val Thr His Glu Cys Ala Cys Leu Pro Gly
                20                  25                  30

Phe Thr Gly Gln Asn Cys Glu
                35

<210> SEQ ID NO 35
<211> LENGTH: 38
<212> TYPE: PRT
<213> ORGANISM: Homo sapiens

<400> SEQUENCE: 35

Glu Asn Ile Asp Asp Cys Pro Gly Asn Asn Cys Lys Asn Gly Gly Ala
1               5                   10                  15

Cys Val Asp Gly Val Asn Thr Tyr Asn Cys Arg Cys Pro Pro Glu Trp
                20                  25                  30

Thr Gly Gln Tyr Cys Thr
                35

<210> SEQ ID NO 36
<211> LENGTH: 40
<212> TYPE: PRT
<213> ORGANISM: Homo sapiens

<400> SEQUENCE: 36

Glu Asp Val Asp Glu Cys Gln Leu Met Pro Asn Ala Cys Gln Asn Gly
1               5                   10                  15

Gly Thr Cys His Asn Thr His Gly Gly Tyr Asn Cys Val Cys Val Asn
                20                  25                  30

Gly Trp Thr Gly Glu Asp Cys Ser
                35                  40

<210> SEQ ID NO 37
<211> LENGTH: 38
<212> TYPE: PRT
<213> ORGANISM: Homo sapiens

<400> SEQUENCE: 37

Glu Asn Ile Asp Asp Cys Ala Ser Ala Ala Cys Phe His Gly Ala Thr
1               5                   10                  15

Cys His Asp Arg Val Ala Ser Pro Tyr Cys Glu Cys Pro His Gly Arg
                20                  25                  30

Thr Gly Leu Leu Cys His
                35

<210> SEQ ID NO 38
<211> LENGTH: 39
<212> TYPE: PRT
<213> ORGANISM: Homo sapiens

<400> SEQUENCE: 38

Leu Asn Asp Ala Cys Ile Ser Asn Pro Cys Asn Glu Gly Ser Asn Cys
1               5                   10                  15

Asp Thr Asn Pro Val Asn Gly Lys Ala Ile Cys Thr Cys Pro Ser Gly
                20                  25                  30

Tyr Thr Gly Pro Ala Cys Ser
                35
```

```
<210> SEQ ID NO 39
<211> LENGTH: 40
<212> TYPE: PRT
<213> ORGANISM: Homo sapiens

<400> SEQUENCE: 39

Gln Asp Val Asp Glu Cys Ser Leu Gly Ala Asn Pro Cys Glu His Ala
1               5                   10                  15

Gly Lys Cys Ile Asn Thr Leu Gly Ser Pro Glu Cys Gln Cys Leu Gln
            20                  25                  30

Gly Tyr Thr Gly Pro Arg Cys Glu
        35                  40

<210> SEQ ID NO 40
<211> LENGTH: 41
<212> TYPE: PRT
<213> ORGANISM: Homo sapiens

<400> SEQUENCE: 40

Glu Asp Val Asp Glu Cys Ala Met Ala Asn Ser Asn Pro Cys Glu His
1               5                   10                  15

Ala Gly Lys Cys Val Asn Thr Asp Gly Ala Pro His Cys Glu Cys Leu
            20                  25                  30

Lys Gly Tyr Ala Gly Pro Arg Cys Glu
        35                  40

<210> SEQ ID NO 41
<211> LENGTH: 40
<212> TYPE: PRT
<213> ORGANISM: Homo sapiens

<400> SEQUENCE: 41

Gln Asp Val Asp Glu Cys Ser Ile Gly Ala Asn Pro Cys Glu His Leu
1               5                   10                  15

Gly Arg Cys Val Asn Thr Gln Gly Ser Pro Leu Cys Gln Cys Gly Arg
            20                  25                  30

Gly Tyr Thr Gly Pro Arg Cys Glu
        35                  40

<210> SEQ ID NO 42
<211> LENGTH: 43
<212> TYPE: PRT
<213> ORGANISM: Homo sapiens

<400> SEQUENCE: 42

Gln Asp Leu Asp Glu Cys Leu Met Ala Gln Gln Gly Pro Ser Pro Cys
1               5                   10                  15

Glu His Gly Gly Ser Cys Leu Asn Thr Pro Gly Ser Pro Asn Cys Leu
            20                  25                  30

Cys Pro Pro Gly Tyr Thr Gly Ser Arg Cys Glu
        35                  40

<210> SEQ ID NO 43
<211> LENGTH: 39
<212> TYPE: PRT
<213> ORGANISM: Xenopus sp.

<400> SEQUENCE: 43

Asp Val Asp Glu Cys Ser Leu Gly Ala Asn Pro Cys Glu His Gly Gly
1               5                   10                  15
```

```
Arg Cys Thr Asn Thr Leu Gly Ser Pro Gln Cys Asn Cys Pro Gln Gly
            20                  25                  30

Tyr Ala Gly Pro Arg Cys Glu
        35
```

<210> SEQ ID NO 44
<211> LENGTH: 38
<212> TYPE: PRT
<213> ORGANISM: Drosophila sp.

<400> SEQUENCE: 44

```
Asp Ile Asp Glu Cys Asp Gln Gly Ser Pro Cys Glu His Asn Gly Ile
1               5                   10                  15

Cys Val Asn Thr Pro Gly Ser Tyr Arg Cys Asn Cys Ser Gln Gly Phe
            20                  25                  30

Thr Gly Pro Arg Cys Glu
        35
```

<210> SEQ ID NO 45
<211> LENGTH: 39
<212> TYPE: PRT
<213> ORGANISM: Caenorhabditis elegans

<400> SEQUENCE: 45

```
Glu Pro Leu Asn Met Cys Gln Asp Phe His Cys Glu Asn Asp Gly Thr
1               5                   10                  15

Cys Met His Thr Ser Asp His Ser Pro Val Cys Gln Cys Lys Asn Gly
            20                  25                  30

Phe Ile Gly Lys Arg Cys Glu
        35
```

<210> SEQ ID NO 46
<211> LENGTH: 38
<212> TYPE: PRT
<213> ORGANISM: Homo sapiens

<400> SEQUENCE: 46

```
Ile Asp Val Asn Glu Cys Val Ser Asn Pro Cys Gln Asn Asp Ala Thr
1               5                   10                  15

Cys Leu Asp Gln Ile Gly Glu Pro Gln Cys Ile Cys Met Pro Gly Tyr
            20                  25                  30

Glu Gly Val Arg Cys Glu
        35
```

<210> SEQ ID NO 47
<211> LENGTH: 38
<212> TYPE: PRT
<213> ORGANISM: Homo sapiens

<400> SEQUENCE: 47

```
Val Asn Thr Asp Glu Cys Ala Ser Ser Pro Cys Leu His Asn Gly Arg
1               5                   10                  15

Cys Leu Asp Lys Ile Asn Glu Pro Gln Cys Glu Cys Pro Thr Gly Phe
            20                  25                  30

Thr Gly His Leu Cys Gln
        35
```

<210> SEQ ID NO 48
<211> LENGTH: 38
<212> TYPE: PRT
<213> ORGANISM: Homo sapiens

```
<400> SEQUENCE: 48

Tyr Asp Val Asp Glu Cys Ala Ser Thr Pro Cys Lys Asn Gly Ala Lys
1               5                   10                  15

Cys Leu Asp Gly Pro Asn Thr Tyr Thr Cys Val Cys Thr Glu Gly Tyr
            20                  25                  30

Thr Gly Thr His Cys Glu
        35

<210> SEQ ID NO 49
<211> LENGTH: 37
<212> TYPE: PRT
<213> ORGANISM: Homo sapiens

<400> SEQUENCE: 49

Val Asp Ile Asp Glu Cys Asp Pro Asp Pro Cys His Tyr Gly Ser Cys
1               5                   10                  15

Lys Asp Gly Val Ala Thr Pro Thr Cys Leu Cys Arg Pro Gly Tyr Thr
            20                  25                  30

Gly His His Cys Glu
        35

<210> SEQ ID NO 50
<211> LENGTH: 38
<212> TYPE: PRT
<213> ORGANISM: Homo sapiens

<400> SEQUENCE: 50

Thr Asn Ile Asn Glu Cys Ser Ser Gln Pro Cys Arg His Gly Gly Thr
1               5                   10                  15

Cys Gln Asp Arg Asp Asn Ala Tyr Leu Cys Phe Cys Leu Lys Gly Thr
            20                  25                  30

Thr Gly Pro Asn Cys Glu
        35

<210> SEQ ID NO 51
<211> LENGTH: 37
<212> TYPE: PRT
<213> ORGANISM: Homo sapiens

<400> SEQUENCE: 51

Ile Asn Leu Asp Asp Cys Ala Ser Ser Pro Cys Asp Ser Gly Thr Cys
1               5                   10                  15

Leu Asp Lys Ile Asp Gly Tyr Glu Cys Ala Cys Glu Pro Gly Tyr Thr
            20                  25                  30

Gly Ser Met Cys Asn
        35

<210> SEQ ID NO 52
<211> LENGTH: 38
<212> TYPE: PRT
<213> ORGANISM: Homo sapiens

<400> SEQUENCE: 52

Ile Asn Ile Asp Glu Cys Ala Gly Asn Pro Cys His Asn Gly Gly Thr
1               5                   10                  15

Cys Glu Asp Gly Ile Asn Gly Pro Thr Cys Arg Cys Pro Glu Gly Tyr
            20                  25                  30

His Asp Pro Thr Cys Leu
        35
```

<210> SEQ ID NO 53
<211> LENGTH: 37
<212> TYPE: PRT
<213> ORGANISM: Homo sapiens

<400> SEQUENCE: 53

Ser Glu Val Asn Glu Cys Asn Ser Asn Pro Cys Val His Gly Ala Cys
1               5                   10                  15

Arg Asp Ser Leu Asn Gly Tyr Lys Cys Asp Cys Asp Pro Gly Trp Ser
            20                  25                  30

Gly Thr Asn Cys Asp
        35

<210> SEQ ID NO 54
<211> LENGTH: 38
<212> TYPE: PRT
<213> ORGANISM: Homo sapiens

<400> SEQUENCE: 54

Ile Asn Asn Asn Glu Cys Glu Ser Asn Pro Cys Val Asn Gly Gly Thr
1               5                   10                  15

Cys Lys Asp Met Thr Ser Gly Tyr Val Cys Thr Cys Arg Glu Gly Phe
            20                  25                  30

Ser Gly Pro Asn Cys Gln
        35

<210> SEQ ID NO 55
<211> LENGTH: 38
<212> TYPE: PRT
<213> ORGANISM: Homo sapiens

<400> SEQUENCE: 55

Thr Asn Ile Asn Glu Cys Ala Ser Asn Pro Cys Leu Asn Gln Gly Thr
1               5                   10                  15

Cys Ile Asp Asp Val Ala Gly Tyr Lys Cys Asn Cys Leu Leu Pro Tyr
            20                  25                  30

Thr Gly Ala Thr Cys Glu
        35

<210> SEQ ID NO 56
<211> LENGTH: 41
<212> TYPE: PRT
<213> ORGANISM: Homo sapiens

<400> SEQUENCE: 56

Val Val Leu Ala Pro Cys Ala Pro Ser Pro Cys Arg Asn Gly Gly Glu
1               5                   10                  15

Cys Arg Gln Ser Glu Asp Tyr Glu Ser Pro Ser Cys Val Cys Pro Thr
            20                  25                  30

Gly Trp Gln Ala Gly Gln Thr Cys Glu
        35                  40

<210> SEQ ID NO 57
<211> LENGTH: 38
<212> TYPE: PRT
<213> ORGANISM: Homo sapiens

<400> SEQUENCE: 57

Val Asp Ile Asn Glu Cys Val Leu Ser Pro Cys Arg His Gly Ala Ser
1               5                   10                  15

Cys Gln Asn Thr His Gly Gly Tyr Arg Cys His Cys Gln Ala Gly Tyr
            20                  25                  30

Ser Gly Arg Asn Cys Glu
            35

<210> SEQ ID NO 58
<211> LENGTH: 38
<212> TYPE: PRT
<213> ORGANISM: Homo sapiens

<400> SEQUENCE: 58

Thr Asp Ile Asp Asp Cys Arg Pro Asn Pro Cys His Asn Gly Gly Ser
1               5                   10                  15

Cys Thr Asp Gly Ile Asn Thr Ala Phe Cys Asp Cys Leu Pro Gly Phe
            20                  25                  30

Arg Gly Thr Phe Cys Glu
            35

<210> SEQ ID NO 59
<211> LENGTH: 38
<212> TYPE: PRT
<213> ORGANISM: Homo sapiens

<400> SEQUENCE: 59

Glu Asp Ile Asn Glu Cys Ala Ser Asp Pro Cys Arg Asn Gly Ala Asn
1               5                   10                  15

Cys Thr Asp Cys Val Asp Ser Tyr Thr Cys Thr Cys Pro Ala Gly Pro
            20                  25                  30

Ser Gly Ile His Cys Glu
            35

<210> SEQ ID NO 60
<211> LENGTH: 38
<212> TYPE: PRT
<213> ORGANISM: Homo sapiens

<400> SEQUENCE: 60

Asn Asn Thr Pro Asp Cys Thr Glu Ser Ser Cys Phe Asn Gly Gly Thr
1               5                   10                  15

Cys Val Asp Gly Ile Asn Ser Pro Thr Cys Leu Cys Pro Pro Gly Phe
            20                  25                  30

Thr Gly Ser Tyr Cys Gln
            35

<210> SEQ ID NO 61
<211> LENGTH: 38
<212> TYPE: PRT
<213> ORGANISM: Homo sapiens

<400> SEQUENCE: 61

His Asp Val Asn Glu Cys Asp Ser Gln Pro Cys Leu His Gly Gly Thr
1               5                   10                  15

Cys Gln Asp Gly Cys Gly Ser Tyr Arg Cys Thr Cys Pro Gln Gly Tyr
            20                  25                  30

Thr Gly Pro Asn Cys Gln
            35

<210> SEQ ID NO 62
<211> LENGTH: 38
<212> TYPE: PRT

<213> ORGANISM: Homo sapiens

<400> SEQUENCE: 62

Asn Leu Val His Trp Cys Asp Ser Ser Pro Cys Lys Asn Gly Gly Lys
1               5                   10                  15

Cys Trp Gln Thr His Thr Gln Tyr Arg Cys Glu Cys Pro Ser Gly Trp
                20                  25                  30

Thr Gly Leu Tyr Cys Asp
            35

<210> SEQ ID NO 63
<211> LENGTH: 48
<212> TYPE: PRT
<213> ORGANISM: Homo sapiens

<400> SEQUENCE: 63

Val Pro Ser Val Ser Cys Glu Val Ala Ala Gln Arg Gln Gly Val Asp
1               5                   10                  15

Val Ala Arg Leu Cys Gln His Gly Gly Leu Cys Val Asp Ala Gly Asn
                20                  25                  30

Thr His Arg Cys Arg Cys Gln Ala Gly Tyr Thr Gly Ser Tyr Cys Glu
            35                  40                  45

<210> SEQ ID NO 64
<211> LENGTH: 38
<212> TYPE: PRT
<213> ORGANISM: Homo sapiens

<400> SEQUENCE: 64

Asp Leu Val Asp Glu Cys Ser Pro Ser Pro Cys Gln Asn Gly Ala Thr
1               5                   10                  15

Cys Thr Asp Tyr Leu Gly Gly Tyr Ser Cys Lys Cys Val Ala Gly Tyr
                20                  25                  30

His Gly Val Asn Cys Ser
            35

<210> SEQ ID NO 65
<211> LENGTH: 38
<212> TYPE: PRT
<213> ORGANISM: Homo sapiens

<400> SEQUENCE: 65

Glu Glu Ile Asp Glu Cys Leu Ser His Pro Cys Gln Asn Gly Gly Thr
1               5                   10                  15

Cys Leu Asp Leu Pro Asn Thr Tyr Lys Cys Ser Cys Pro Arg Gly Thr
                20                  25                  30

Gln Gly Val His Cys Glu
            35

<210> SEQ ID NO 66
<211> LENGTH: 46
<212> TYPE: PRT
<213> ORGANISM: Homo sapiens

<400> SEQUENCE: 66

Ile Asn Val Asp Asp Cys Asn Pro Pro Val Asp Pro Val Ser Arg Ser
1               5                   10                  15

Pro Lys Cys Phe Asn Asn Gly Thr Cys Val Asp Gln Val Gly Gly Tyr
                20                  25                  30

```
Ser Cys Thr Cys Pro Pro Gly Pro Val Gly Glu Arg Cys Glu
        35                  40                  45

<210> SEQ ID NO 67
<211> LENGTH: 40
<212> TYPE: PRT
<213> ORGANISM: Homo sapiens

<400> SEQUENCE: 67

Gly Asp Val Asn Glu Cys Leu Ser Asn Pro Cys Asp Ala Arg Gly Thr
1               5                   10                  15

Gln Asn Cys Val Gln Arg Val Asn Asp Pro His Cys Glu Cys Arg Ala
            20                  25                  30

Gly His Thr Gly Arg Arg Cys Glu
        35                  40

<210> SEQ ID NO 68
<211> LENGTH: 41
<212> TYPE: PRT
<213> ORGANISM: Homo sapiens

<400> SEQUENCE: 68

Ser Val Ile Asn Gly Cys Lys Gly Lys Pro Cys Lys Asn Gly Gly Thr
1               5                   10                  15

Cys Ala Val Ala Ser Asn Thr Ala Arg Gly Pro Ile Cys Lys Cys Pro
            20                  25                  30

Ala Gly Phe Glu Gly Ala Thr Cys Glu
        35                  40

<210> SEQ ID NO 69
<211> LENGTH: 38
<212> TYPE: PRT
<213> ORGANISM: Homo sapiens

<400> SEQUENCE: 69

Asn Asp Ala Arg Thr Cys Gly Ser Leu Arg Cys Leu Asn Gly Gly Thr
1               5                   10                  15

Cys Ile Ser Gly Pro Arg Ser Pro Thr Cys Leu Cys Leu Gly Pro Phe
            20                  25                  30

Thr Gly Pro Glu Cys Gln
        35

<210> SEQ ID NO 70
<211> LENGTH: 42
<212> TYPE: PRT
<213> ORGANISM: Homo sapiens

<400> SEQUENCE: 70

Phe Pro Ala Ser Ser Pro Cys Leu Gly Gly Asn Pro Cys Tyr Asn Gln
1               5                   10                  15

Gly Thr Cys Glu Pro Thr Ser Glu Ser Pro Phe Tyr Arg Cys Leu Cys
            20                  25                  30

Pro Ala Lys Phe Asn Gly Leu Leu Cys His
        35                  40
```